US005296467A

United States Patent [19]

Reutelingsperger

[11] Patent Number: 5,296,467

[45] Date of Patent: Mar. 22, 1994

[54] COMPOSITION COMPRISING AN ANTICOAGULANT

[75] Inventor: Christiaan Reutelingsperger, JK Masstricht, Netherlands

[73] Assignee: Boehringer Ingelheim International GmbH, Fed. Rep. of Germany

[21] Appl. No.: 873,601

[22] Filed: Apr. 21, 1992

Related U.S. Application Data

[63] Continuation of Ser. No. 552,198, Jul. 13, 1990, abandoned.

[30] Foreign Application Priority Data

Jul. 15, 1989 [DE] Fed. Rep. of Germany ....... 3923500

[51] Int. Cl.[5] ...................... C07K 13/00; A61K 37/02

[52] U.S. Cl. ........................................ 514/12; 514/2; 514/21; 424/529; 424/583; 530/350; 530/380; 530/381

[58] Field of Search ............... 530/350, 380, 381, 830, 530/851; 424/529, 583; 514/2, 12, 21, 802, 5

[56] References Cited

U.S. PATENT DOCUMENTS

| | | | |
|---|---|---|---|
| 4,507,229 | 3/1985 | Bohn | 260/112 B |
| 4,732,891 | 3/1988 | Maki et al. | 514/21 |
| 4,736,018 | 4/1988 | Reutelingsperger | 530/381 |
| 4,746,731 | 5/1988 | Bohn et al. | 530/394 |
| 4,748,156 | 5/1988 | Aoki et al. | 514/21 |

FOREIGN PATENT DOCUMENTS

| | | |
|---|---|---|
| 0181465 | 5/1986 | European Pat. Off. . |
| 0293567 | 12/1988 | European Pat. Off. . |
| 0318703 | 6/1989 | European Pat. Off. . |
| 0409053 | 1/1991 | European Pat. Off. . |
| 0123307 | 10/1994 | European Pat. Off. . |
| 3710430 | 1/1989 | Fed. Rep. of Germany . |
| 8800210 | 1/1988 | PCT Int'l Appl. . |

OTHER PUBLICATIONS

Di Rosa, M. et al., *Prostaglandins* 28 (4):441 (1984).

Funakoshi, T. et al., *Biochemistry* 26:8087-8092.

Geisow, M. J. et al., *Biochem. Soc. Transactions* 15:800-802 (1987).

Hirata, F., *J. Biol. Chem.* 256:7730-7733 (1981).

Kaetzel, M. A. et al., *The Journal of Biological Chemistry* 264:14463-14470 (1989).

Maki, M. et al., *Eur. J. Obstet. Gyn. Reprd. Biol.* 17:149-154 (1984).

Miller-Anderson, M. et al., *Thromb. Res.* 5:439-452 (1974).

Reutelingsperger, C. P. M., et al., *Eur. J. Biochem.* 151:625-629 (1985).

Schapira, M. et al., *Biochemistry*: 20:2738-2743 (1981).

Shitara, Y., et al., *Blood and Vessel* 14:498-500 (1983).

Iwasaki, Akio, et al., *J. Biochem.* 106:43-49 (1989).

Yoshizaki, H. et al., *J. Biochem.* 105:178-183 (1989).

Tait, J. F. *Biochem.* 27:6268-6276 (1988).

Reutelingsperger et al., *Eur. J. Biochem.* 173:171-178 (1988).

Maurer-Fogy et al., *Eur. J. Biochem.* 174:585-592 (1988).

*Harrison's Principles of Internal Medicine*, 11th Edition, pp. 418-421, Braunwald, E. et al., McGraw-Hill Book Company (1987).

Crompton et al., Diversity in the Lipocortin/Calpactin Family, *Cell* 55:1-3 (1988).

*Primary Examiner*—Michael G. Wityshyn

*Assistant Examiner*—C. Sayala

*Attorney, Agent, or Firm*—Sterne, Kessler, Goldstein & Fox

[57] ABSTRACT

Pharmaceutical compositions which consist essentially of a vascular anticoagulant annexine, $Ca^{2+}$, $Zn^{2+}$, and a pharmaceutically acceptable carrier are disclosed. Also disclosed are processes for preparing such pharmaceutical compositions. Also disclosed are methods of preventing the coagulation of blood by mixing the blood with a vascular anticoagulant annexine, $Ca^{2+}$ and $Zn^{2+}$.

18 Claims, 73 Drawing Sheets

Tryptic Peptides

| | |
|---|---|
| P5 | H A L K |
| P7 | G E T S G D Y K |
| P11/I | W G T D E E K |
| P11/II | T P E E L R |
| P12 | G A G T D D H T L I R |
| P14 | Q E I S A A F K |
| P15 | T L F G R |
| P16/I | L Y D A Y E L K |
| P16/II | W?L Y D A Y E L K |
| P17 | V L T E I I A S R |
| P18 | G T V T D F P G F D E R |
| P20/I | Q V Y E E E Y G S S L E D D V V G D T S G Y Y Q R |
| P20/II | L I V A L M K |
| P21/I | S E I D L F N I R K |
| P23/I | F I T I F G T R |
| P24 | K N F A T S L Y S M I K |
| P25 | S?G T D E E K F I T I F G T |
| P27 | D L L D D L K S E L T G K F E K |
| P29/I | G L G T D E E S I L T L L T S R |
| P29/II | M L V V L L Q A N R D P D A G I D E A Q V X Q X A Q A L F Q A |
| P30/I | X I P A Y L A E T L Y Y A M K |
| P30/II | E T X G N L E Q L L L A V V K |

BrCN-Peptides

| | |
|---|---|
| BrCN 1 | K G A G T D D H T L I R V |
| BrCN 4 | I K G D T S G D Y K K A |
| BrCN 15 | K P S R L Y D A Y E L K H A L K G A G T N E K V L T E I I |
| BrCN 22 | K G L G T D E E S I L T L L T S X X N A Q |

FIG. 1

Tryptic peptide P16/II

```
        W? L  Y  D  A  Y  E  L  K
5'   ...UGGCUNUAUGAUGCNUAUGAA...   3'          mRNA
              C  C     C  G
        UUA
          G

3'      ACCGAAATACTACGAATACT       5'
           G  G  G  G  G                 EBI - 387
           C        C
           T        T

3'      ACCAACATACTACGAATACT       5'
           T  G  G  G  G                 EBI - 388
                    C
                    T
```

Staph-A Peptide P20/I/6
(Subfragment of the tryptic peptide P20/I)

```
        D  D  V  V  G  D  T  S  G  Y  Y  R
5'   ...GAUGAUGUNGUNGGNGAUACN...   3'            mRNA
         C  C           C

3'      CTACTACAACAACCACTATG       5'
         G  G  G  G  G  G                EBI - 386
               C  C  C
               T  T  T
```

FIG.7

TRYPTIC PEPTIDE P30/I

```
X  I  P  A  Y  L  A  E  T  L  Y  Y  A  M  K
            5'  ...GAAACNCUNUACUACGCNAUGAAA...  3'   mRNA
                     G      U  U        G
                        UUA
                         G

            3'   CTCTGIIAIATIATICGITACTT      5'   EBI - 118
            3'   CTTTGIIAIATIATICGITACTT      5'   EBI - 119
```

FIG.8

```
                         CCTGCTTCACCTTCCCCTGACCTGAGTAGTCGCT

  1               5                  10                  15
Met Ala Gln Val Leu Arg Gly Thr Val Thr Asp Phe Pro Gly Phe
ATG GCA CAG GTT CTC AGA GGC ACT GTG ACT GAC TTC CCT GGA TTT    45

                 20                  25                  30
Asp Glu Arg Ala Asp Ala Glu Thr Leu Arg Lys Ala Met Lys Gly
GAT GAG CGG GCT GAT GCA GAA ACT CTT CGG AAG GCT ATG AAA GGC    90

                 35                  40                  45
Leu Gly Thr Asp Glu Glu Ser Ile Leu Thr Leu Leu Thr Ser Arg
TTG GGC ACA GAT GAG GAG AGC ATC CTG ACT CTG TTG ACA TCC CGA   135

                 50                  55                  60
Ser Asn Ala Gln Arg Gln Glu Ile Ser Ala Ala Phe Lys Thr Leu
AGT AAT GCT CAG CGC CAG GAA ATC TCT GCA GCT TTT AAG ACT CTG   180

                 65                  70                  75
Phe Gly Arg Asp Leu Leu Asp Asp Leu Lys Ser Glu Leu Thr Gly
TTT GGC AGG GAT CTT CTG GAT GAC CTG AAA TCA GAA CTA ACT GGA   225

                 80                  85                  90
Lys Phe Glu Lys Leu Ile Val Ala Leu Met Lys Pro Ser Arg Leu
AAA TTT GAA AAA TTA ATT GTG GCT CTG ATG AAA CCC TCT CGG CTT   270
```

FIG.10a

```
                    95                                     100                                    105
Tyr Asp Ala Tyr Glu Leu Lys His Ala Leu Lys Gly Ala Gly Thr
TAT GAT GCT TAT GAA CTG AAA CAT GCC TTG AAG GGA GCT GGA ACA   315

                    110                                    115                                    120
Asn Glu Lys Val Leu Thr Glu Ile Ile Ala Ser Arg Thr Pro Glu
AAT GAA AAA GTA CTG ACA GAA ATT ATT GCT TCA AGG ACA CCT GAA   360

                    125                                    130                                    135
Glu Leu Arg Ala Ile Lys Gln Val Tyr Glu Glu Glu Tyr Gly Ser
GAA CTG AGA GCC ATC AAA CAA GTT TAT GAA GAA GAA TAT GGC TCA   405

                    140                                    145                                    150
Ser Leu Glu Asp Asp Val Val Gly Asp Thr Ser Gly Tyr Tyr Gln
AGC CTG GAA GAT GAC GTG GTG GGG GAC ACT TCA GGG TAC TAC CAG   450
```

FIG. 10b

```
                155                 160                 165
Arg Met Leu Val Val Leu Leu Gln Ala Asn Arg Asp Pro Asp Ala
CGG ATG TTG GTG GTT CTC CTT CAG GCT AAC AGA GAC CCT GAT GCT   495

                170                 175                 180
Gly Ile Asp Glu Ala Gln Val Glu Gln Asp Ala Gln Ala Leu Phe
GGA ATT GAT GAA GCT CAA GTT GAA CAA GAT GCT CAG GCT TTA TTT   540

                185                 190                 195
Gln Ala Gly Glu Leu Lys Trp Gly Thr Asp Glu Glu Lys Phe Ile
CAG GCT GGA GAA CTT AAA TGG GGG ACA GAT GAA GAA AAG TTT ATC   585

                200                 205                 210
Thr Ile Phe Gly Thr Arg Ser Val Ser His Leu Arg Lys Val Phe
ACC ATC TTT GGA ACA CGA AGT GTG TCT CAT TTG AGA AAG GTG TTT   630

                215                 220                 225
Asp Lys Tyr Met Thr Ile Ser Gly Phe Gln Ile Glu Glu Thr Ile
GAC AAG TAC ATG ACT ATA TCA GGA TTT CAA ATT GAG GAA ACC ATT   675

                230                 235                 240
Asp Arg Glu Thr Ser Gly Asn Leu Glu Gln Leu Leu Leu Ala Val
GAC CGC GAG ACT TCT GGC AAT TTA GAG CAA CTA CTC CTT GCT GTT   720
```

FIG.10c

```
                    245                     250                     255
Val Lys Ser Ile Arg Ser Ile Pro Ala Tyr Leu Ala Glu Thr Leu
GTG AAA TCT ATT CGA AGT ATA CCT GCC TAC CTT GCA GAG ACC CTC    765

                    260                     265                     270
Tyr Tyr Ala Met Lys Gly Ala Gly Thr Asp Asp His Thr Leu Ile
TAT TAT GCT ATG AAG GGA GCT GGG ACA GAT GAT CAT ACC CTC ATC    810

                    275                     280                     285
Arg Val Met Val Ser Arg Ser Glu Ile Asp Leu Phe Asn Ile Arg
AGA GTC ATG GTT TCC AGG AGT GAG ATT GAT CTG TTT AAC ATC AGG    855

                    290                     295                     300
Lys Glu Phe Arg Lys Asn Phe Ala Thr Ser Leu Tyr Ser Met Ile
AAG GAG TTT AGG AAG AAT TTT GCC ACC TCT CTT TAT TCC ATG ATT    900

                    305                     310                     315
Lys Gly Asp Thr Ser Gly Asp Tyr Lys Lys Ala Leu Leu Leu Leu
AAG GGA GAT ACA TCT GGG GAC TAT AAG AAA GCT CTT CTG CTG CTC    945

                    320
Cys Gly Glu Asp Asp  *
TGT GGA GAA GAT GAC TAA CGTGTCACGGGGAAGAGCTCCCTGCTGTGTGCCTG    998
```

FIG. 10d

```
CACCACCCCACTGCCTTCCTTCAGCACCTTTAGCTGCATTTGTATGCCAGTGCTTAACA  1057
CATTGCCTTATTCATACTAGCATGCTCATGACCAACACATACACGTCATAGAAGAAAAT  1116
AGTGGTGCTTCTTTCTGATCTCTAGTGGAGATCTCTTTGACTGCTGTAGTACTAAAGTG  1175
TACTTAATGTTACTAAGTTTAATGCCTGGCCATTTTCCATTTATATATATTTTTTAAGA  1234
GGCTAGAGTGCTTTTAGCCTTTTTTAAAAACTCCATTTATATTACATTTGTAACCATGA  1293
TACTTTAATCAGAAGCTTAGCCTTGAAATTGTGAACTCTTGGAAATGTTATTAGTGAAG  1352
TTCGCAACTAAACTAAACCTGTAAAATTATGATGATTGTATTCAAAAGATTAATGAAAA  1411
ATAAACATTTCTGTCCCCCTG-polyA                                  1437
```

FIG. 10e

Figure 11A:
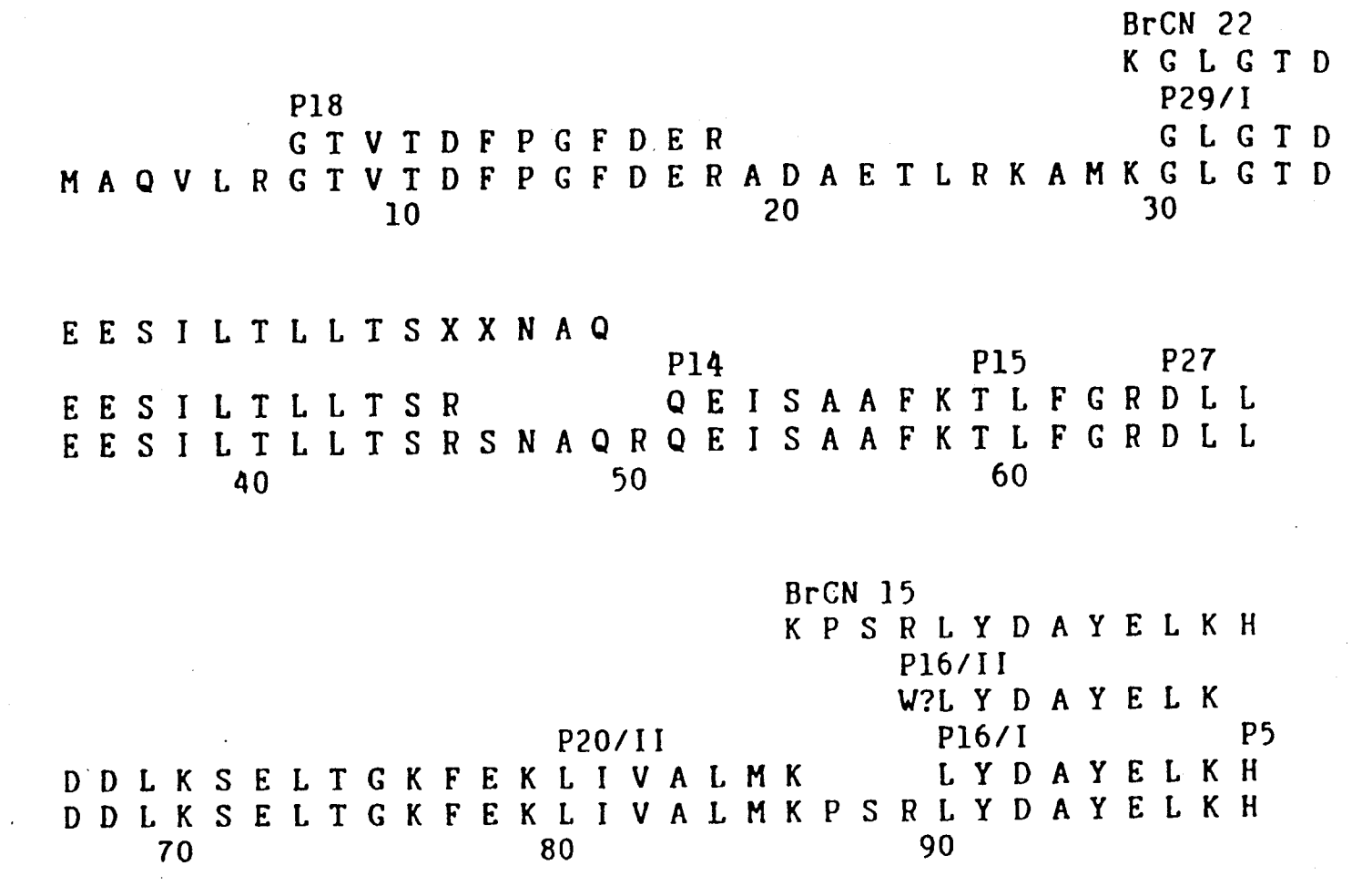

```
                                                          BrCN 22
                                                          K G L G T D
            P18                                             P29/I
            G T V T D F P G F D E R                         G L G T D
M A Q V L R G T V T D F P G F D E R A D A E T L R K A M K G L G T D
                10                   20                   30

E E S I L T L L T S X X N A Q
                                  P14             P15      P27
E E S I L T L L T S R             Q E I S A A F K T L F G R D L L
E E S I L T L L T S R S N A Q R Q E I S A A F K T L F G R D L L
          40                   50                   60

                                                 BrCN 15
                                                 K P S R L Y D A Y E L K H
                                                       P16/II
                                                       W?L Y D A Y E L K
                            P20/II                       P16/I           P5
D D L K S E L T G K F E K L I V A L M K                  L Y D A Y E L K H
D D L K S E L T G K F E K L I V A L M K P S R L Y D A Y E L K H
      70                   80                   90
```

Figure 11B:
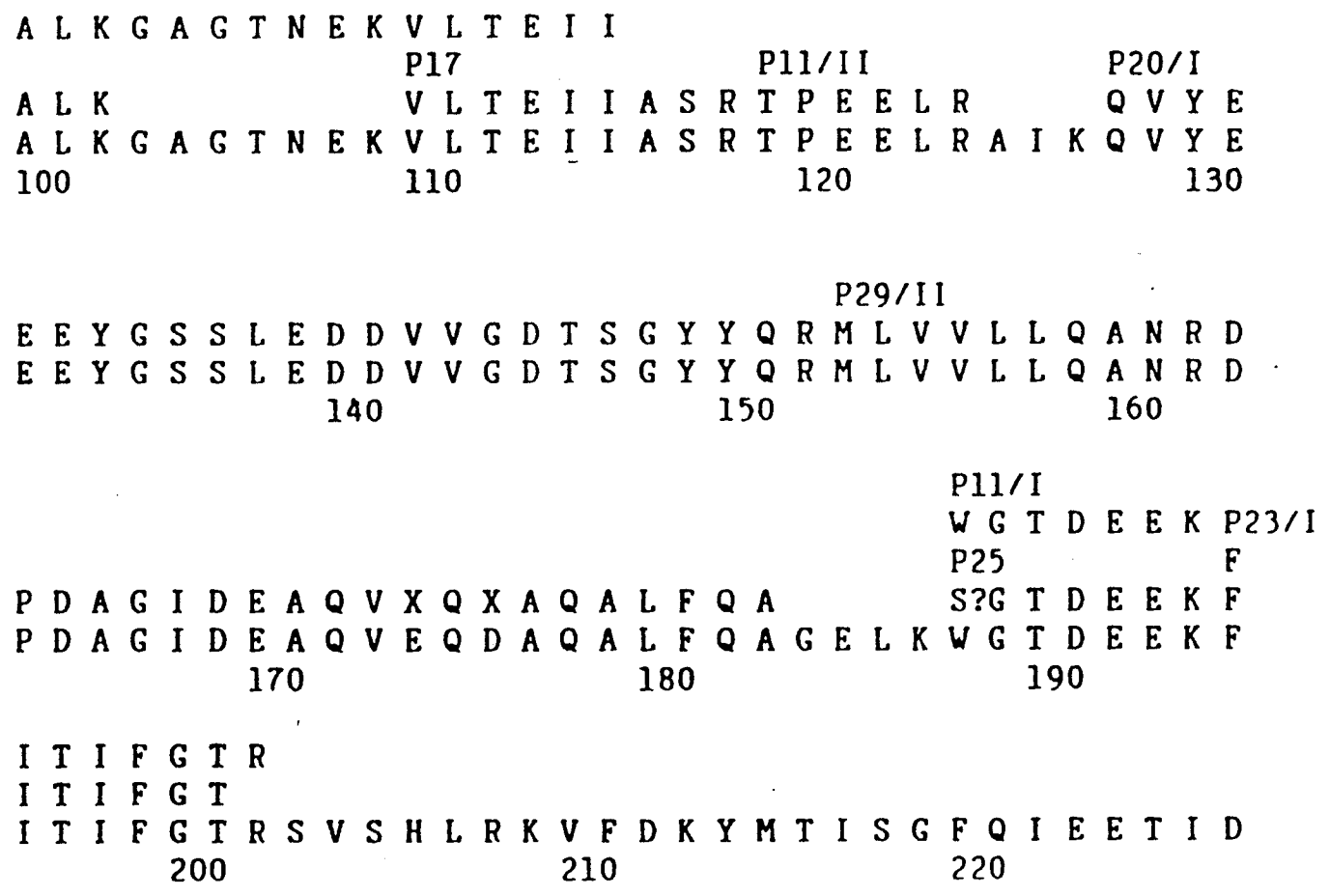

```
A L K G A G T N E K V L T E I I
                    P17                 P11/II              P20/I
A L K               V L T E I I A S R T P E E L R           Q V Y E
A L K G A G T N E K V L T E I I A S R T P E E L R A I K Q V Y E
100                 110                   120                 130

                                                  P29/II
E E Y G S S L E D D V V G D T S G Y Y Q R M L V V L L Q A N R D
E E Y G S S L E D D V V G D T S G Y Y Q R M L V V L L Q A N R D
                140                   150                   160

                                                        P11/I
                                                        W G T D E E K P23/I
                                                        P25           F
P D A G I D E A Q V X Q X A Q A L F Q A                 S?G T D E E K F
P D A G I D E A Q V E Q D A Q A L F Q A G E L K W G T D E E K F
            170                   180                   190

I T I F G T R
I T I F G T
I T I F G T R S V S H L R K V F D K Y M T I S G F Q I E E T I D
        200                   210                   220
```

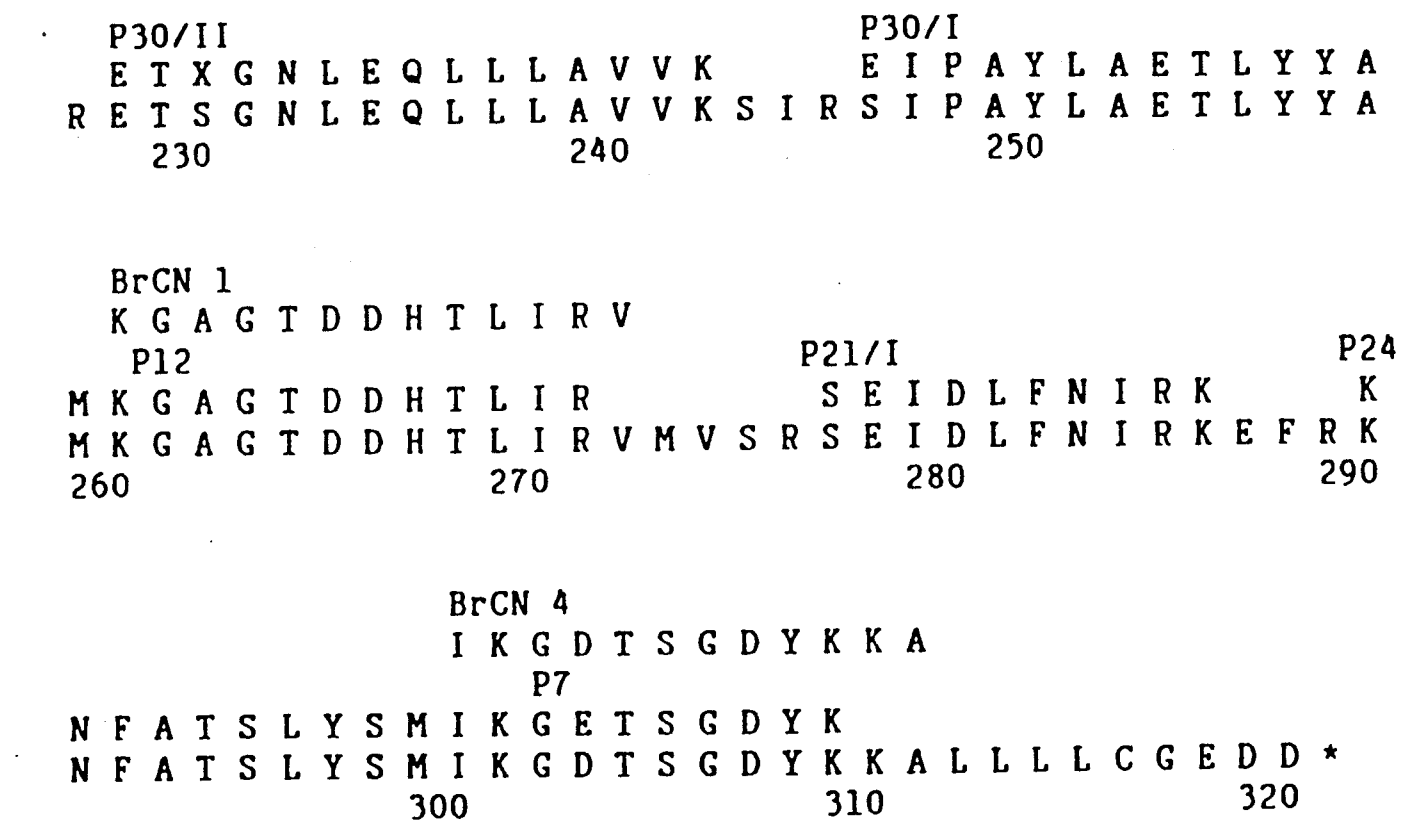

```
   P30/II                                  P30/I
   E T X G N L E Q L L L A V V K           E I P A Y L A E T L Y Y A
 R E T S G N L E Q L L L A V V K S I R S I P A Y L A E T L Y Y A
     230                 240                  250

   BrCN 1
   K G A G T D D H T L I R V
    P12                                  P21/I                     P24
 M K G A G T D D H T L I R               S E I D L F N I R K         K
 M K G A G T D D H T L I R V M V S R S E I D L F N I R K E F R K
 260                 270                  280                 290

                 BrCN 4
                 I K G D T S G D Y K K A
                     P7
 N F A T S L Y S M I K G E T S G D Y K
 N F A T S L Y S M I K G D T S G D Y K K A L L L L C G E D D *
                 300                 310                 320
```

FIG. 11c

```
                                             MAQVLRGTVTDFPGFDERA

DAETLRKAMKG-LGTDEESILTLLTSRSNAQRQEISAAFKTLFGRDLLDDLKSELTGKFEKLIVALMK   PSRLY

DAYELKHALKG-AGTNEKVLTEIIASRTPEELRAIKQVYEEEYGSSLEDDVVGDTSGYYQRMLVVLLQ   ANRDPDAGIDEAQVI

DAQALFQAGELKWGTDEEKFITIFGTRSVSHLRKVFDKYMTISGFQIEETIDRETSGNLEQLLLAVVK   SIRSIPAY

LAETLYYAMKG-AGTDDHTLIRVMVSRSEIDLFNIRKEFRKNFATSLYSMIKGDTSGDYKKALLLLCG   EDD*

      KG-hGTDExxLIpILApR                                      oooooo

DAetL  AmKG aGTDEe lltl  SRS  Lr I   y t fG sLeddlkgeTSG yeklLvaL k
                                                 d        l

    "Consensus":          x :  50% of amino acids identical
                          X :  75% of amino acids identical
                          X : 100% of amino acids identical

     "oooooo" :           Hydrophobic region
```

FIG. 12

```
                 AGGCCTGCTCACTCCTCAGCTGCAGGAGCCAGACGTGTGGAGTCCCA

GCAGAGGCCAACCTGTGTCTCTTCATCTCCGTGAGAAAGGTGCCCCCGAAGTGAAAGAG

  1               5                  10                  15
Met Ala Trp Trp Lys Ala Trp Ile Glu Gln Glu Gly Val Thr Val
ATG GCC TGG TGG AAA GCC TGG ATT GAA CAG GAG GGT GTC ACA GTG     45

                 20                  25                  30
Lys Ser Ser Ser His Phe Asn Pro Asp Pro Asp Ala Glu Thr Leu
AAG AGC AGC TCC CAC TTC AAC CCA GAC CCT GAT GCA GAG ACC CTC     90

                 35                  40                  45
Tyr Lys Ala Met Lys Gly Ile Gly Thr Asn Glu Gln Ala Ile Ile
TAC AAA GCC ATG AAG GGG ATC GGG ACC AAC GAG CAG GCT ATC ATC    135

                 50                  55                  60
Asp Val Leu Thr Lys Arg Ser Asn Thr Gln Arg Gln Gln Ile Ala
GAT GTG CTC ACC AAG AGA AGC AAC ACG CAG CGG CAG CAG ATC GCC    180

                 65                  70                  75
Lys Ser Phe Lys Ala Gln Phe Gly Lys Asp Leu Thr Glu Thr Leu
AAG TCC TTC AAG GCT CAG TTC GGC AAG GAC CTC ACT GAG ACC TTG    225
```

FIG. 13a

```
                    80                  85                  90
Lys Ser Glu Leu Ser Gly Lys Phe Glu Arg Leu Ile Val Ala Leu
AAG TCT GAG CTC AGT GGC AAG TTT GAG AGG CTC ATT GTG GCC CTT   270

                    95                 100                 105
Met Tyr Pro Pro Tyr Arg Tyr Glu Ala Lys Glu Leu His Asp Ala
ATG TAT CCG CCA TAC AGA TAC GAA GCC AAG GAG CTG CAT GAC GCC   315

                   110                 115                 120
Met Lys Gly Leu Gly Thr Lys Glu Gly Val Ile Ile Glu Ile Leu
ATG AAG GGC TTA GGA ACC AAG GAG GGT GTC ATC ATT GAG ATC CTG   360

                   125                 130                 135
Ala Ser Arg Thr Lys Asn Gln Leu Arg Glu Ile Met Lys Ala Tyr
GCC TCT CGG ACC AAG AAC CAG CTG CGG GAG ATA ATG AAG GCG TAT   405

                   140                 145                 150
Glu Glu Asp Tyr Gly Ser Ser Leu Glu Glu Asp Ile Gln Ala Asp
GAG GAA GAC TAT GGG TCC AGC CTG GAG GAG GAC ATC CAA GCA GAC   450
```

FIG. 13b

```
                155                 160                 165
Thr Ser Gly Tyr Leu Glu Arg Ile Leu Val Cys Leu Leu Gln Gly
ACA AGT GGC TAC CTG GAG AGG ATC CTG GTG TGC CTC CTG CAG GGC   495

                170                 175                 180
Ser Arg Asp Asp Val Ser Ser Phe Val Asp Pro Ala Leu Ala Leu
AGC AGG GAT GAT GTG AGC AGC TTT GTG GAC CCG GCA CTG GCC CTC   540

                185                 190                 195
Gln Asp Ala Gln Asp Leu Tyr Ala Ala Gly Glu Lys Ile Arg Gly
CAA GAC GCA CAG GAT CTG TAT GCG GCA GGC GAG AAG ATT CGT GGG   585

                200                 205                 210
Thr Asp Glu Met Lys Phe Ile Thr Ile Leu Cys Thr Arg Ser Ala
ACT GAT GAG ATG AAA TTC ATC ACC ATC CTG TGC ACG CGC AGT GCC   630

                215                 220                 225
Thr His Leu Leu Arg Val Phe Glu Glu Tyr Glu Lys Ile Ala Asn
ACT CAC CTG CTG AGA GTG TTT GAA GAG TAT GAG AAA ATT GCC AAC   675

                230                 235                 240
Lys Ser Ile Glu Asp Ser Ile Lys Ser Glu Thr His Gly Ser Leu
AAG AGC ATT GAG GAC AGC ATC AAG AGT GAG ACC CAT GGC TCA CTG   720
```

FIG. 13c

```
                245                     250                     255
Glu Glu Ala Met Leu Thr Val Val Lys Cys Thr Gln Asn Leu His
GAG GAG GCC ATG CTC ACT GTG GTG AAA TGC ACC CAA AAC CTC CAC   765

                260                     265                     270
Ser Tyr Phe Ala Glu Arg Leu Tyr Tyr Ala Met Lys Gly Ala Gly
AGC TAC TTT GCA GAG AGA CTC TAC TAT GCC ATG AAG GGA GCA GGG   810

                275                     280                     285
Thr Arg Asp Gly Thr Leu Ile Arg Asn Ile Val Ser Arg Ser Glu
ACG CGT GAT GGG ACC CTG ATA AGA AAC ATC GTT TCA AGG AGC GAG   855

                290                     295                     300
Ile Asp Leu Asn Leu Ile Lys Cys His Phe Lys Lys Met Tyr Gly
ATT GAC TTA AAT CTT ATC AAA TGT CAC TTC AAG AAG ATG TAC GGC   900

                305                     310                     315
Lys Thr Leu Ser Ser Met Ile Met Glu Asp Thr Ser Gly Asp Tyr
AAG ACC CTC AGC AGC ATG ATC ATG GAA GAC ACC AGC GGC GAC TAC   945

                320                     325
Lys Asn Ala Leu Leu Ser Leu Val Gly Ser Asp Pro  *
AAG AAC GCC CTG CTG AGC CTG GTG GGC AGC GAC CCC TGA GGCACAG   991
```

FIG. 13d

AAGAACAAGAGCAAAGACCATGAAGCCAGAGTCTCCAGGACTCCTCACTCAACCTCGGC 1050

CATGGACGCAGGTTGGGTGTGAGGGGGGTCCCAGCCTTTCGGTCTTCTATTTCCCTATT 1109

TCCAGTGCTTTCCAGCCGGGTTTCTGACCCAGAGGTGGAACCGGCCTGGACTCCTCTTC 1168

CCAACTTCCTCCAGGTCATTTCCCAGTGTGAGCACAATGCCAACCTTAGTGTTTCTCCA 1227

GCCAGACAGATGCCTCAGCATGAAGGGCTTGGGGACTTGTGGATCATTCCTTCCTCCCT 1286

GCAGGAGCTTCCCAAGCTGGTCACAGAGTCTCCTGGGCACAGGTTATACAGACCCCAGC 1345

CCCATTCCCATCTACTGAAACAGGGTCTCCACAAGAGGGGCCAGGGAATATGGGTTTTT 1404

AACAAGCGTCTTACAAAACACTTCTCTATCATGCAGCCGGAGAGCTGGCTGGGAGCCCT 1463

TTTGTTTTAGAACACACATCCTTCAGCAGCTGAGAAATGAACACGAATCCATCCCAACC 1522

GAGATGCCATTAACATTCATCTAAAAATGTTAGGCTCTAAATGGACGAAAAATTCTCTC 1581

GCCATCTTAATAACAAAATAAACTACAAATTCCTGACCCAAGGACACTGTGTTATAAGA 1640

GGCGTGGGCTCCCCTGGTGGCTGACCAGGTCAGCTGCCCTGGCCTTGCACCCCTCTGCA 1699

TGCAGCACAGAAGGGTGTGACCATGCCCTCAGCACCACTCTTGTCCCCACTGAACGGCA 1758

ACTGAGACTGGGTACCTGGAGATTCTGAAGTGCCTTTGCTGTGGTTTTCAAAATAATAA 1817

AGATTTGTATTCAACTC-polyA 1834

FIG. 13e

```
                                                MAWWKAWIEQEGVTVKSSSHFNPDP

DAETLYKAMKG-IGTNEQAIIDVLTKRSNTQRQQIAKSFKAQFGKDLTETLKSELSGKFERLIVALMY   PPYRY

EAKELHDAMKG-LGTKEGVIIEILASRTKNQLREIMKAYEEDYGSSLEEDIQADTSGYLERILVCLLQ   GSRDDVSSFVDPALALQ

DAQDLYAAGEKIRGTDEMKFITILCTRSATHLLRVFEEYEKIANKSIEDSIKSETHGSLEEAMLTVVK   CTQNLHSY

FAERLYYAMKG-AGTRDGTLIRNIVSRSEIDLNLIKCHFKKMYGKTLSSMIMEDTSGDYKNALLSLVG   SDP*

       KG-hGTDExxLIpILApR                                     oooooo

dAe LY AMKG  GT Eg ll lL sRS tql.  I k ykk yGKsLee IkseTSG lEralv Lvk
                                       fe              d        l

     "Consensus":         x :  50% of amino acids identical
                          X :  75% of amino acids identical
                          X : 100% of amino acids identical

      "oooooo" :          Hydrophobic region
```

FIG. 14

| | VAC-alpha | | VAC-beta | |
|---|---|---|---|---|
| Ala | 26 | ( 8.1%) | 25 | ( 7.7%) |
| Cys | 1 | ( 0.3%) | 4 | ( 1.2%) |
| Asp | 25 | ( 7.8%) | 20 | ( 6.1%) |
| Asn | 6 | ( 1.9%) | 9 | ( 2.8%) |
| Glu | 29 | ( 9.1%) | 29 | ( 8.9%) |
| Gln | 12 | ( 3.8%) | 12 | ( 3.7%) |
| Phe | 13 | ( 4.1%) | 9 | ( 2.8%) |
| Gly | 22 | ( 6.9%) | 20 | ( 6.1%) |
| His | 3 | ( 0.9%) | 6 | ( 1.8%) |
| Ile | 18 | ( 5.6%) | 23 | ( 7.0%) |
| Lys | 22 | ( 6.9%) | 27 | ( 8.3%) |
| Leu | 38 | (11.9%) | 33 | (10.1%) |
| Met | 8 | ( 2.5%) | 11 | ( 3.4%) |
| Pro | 5 | ( 1.6%) | 6 | ( 1.8%) |
| Arg | 19 | ( 5.9%) | 15 | ( 4.6%) |
| Ser | 21 | ( 6.6%) | 27 | ( 8.3%) |
| Thr | 23 | ( 7.2%) | 21 | ( 6.4%) |
| Val | 16 | ( 5.0%) | 13 | ( 4.0%) |
| Trp | 1 | ( 0.3%) | 3 | ( 0.9%) |
| Tyr | 12 | ( 3.8%) | 14 | ( 4.3%) |
| | MW = 35896 | | MW = 36837 | |
| charged: | 98 | (30.6%) | 97 | (29.6%) |

FIG. 15

```
alpha                                 MAQVLRGTVTDFPGFDERA
 beta                             MAWWKAWIEQEGV..KSSSH.NPDP

alpha DAETLRKAMKGLGTDEESILTLLTSRSNAQRQEISAAFKTLFGRDLLDDLKSELTGKFEKLIVALMK   PSRLY
 beta .....Y.....I..N.QA.IDV..K...T...Q.AKS..AQ..K..TET.....S....R......Y   .PYR.

alpha DAYELKHALKGAGTNEKVLTEIIASRTPEELRAIKQVYEEEYGSSLEDDVVGDTSGYYQRMLVVLLQ   ANRDPDAG-IDEAQVEQ
 beta E.K..HD.M..L..K.G.II..L....KNQ..E.MKA...D......E.IQA.....LE.I..C...   GS..DVSSFV.P.LAL.

alpha DAQALFQAGELKWGTDEEKFITIFGTRSVSHLRKVFDKYMTISGFQIEETIDRETSGNLEQLLLAVVK   SIRSIPAY
 beta ...D.YA...KIR....M.....LC...AT..LR..EE.EK.ANKS..DS.KS..H.S..EAM.T...   CTQNLHS.

alpha LAETLYYAMKGAGTDDHTLIRVMVSRSEIDLFNIRKEFRKNFATSLYSMIKGDTSGDYKKALLLLCG   EDD*
 beta F..R.........R.G....NI........NL.KCH.K.MYGKT.S...ME.......N...S.V.   S.P*
```

FIG. 17

```
VA                     ATGGCACAGGTTCTCAGAGGCACTGTGACTGACTTCCCTGGA   42
VB   ATGGCCTGGTGGAAAGCCTG.ATTG.ACAGGAGG.T.T...A....AGAG.AG.T.CCAC   60

VA   TTTGATGAGCGGGCTGATGCAGAAACTCTTCGGAAGGCTATGAAAGGCTTGGGCACAGAT  102
VB   ..CA.CCCAGACC..........G..C..CTAC..A..C.....G..GA.C..G..CA.C  120

VA   GAGGAGAGCATCCTGACTCTGTTGACATCCCGAAGTAATGCTCAGCGCCAGGAAATCTCT  162
VB   ...C..GCT...A.CGA.G..C.C..CAAGA....C..CA.G.....G...C.G...G.C  180

VA   GCAGCTTTTAAGACTCTGTTTGGCAGGGATCTTCTGGATGACCTGAAATCAGAACTAACT  222
VB   AAGT.C..C...G...A...C....A...C..CACT..G.C.T....G..T..G..C.G.  240

VA   GGAAAATTTGAAAAATTAATTGTGGCTCTGATGAAACCCTCTCGGCTTTATGATGCTTAT  282
VB   ..C..G.....G.GGC.C........C..T...T.T..GC.ATACAGA..C..A..CA.G  300

VA   GAACTGAAACATGCCTTGAAGGGAGCTGGAACAAATGAAAAAGTACTGACAGAAATTATT  342
VB   ..G...C.TG.C...A.......CTTA.....C..G..GGGT..CA.C.TT..G..CC.G  360

VA   GCTTCAAGGACACCTGAAGAACTGAGAGCCATCAAACAAGTTTATGAAGAAGAATATGGC  402
VB   ..C..TC....CAAGA.CC.G...C.G.AG..A.TGA.G.CG.....G.....C.....G  420
```

FIG. 18a

```
VA   TCAAGCCTGGAAGATGACGTGGTGGGGGACACTTCAGGGTACTACCAGCGGATGTTGGTG   462
VB   ..C........G..G...A.CCAA.CA.....AAGT..C...CTGG..A....CC.....   480

VA   GTTCTCCTTCAGGCTAACAGAGACCCTGATGCTGGAATTGATGAAGCTCAAGTTGAACAA   522
VB   TGC.....G....GC.G...G..TGA..TGAGCA.CT...TG..CCCGGC.C.G.CC.TC   540

VA   GATGCTCAGGCTTTATTTCAGGCTGGAGAACTTAAATGGGGGACAGATGAAGAAAAGTTT   582
VB   C.A.ACGCACAGGATC.GT.T..G.C..GCGAG..GATTC.TGGGAC...T..G.T.AAA   600

VA   ATCACCATCTTTGGAACACGAAGTGTGTCTCATTTGAG...AAAGGTGTTTGACAAGTAC   639
VB   T...T..C.A.CCTGTGCACGC.CAGTG.CAC.CACCTGCTG.GA........AG....T   660
```

FIG. 18b

```
VA   ATGACTATATCAGGATTTCAAATTGAGGAAACCATTGACCGCGAGACTTCTGGCAATTTA   699
VB   GA..AA..TG.CAACAAGAGC........C.G...CA.GA.T.....CCA....TCAC.G   720

VA   GAGCAACTACTCCTTGCTGTTGTGAAATCTATTCGAAGTATACCTGCCTACCTTGCAGAG   759
VB   ...G.GGCCA.G..CA....G.......GC.CC.A..ACC.C.ACAG....T........   780

VA   ACCCTCTATTATGCTATGAAGGGAGCTGGGACAGATGATCATACCCTCATCAGAGTCATG   819
VB   .GA.....C....CC...........A.....GCG....GGG.....G..A...AA...C   840

VA   GTTTCCAGGAGTGAGATTGATCTGTTTAACATCAGGAAGGAGTTTAGGAAGAATTTTGCC   879
VB   .....A.....C........CT.AAA.CTT....AATGTC.C..C.A.....TG.AC.G.   900

VA   ACCTCTCTTTATTCCATGATTAAGGGAGATACATCTGGGGACTATAAGAAAGCTCTTCTG   939
VB   .AGA.C..CAGCAG......C.T..A...C..CAGC..C.....C.....C..C..G...   960

VA   CTGCTCTGTGGAGAAGATGAC                                          960
VB   AGC..GGTG..CAGC..CCC.                                          981
```

FIG. 18c

VA MAQVLRGTVTDFPGFDERA
VB MAWWKAWIEQEGVTVKSSSHFNPDP
LCI MAMVSEFLKQAWFIENEEQEYVQTVKSSKGGPGSAVSPYPTFNPSS
LCII MSTVHEILCKLSLEGDHSTPPSAYGSVKPYTNFDAER

VA DAETLRKAMKGLGTDEESILTLLTSRSNAQRQEISAAFKTLFGRDLLDDLKSELTGKFEKLIVALMK PSRLY
VB DAETLYKAMKGIGTNEQAIIDVLTKRSNTQRQQIAKSFKAQFGKDLTETLKSELSGKFERLIVALMY PPYRY
LCI DVAALHKAIMVKGVDEATIIDILTKRNNAQRQQIKAAYLQETGKPLDETLKKALTGHLEEVVLALLK TPAQF
LCII DALNIETAVKTKGVDEVTIVNILTNRSNVQRQDIAFAYQRRTKKELPSALKSALSGHLETVILGLLK TPAQY

VA DAYELKHALKGAGTNEKVLTEIIASRTPEELRAIKQVYEEEYGSSLEDDVVGDTSGYYQRMLVVLLQ ANRDPDAG-IDEAQVEQ
VB EAKELHDAMKGLGTKEGVIIEILASRTKNQLREIMKAYEEDYGSSLEEDIQADTSGYLERILVCLLQ GSRDDVSSFVDPALALQ
LCI DADELRAAMKGLGTDEDTLIEILASRTNKEIRDINRVYREELKRDLAKDITSDTSGDFRNALLSLAK GDRSEDFGVNED-LADS
LCII DASELKASMKGLGTDEDSLIEIICSRTNQELQEINRVYKEMYKTDLEKDIISDTSGDFRKLMVALAK GRRAEDGSVIDYELIDQ

VA DAQALFQAGELKWGTDEEKFITIFGTRSVSHLRKVFDKYMTISGFQIEETIDRETSGNLEQLLLAVVK SIRSIPAY
VB DAQDLYAAGEKIRGTDEMKFITILCTRSATHLLRVFEEYEKIANKSIEDSIKSETHGSLEEAMLTVVK CTQNLHSY
LCI DARALYEAGERRKGTDVNVFNTILTTRSYPQLRRVFQKYTKYSKHDMNKVLDLELKGDIEKCLTAIVK CATSKPAF
LCII DARELYDAGVKRKGTDVPKWISIMTERSVCHLQKVFERYKSYSPYDMLESIKKEVKGDLENAFLNLVQ CIQNKPLY

VA LAETLYYAMKGAGTDDHTLIRVMVSRSEIDLFNIRKEFRKNFATSLYSMIKGDTSGDYKKALLLLCG EDD*
VB FAERLYYAMKGAGTRDGTLIRNIVSRSEIDLNLIKCHFKKMYGKTLSSMIMEDTSGDYKNALLSLVG SDP*
LCI FAEKLHQAMKGVGTRHKALIRIMVSRSEIDMNDIKAFYQKMYGISLCQAILDETKGDYEKILVALCG GN*
LCII FADRLYDSMKGKGTRDKVLIRIMVSRSEVDMLKIRSEFKRKYGKSLYYYIQQDTKGDYQKALLYLCG GDD*

VA : human VAC-alpha
VB : human VAC-beta
LCI : human Lipocortin I
LCII: human Lipocortin II

FIG. 20

```
        10        20        30        40        50        60
AATTGGAGATTATCGTCACTGCAATGCTTCGCAATATGGCGCAAAATGACCAACAGCGGT
    CCTCTAATAGCAGTGACGTTACGAAGCGTTATACCGCGTTTTACTGGTTGTCGCCA

        70        80        90       100       110       120
TGATTGATCAGGTAGAGGGGGCGCTGTACGAGGTAAAGCCCGATGCCAGCATTCCTGACG
ACTAACTAGTCCATCTCCCCCGCGACATGCTCCATTTCGGGCTACGGTCGTAAGGACTGC

       130       140       150       160       170       180
ACGATACGGAGCTGCTGCGCGATTACGTAAAGAAGTTATTGAAGCATCCTCGTCAGTAAA
TGCTATGCCTCGACGACGCGCTAATGCATTTCTTCAATAACTTCGTAGGAGCAGTCATTT

       190       200       210       220       230       240
AAGTTAATCTTTTCAACAGCTGTCATAAAGTTGTCACGGCCGAGACTTATAGTCGCTTTG
TTCAATTAGAAAAGTTGTCGACAGTATTTCAACAGTGCCGGCTCTGAATATCAGCGAAAC

       250       260       270       280       290       300
TTTTTATTTTTTAATGTATTTGCTCGAGAGGTTGAGGTGATTTTATGAGCTCGAATTCAT
AAAAATAAAAAATTACATAAACGAGCTCTCCAACTCCACTAAAATACTCGAGCTTAAGTA
                      XhoI       RBS          SacI   EcoRI C

       310       320       330       340       350
CGATAAGCTTGGATCCGTCGACCGCGCCCGGCAGTGAATTTTCGCTGCCGGGTGGTTTTT
GCTATTCGAACCTAGGCAGCTGGCGCGGGCCGTCACTTAAAAGCGACGGCCCACCAAAAA
laI HindIIIBamHI SalI

       360       370
TTGCTGC
AACGACGAGCT
```

FIG. 21

Coomassie – Blue

FIG. 49a

SAMPLE : 3 vacb
RUN NUMBER : 22
PROTEIN : VAC 'beta'
CHROMATOGRAM OF : 21. 04. 88 3:17:36
INJECTION VOLUME : 50 µl
STANDARD VALUE : Averages of Run 22

| Name | Actual [in nMol] | Nominal | Rel. actual [ I ] | Rel. actual [ II ] | Rel. nominal |
|---|---|---|---|---|---|
| ASP | 14.07 | 29 | 29.59 | 6.35 | 7.25 |
| THR | 11.15 | 21 | 23.45 | 5.03 | 5.25 |
| SER | 12.34 | 27 | 25.96 | 5.57 | 6.75 |
| GLU | 19.97 | 41 | 41.99 | 9.01 | 10.25 |
| PRO | 5.38 | 6 | 11.31 | 2.43 | 1.50 |
| GLY | 11.94 | 20 | 25.12 | 5.39 | 5.00 |
| ALA | 12.19 | 25 | 25.63 | 5.50 | 6.25 |
| CYS | 2.22 | 4 | 4.66 | 1.00 | 1.00 |
| VAL | 5.86 | 13 | 12.32 | 2.64 | 3.25 |
| MET | 4.61 | 10 | 9.69 | 2.08 | 2.50 |
| ILE | 9.79 | 23 | 20.58 | 4.41 | 5.75 |
| LEU | 15.69 | 33 | 33.00 | 7.08 | 8.25 |
| TYR | 6.55 | 14 | 13.77 | 2.95 | 3.50 |
| PHE | 4.40 | 9 | 9.25 | 1.98 | 2.25 |
| HIS | 2.75 | 6 | 5.79 | 1.24 | 1.50 |
| LYS | 12.56 | 27 | 26.42 | 5.66 | 6.75 |
| NH3 | 18.43 | 0 | 38.77 | 8.31 | 0.00 |
| ARG | 7.23 | 15 | 15.20 | 3.26 | 3.75 |

| Name | Nominal | Corr actual | Rounded actual | Deviation | % Deviation |
|---|---|---|---|---|---|
| ASP | 29 | 29.23 | 29 | + 0.225 | 0.777 |
| THR | 21 | 23.16 | 23 | + 2.159 | 10.283 |
| SER | 27 | 25.64 | 26 | - 1.361 | 5.042 |
| GLU | 41 | 41.48 | 41 | + 0.478 | 1.167 |
| PRO | 6 | 11.17 | 11 | + 5.174 | 86.238 |
| GLY | 20 | 24.81 | 25 | + 4.806 | 24.032 |
| ALA | 25 | 25.31 | 25 | + 0.315 | 1.260 |
| CYS | 4 | 4.61 | 5 | + 0.606 | 15.150 |
| VAL | 13 | 12.17 | 12 | - 0.828 | 6.366 |
| MET | 10 | 9.57 | 10 | - 0.426 | 4.256 |
| ILE | 23 | 20.33 | 20 | - 2.674 | 11.626 |
| LEU | 33 | 32.59 | 33 | - 0.406 | 1.229 |
| TYR | 14 | 13.60 | 14 | - 0.401 | 2.862 |
| PHE | 9 | 9.13 | 9 | + 0.132 | 1.472 |
| HIS | 6 | 5.72 | 6 | - 0.285 | 4.748 |
| LYS | 27 | 26.09 | 26 | - 0.908 | 3.363 |
| NH3 | 0 | 38.29 | 0 | 0.000 | 0.000 |
| ARG | 15 | 15.01 | 15 | + 0.014 | 0.093 |

AS - Nom. value := 323
AS - Actual value := 330
Total deviation := 21.20 AS / 6.56%
Average amount protein := 0.510 nanoMol
ALA/LEU - Protein amount := 0.482 nanoMol

FIG. 49a continued

| Peak Name | Ret time | Area | Height | Type | Amount | RF |
|---|---|---|---|---|---|---|
| ASP | 7.67 | 12949108 | 589326 | ** | 10.797 | 1.1993e+06 |
| THR | 9.13 | 9054415 | 359489 | ** | 7.982 | 1.1344e+06 |
| SER | 9.67 | 13162093 | 508590 | ** | 9.327 | 1.4112e+06 |
| GLU | 12.20 | 21594486 | 581113 | ** | 15.972 | 1.3520e+06 |
| PRO | 13.73 | 1915825 | 42433 | ** | 4.469 | 4.2872e+05 |
| GLY | 16.80 | 12516849 | 365363 | ** | 9.017 | 1.3882e+06 |
| ALA | 18.27 | 11691803 | 288180 | ** | 9.471 | 1.2345e+06 |
| CYS | 19.60 | 1605991 | 124559 | ** | 0.864 | 1.8584e+06 |
| VAL | 20.13 | 5326578 | 424585 | ** | 4.445 | 1.1982e+06 |
| MET | 20.93 | 4866785 | 296576 | ** | 3.498 | 1.3911e+06 |
| ILE | 22.47 | 9170982 | 414630 | ** | 7.277 | 1.2603e+06 |
| LEU | 23.07 | 16274567 | 687357 | ** | 11.841 | 1.3744e+06 |
| TYR | 24.60 | 6190710 | 195610 | BB | 4.916 | 1.2593e+06 |
| PHE | 26.33 | 4001320 | 114100 | BB | 3.306 | 1.2105e+06 |
| HIS | 39.53 | 3146100 | 178088 | BB | 2.111 | 1.4904e+06 |
| LYS | 42.73 | 16208683 | 845200 | BB | 9.546 | 1.6980e+06 |
| NH3 | 46.93 | 13233695 | 414891 | BB | 10.856 | 1.2190e+06 |
| ARG | 51.87 | 6455633 | 155589 | BB | 5.202 | 1.2409e+06 |

FIG. 49b continued

| SEQUENCER PROGRAM: 3PAPTH | Degradation steps: 1 + 3P | PTH-AS-HPLC up to degradation step No. 3P | PTH-AS detectable up to degradation step No. 3P |
|---|---|---|---|

36μg [N/nmol] SAMPLE DISSOLVED IN 75 μl Ø.1%₀TFA ; 3 x 25μl AM APPLIED TO SEQUENCER

SEQUENCE:

| | | 1 | 2 | 3 | 4 | 5 | 6 | 7 | 8 | 9 | 10 |
|---|---|---|---|---|---|---|---|---|---|---|---|
| AS: 1-10 | I. | $X_{ALA}$[1)] | TRP | TRP | LYS | $X_{ALA}$[1)] | TRP | ILE | (GLU)[2)] | GLN | (GLU)[2)] |
| AS: 11-20 | I. | GLY | VAL | THR | VAL | LYS | SER | SER | SER | HIS[3)] | (PHE) |
| AS: 21-3Ø | I. | ASN | PRO | (ASP)[4)] | PRO | (ASP) | $X_{ALA}$[1)] | $X_{GLU}$ | THR | LEU | TYR |
| AS: 31-4Ø | I. | LYS | $X_{ALA}$[1)] | MET | (LYS) | GLY | ILE | GLY | (THR) | ASN | |

1) PTH-ALA detection perturbed by DMPTU (up to 12000000 IV(AS8) ≙ nmol PTH-AS

2) Retention times shifted from 1.P5' to 2.45'

3) ———— " ———— 5.50' to 4.80'

4) ———— " ———— 1.66' to 1.87'

[SEQUENCER DEFECT!]

FIG. 50a

ESTIMATION OF QUANTITIES

| Component | Amino acid from | to | Quantity [nmol] | Proportion [%] |
|---|---|---|---|---|
| I | 1 | (3P) | ~Ø.45 | / |
| II | | | | |
| III | | | | |
| IV | | | | |
| V | | | | |
| VI | | | | |
| VII | | | | |
| VIII | | | | |

Total quantity: ~Ø.45nmol
(Calculated from ILE7-8, 80% R.Y.)

Compare with: 124Ø

FIG.50a continued pH-Range: 3.5-9.5
Manuf of plates: LKB-PAG plate
Electrode Solutions: Anode 1 M Phosphoric acid
Cathode 1 M Sodium hydroxide
Running time: Prefocussing 500 Vh
Focussing 3000 Vh — IEF-Marker
— 22 μg VAC β-4
— 11 μg VAC β-4
— 18 μg VAC β-4 + DTT
— 9 μg VAC β-4 + DTT
— IEF-Marker VAC β-4 : 1. Main band pI 5.35
2. Main band pI 5.45 + DTT

COMPOSITION COMPRISING AN ANTICOAGULANT

This application is a continuation of application Ser. No. 07/552,198, filed Jul. 13, 1990, now abandoned.

FIELD OF THE INVENTION

The present invention is in the field of medicinal chemistry. In particular, the present invention relates to pharmaceutical compositions which contain bivalent cations in addition to an anticoagulant or an analog thereof and the use thereof to treat or prevent thrombosis or embolism.

BACKGROUND OF THE INVENTION

The blood coagulation mechanism takes the form of a cascade of enzymatic reactions at the end of which comes the formation of thrombin which finally converts fibrinogen into fibrin. Various procoagulant reactions such as, for example, the activation of prothrombin by factors Xa and Va are catalyzed by phospholipid surfaces to which the coagulation factors bind. Not every kind of phospholipid is capable of stimulating coagulation. The charging of the phospholipid surface appears to determine the extent of the effect. Negatively charged phospholipids such as phosphatidyl serine have a high procoagulatory effect.

Among the proteins which bind to phospholipids and interfere with processes dependent on phospholipid surfaces, there is a category which are dependent on $Ca^{2+}$ in their binding to phospholipids. This category of proteins, which are also known as the annexines, includes not only lipocortin I, calpactin I, protein II, lipocortin III, p67-calelectrin but also the vascular anticoagulant protein (VAC) and IBC, PAP, PAPI, PP4, endonexin II and lipocortin V.

The structural features common to all the annexines are presumably the basis for their similar $Ca^{2+}$ and phospholipid binding properties. Although this general property is true of all annexines, there is clear individuality in their affinity for $Ca^{2+}$ and the various types of phospholipid.

The physiological functions of the annexines are concerned with membrane-associated processes. The fundamental mechanism of the coagulation-inhibiting effect of VAC was recognized as an inhibition of the catalytic capacity of phospholipids caused by the binding of VAC to their surfaces, thereby preventing the formation of the coagulation-promoting complex on the surface thereof.

Other annexines are also capable of inhibiting coagulation, but VAC appears to be the most effective inhibitor.

The aim of the present invention was to provide a VAC preparation which is more effective than pure VAC.

SUMMARY OF THE INVENTION

The present invention is directed to pharmaceutical compositions comprising a vascular anticoagulant annexine and at least one bivalent cation selected from the group comprising $Ca^{2+}$, $Cd^{2+}$, $Zn^{2+}$, $Mn^{2+}$ or $Co^{2+}$ and optionally excipients, carriers and/or stabilizers.

In particular, the present invention is related to pharmaceutical compositions wherein the vascular anticoagulant annexine has the Formula (I):

(I)

| | | | | | | | | | | | | | | |
|---|---|---|---|---|---|---|---|---|---|---|---|---|---|---|
| 1 | | | | 5 | | | | | 10 | | | | | 15 |
| X | Ala | Gln | Val | Leu | Arg | Gly | Thr | Val | Thr | Asp | Phe | Pro | Gly | Phe |
| | | | | 20 | | | | | 25 | | | | | 30 |
| Asp | Glu | Arg | Ala | Asp | Ala | XX | Thr | Leu | Arg | Lys | Ala | Met | Lys | Gly |
| | | | | 35 | | | | | 40 | | | | | 45 |
| Leu | Gly | Thr | Asp | Glu | Glu | Ser | Ile | Leu | Thr | Leu | Leu | Thr | Ser | Arg |
| | | | | 50 | | | | | 55 | | | | | 60 |
| Ser | Asn | Ala | Gln | Arg | Gln | Glu | Ile | Ser | Ala | Ala | Phe | Lys | Thr | Leu |
| | | | | 65 | | | | | 70 | | | | | 75 |
| Phe | Gly | Arg | Asp | Leu | Leu | Asp | Asp | Leu | Lys | Ser | Glu | Leu | Thr | Gly |
| | | | | 80 | | | | | 85 | | | | | 90 |
| Lys | Phe | Glu | Lys | Leu | Ile | Val | Ala | Leu | Met | Lys | Pro | Ser | Arg | Leu |
| | | | | 95 | | | | | 100 | | | | | 105 |
| Tyr | Asp | Ala | Tyr | Glu | Leu | Lys | His | Ala | Leu | Lys | Gly | Ala | Gly | Thr |
| | | | | 110 | | | | | 115 | | | | | 120 |
| Asn | Glu | Lys | Val | Leu | Thr | Glu | Ile | Ile | Ala | Ser | Arg | Thr | Pro | Glu |
| | | | | 125 | | | | | 130 | | | | | 135 |
| Glu | Leu | Arg | Ala | Ile | Lys | Gln | Val | Tyr | Glu | Glu | Glu | Tyr | Gly | Ser |
| | | | | 140 | | | | | 145 | | | | | 150 |
| Ser | Leu | Glu | Asp | Asp | Val | Val | Gly | Asp | Thr | Ser | Gly | Tyr | Tyr | Gln |
| | | | | 155 | | | | | 160 | | | | | 165 |
| Arg | Met | Leu | Val | Val | Leu | Leu | Gln | Ala | Asn | Arg | Asp | Pro | Asp | Ala |
| | | | | 170 | | | | | 175 | | | | | 180 |
| Gly | Ile | Asp | Glu | Ala | Gln | Val | Glu | Gln | Asp | Ala | Gln | Ala | Leu | Phe |
| | | | | 185 | | | | | 190 | | | | | 195 |
| Gln | Ala | Gly | Glu | Leu | Lys | Trp | Gly | Thr | Asp | Glu | Glu | Lys | Phe | Ile |
| | | | | 200 | | | | | 205 | | | | | 210 |
| Thr | Ile | Phe | Gly | Thr | Arg | Ser | Val | Ser | His | Leu | Arg | Lys | Val | Phe |
| | | | | 215 | | | | | 220 | | | | | 225 |
| Asp | Lys | Tyr | Met | Thr | Ile | Ser | Gly | Phe | Gln | Ile | Glu | Glu | Thr | Ile |
| | | | | 230 | | | | | 235 | | | | | 240 |
| Asp | Arg | Glu | Thr | Ser | Gly | Asn | Leu | Glu | Gln | Leu | Leu | Leu | Ala | Val |
| | | | | 245 | | | | | 250 | | | | | 255 |
| Val | Lys | Ser | Ile | Arg | Ser | Ile | Pro | Ala | Tyr | Leu | Ala | Glu | Thr | Leu |
| | | | | 260 | | | | | 265 | | | | | 270 |
| Tyr | Tyr | Ala | Met | Lys | Gly | Ala | Gly | Thr | Asp | Asp | His | Thr | Leu | Ile |
| | | | | 275 | | | | | 280 | | | | | 285 |
| Arg | Val | Met | Val | Ser | Arg | Ser | Glu | Ile | Asp | Leu | Phe | Asn | Ile | Arg |
| | | | | 290 | | | | | 295 | | | | | 300 |

-continued

| | | | | | | | | | | | | | | |
|---|---|---|---|---|---|---|---|---|---|---|---|---|---|---|
| Lys | Glu | Phe | Arg | Lys | Asn | Phe | Ala | Thr | Ser | Leu | Tyr | Srr | Met | Ile |
| | | | | 305 | | | | | 310 | | | | | 315 |
| Lys | Gly | Asp | Thr | Ser | Gly | Asp | Tyr | Lys | Lys | Ala | Leu | Leu | Leu | Leu |
| | | | | 320 | | | | | | | | | | |
| Cys | Gly | Glu | Asp | Asp | * | | | | | | | | | |

wherein X represents a hydrogen, a methionine or a blocking group on the alanine at position 2, and XX represents Glu or Asp, or a variant or derivative thereof having anticoagulant properties.

The present invention also relates to pharmaceutical compositions wherein the vascular anticoagulant annexine has the Formula (II):

(II)

| | | | | | | | | | | | | | | |
|---|---|---|---|---|---|---|---|---|---|---|---|---|---|---|
| 1 | | | | 5 | | | | | 10 | | | | | 15 |
| X | Ala | Trp | Trp | Lys | Ala | Trp | Ile | Glu | Gln | Glu | Gly | Val | Thr | Val |
| | | | | 20 | | | | | 25 | | | | | 30 |
| Lys | Ser | Ser | Ser | His | Phe | Asn | Pro | Asp | Pro | Asp | Ala | Glu | Thr | Leu |
| | | | | 35 | | | | | 40 | | | | | 45 |
| Tyr | Lys | Ala | Met | Lys | Gly | Ile | Gly | Thr | Asn | Glu | Gln | Ala | Ile | Ile |
| | | | | 50 | | | | | 55 | | | | | 60 |
| Asp | Val | Leu | Thr | Lys | Arg | Ser | Asn | Thr | Gln | Arg | Gln | Gln | Ile | Ala |
| | | | | 65 | | | | | 70 | | | | | 75 |
| Lys | Ser | Phe | Lys | Ala | Gln | Phe | Gly | Lys | Asp | Leu | Thr | Glu | Thr | Leu |
| | | | | 80 | | | | | 85 | | | | | 90 |
| Lys | Ser | Glu | Leu | Ser | Gly | Lys | Phe | Glu | Arg | Leu | Ile | Val | Ala | Leu |
| | | | | 95 | | | | | 100 | | | | | 105 |
| Met | Tyr | Pro | Pro | Tyr | Arg | Tyr | Glu | Ala | Lys | Glu | Leu | His | Asp | Ala |
| | | | | 110 | | | | | 115 | | | | | 120 |
| Met | Lys | Gly | Leu | Gly | Thr | Lys | Glu | Gly | Val | Ile | Ile | Glu | Ile | Leu |
| | | | | 125 | | | | | 130 | | | | | 135 |
| Ala | Ser | Arg | Thr | Lys | Asn | Gln | Leu | Arg | Glu | Ile | Met | Lys | Ala | Tyr |
| | | | | 140 | | | | | 145 | | | | | 150 |
| Glu | Glu | Asp | Tyr | Gly | Ser | Ser | Leu | Glu | Glu | Asp | Ile | Gln | Ala | Asp |
| | | | | 155 | | | | | 160 | | | | | 165 |
| Thr | Ser | Gly | Tyr | Leu | Glu | Arg | Ile | Leu | Val | Cys | Leu | Leu | Gln | Gly |
| | | | | 170 | | | | | 175 | | | | | 180 |
| Ser | Arg | Asp | Asp | Val | Ser | Ser | Phe | Val | Asp | Pro | Ala | Leu | Ala | Leu |
| | | | | 185 | | | | | 190 | | | | | 195 |
| Gln | Asp | Ala | Gln | Asp | Leu | Tyr | Ala | Ala | Gly | Glu | Lys | Ile | Arg | Gly |
| | | | | 200 | | | | | 205 | | | | | 210 |
| Thr | Asp | Glu | Met | Lys | Phe | Ile | Thr | Ile | Leu | Cys | Thr | Arg | Ser | Ala |
| | | | | 215 | | | | | 220 | | | | | 225 |
| Thr | His | Leu | Leu | Arg | Val | Phe | Glu | Glu | Tyr | Glu | Lys | Ile | Ala | Asn |
| | | | | 230 | | | | | 235 | | | | | 240 |
| Lys | Ser | Ile | Glu | Asp | Ser | Ile | Lys | Ser | Glu | Thr | His | Gly | Ser | Leu |
| | | | | 245 | | | | | 250 | | | | | 255 |
| Glu | Glu | Ala | Met | Leu | Thr | Val | Val | Lys | Cys | Thr | Gln | Asn | Leu | His |
| | | | | 260 | | | | | 265 | | | | | 270 |
| Ser | Tyr | Phe | Ala | Glu | Arg | Leu | Tyr | Tyr | Ala | Met | Lys | Gly | Ala | Gly |
| | | | | 275 | | | | | 280 | | | | | 285 |
| Thr | Arg | Asp | Gly | Thr | Leu | Ile | Arg | Asn | Ile | Val | Ser | Arg | Ser | Glu |
| | | | | 290 | | | | | 295 | | | | | 300 |
| Ile | Asp | Leu | Asn | Leu | Ile | Lys | Cys | His | Phe | Lys | Lys | Met | Tyr | Gly |
| | | | | 305 | | | | | 310 | | | | | 315 |
| Lys | Thr | Leu | Ser | Ser | Met | Ile | Met | Glu | Asp | Thr | Ser | Gly | Asp | Tyr |
| | | | | 320 | | | | | 325 | | | | | |
| Lys | Asn | Ala | Leu | Leu | Ser | Leu | Val | Gly | Ser | Asp | Pro | * | | |

wherein X represents a hydrogen, a methionine or a blocking group on the alanine at position 2; or a variant or derivative thereof having anticoagulant properties.

The invention also relates to pharmaceutical compositions comprising aggregated annexines and at least one bivalent cation, wherein at least two annexines are linked by at least one disulfide bridge between the cysteine groups.

The invention also relates to a process for preparing the pharmaceutical compositions according to the invention, comprising mixing an annexine with at least one bivalent cation selected from the group comprising $Ca^{2+}$, $Cd^{2+}$, $Zn^{2+}$, $Mn^{2+}$ or $Co^{2+}$, and optionally with an excipient, carrier, and/or stabilizer, and, optionally, freeze-drying.

The invention also relates to a method for the treatment or prevention of thrombosis or enbolism in an animal susceptible to thrombosis or enbolism, comprising administering to the animal a vascular anticoagulant annexine and at least one bivalent cation selected from the group comprising $Ca^{2+}$, $Cd^{2+}$, $Zn^{2+}$, $Mn^{2+}$ or $Co^{2+}$. The annexine and bivalent cation may be administered substantially simultaneously or sequentially, so long as the combination of the annexine and bivalent cations produce their intended effect. Preferably, the annexine and bivalent cation are administered simultaneously as part of a pharmaceutical composition which may comprise excipients, carriers and/or stabilizers.

The invention also relates to the use of the pharmaceutical compositions of the present invention for medical uses outside the body, for example, for the stabilization of stored blood.

DESCRIPTION OF THE FIGURES

FIG. 1 depicts the tryptic fragments from placenta VAC.

FIG. 7 depicts the screening of oligonucleotides EBI-386, 387 and 388.

FIG. 8 depicts the screening oligonucleotides EBI-118 and 119.

FIGS. 10a, 10b, 10c, 10d and 10e depict the VAC-alpha cDNA sequence.

FIGS. 11a, 11b and 11c depict the arrangement of the peptide sequences in the VAC-alpha cDNA derived amino acid sequence.

FIG. 12 depicts the subsequence repreated four times in VAC-alpha protein.

FIGS. 13a, 13b, 13c, 13d and 13e depict the VAC-beta cDNA sequence.

FIG. 14 depicts the subsequence repeated four times in VAC-beta protein.

FIG. 15 depicts the amino acid composition of VAC-alpha and VAC-beta.

FIG. 17 depicts the amino acid comparison of VAC-alpha with VAC-beta.

FIGS. 18a, 18b and 18c depict nucleotide comparisons between VAC-alpha and beta cDNA, respectively.

FIG. 20 depicts a comparison of VAC-alpha, VAC-beta, lipocortin I and lipocortin II.

FIG. 21 depicts the sequence of RH284.

FIGS. 49a and 49b depict the amino acid analysis of recombinant VAC-β.

FIG. 50a depicts the N-terminal sequencing of recombinant VAC-β.

○100% DOPS; •20% DOPS; Δ5% DOPS; □1% DOPS; 100% DOPC; all the mixtures were supplemented with DOPC. [VAC]=1 μg/ml.

Figure 55:
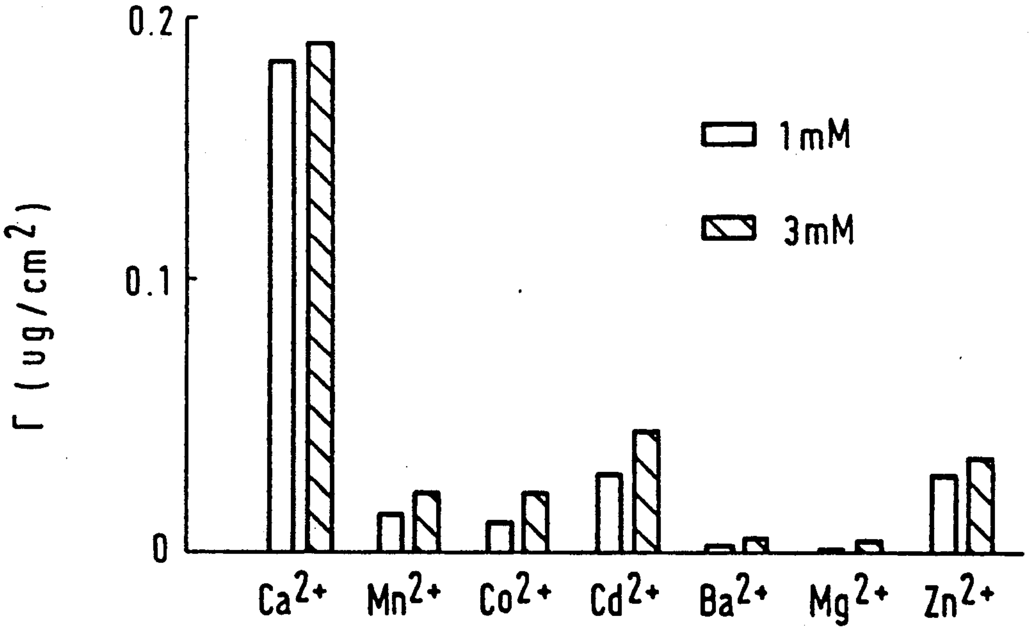

FIG. 55 depicts the effect of bivalent ions on the adsorption of VAC. VAC adsorption on double layers of 20% DOPS and 80% DOPC in the presence of the ions specified (1 or 3 mM). [VAC]=1 μg/ml.

Figure 56:
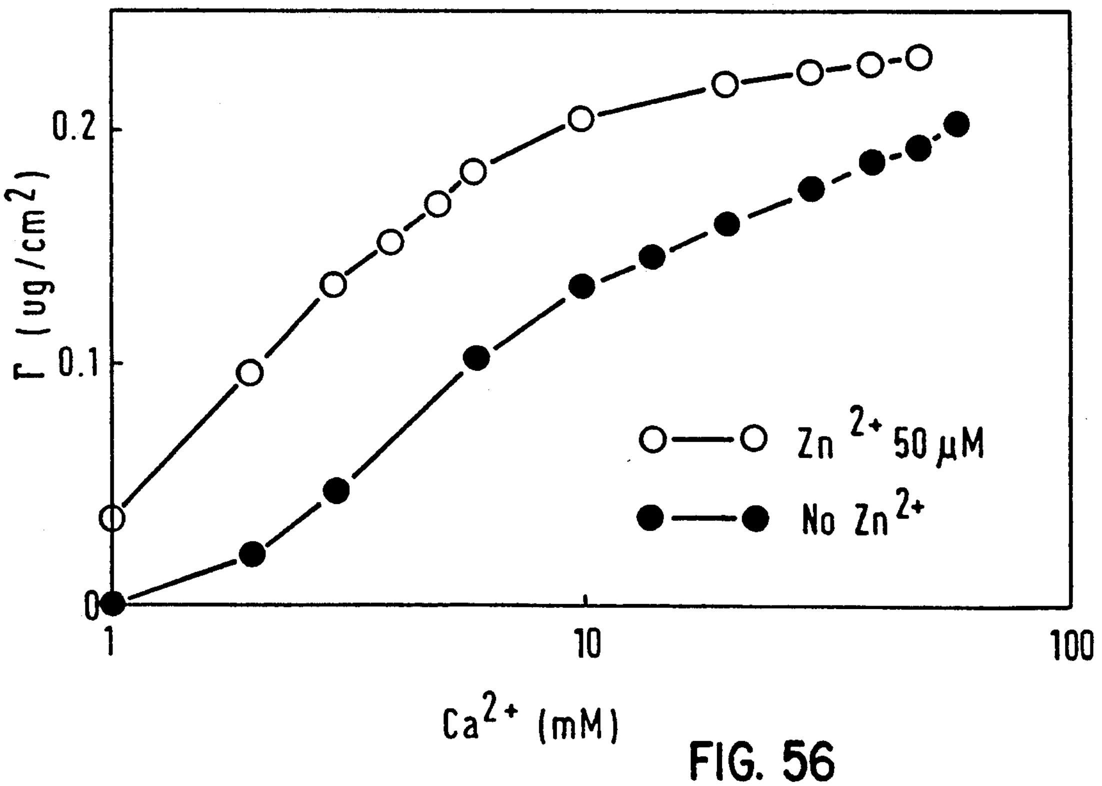

FIG. 56 depicts the synergistic effect of $Zn^{2+}$ on the $Ca^{2+}$-dependent adsorption of VAC on the phospholipid surface. The effect of $Ca^{2+}$ on the VAC adsorption on 1% DOPS and 99% DOPC in the presence of 50 μM $Zn^{2+}$ was measured. [VAC]=1 μg/ml.

DESCRIPTION OF THE PREFERRED EMBODIMENTS

Binding studies have shown that VAC associates reversibly with procoagulatory phospholipids in calcium-dependent manner.

Other bivalent cations from the series comprising $Cd^{2+}$, $Zn^{2+}$, $Mn^{2+}$ and $Co^{2+}$ also have a positive effect on association, but not to the same extent as $Ca^{2+}$.

The present invention therefore relates to pharmaceutical compositions which contain a vascular anticoagulant comprising an annexine whether naturally occurring or synthetically produced or genetically engineered and derivatives or analogs thereof and at least one bivalent cation selected from the group consisting $Ca^{2+}$, $Cd^{2+}$, $Zn^{2+}$, $Mn^{2+}$ or $Co^{2+}$ and optionally excipients and/or carriers and/or stabilizers. The preparation of such annexines and derivatives and analogs thereof is taught, for example, in EPA 0 181 465 and EPA 0 293 567 as follows.

The proteins with VAC activity may be prepared by genetic engineering. This was achieved by clarifying the amino acid sequence of parts of the proteins with VAC activity which are isolated from strongly vascularized tissue and highly purified (EPA 0 181 465), preparing synthetic DNA probes using these sequences and investigating cDNA libraries therewith. After isolation of cDNA hybridizing with the probes, sequence determination and suitable manipulation, this cDNA was expressed in suitable host systems, for example in bacteria, yeast or mammalian cells.

One of the purified proteins was enzymatically cleaved with trypsin. The peptides formed were separated and selected fragments were sequenced. However, the sequence of the N-terminus defied direct analysis since the first amino acid is obviously blocked.

The sequence information is given in FIG. 1.

A suitable DNA probe can be produced basically by three methods. If a fairly long section of the protein, roughly 30 or more amino acids long, is known, it is possible to establish a fairly probable sequence for the corresponding mRNA section, taking into account the codons preferably used in mammals. A probe of this kind is, in the worst instance, about 66% homologous with the actual sequence. This is the reason why the probe has to be relatively long so as to be able to hybridize under non-stringent conditions.

The second possibility is to synthesize all the conceivable variations of oligonucleotides for a short peptide section, roughly six to seven amino acids long. If such complex mixtures are used in the investigation of cDNA libraries, a relatively large number of "false" positive-reacting clones may be isolated. Furthermore, the hybridization signal may be very weak, since the single oligonucleotide which fits perfectly will make up only a small part of the total mixture.

The third method admittedly does not get around the variability of an oligonucleotide probe but, by the choice of a special nucleoside triphosphate (NTP) it does ensure that all the molecules of the probe can bind to the cDNA sought (or also to "false" cDNA). Thus, oligonucleotides 23 bases long corresponding to the tryptic peptide [P30/I] have been synthesized using inosine triphosphate.

VAC proteins may be isolated from strongly vascularized tissue. The ideal tissues are umbilical cord vessels or placenta. Therefore, and since it is known that almost all genes are expressed in the placenta, by contrast with other special tissues, the above-mentioned DNA probes were used to investigate a placental cDNA library which had been prepared from placental tissue in a manner known per se, to search for cDNA molecules which code for VAC proteins.

In order to search the cDNA library for cDNA which codes for VAC protein, two oligonucleotides were synthesized corresponding to the sequences of tryptic peptide P16/II and one oligonucleotide was synthesized for the sequences of Staph A peptide P20/I/6 (FIG. 7). These oligonucleotides are each mixtures of all the variants which take into accound every coding possibility of the corresponding mRNA. EBI-386 has 512 variations with a chain length of 20 nucleotides and fits the Staph-A-peptide P20/I/6. In order to keep the variation lower in the oligonucleotide for the tryptic peptide p16/II, two oligonucleotides (20-mers) were synthesized: EBI-387: 128 variations and EBI-388: 64 variations.

Furthermore, two oligonucleotides were synthesized corresponding to the tryptic VAC peptide P30/I, using desoxyinosine as the base in "wobble" positions (FIG. 8): EBI-118 and EBI-119. This substitution has been described by Ohtsuka et al., *J. Biol. Chem.* 260/5 (1985), pp. 2605–2608, and by Takahashi et al., *Proc. Nat. Acad. Sci.* (1985) pp. 1931–1935. Inosine base-pairs well with cytosine, but hardly interferes with the formation of the double helix when other nucleotides are offered as partners.

After each of these oligonucleotides had been radioactively labelled in known manner, extracts from phage plates were hybridized therewith by known methods.

Hybridization with EBI-386, 387 and 388 produced the phages lambda-P11/3, lambda-P6/5 and lambda-P6/6. Hybridization with EBI-118 and 119 resulted in the phages lambde-Nr15, lambda-Nr19 and lambda-Nr22.

The DNAs isolated from the phages were cut with EcoRI and the fragments produced were isolated.

The cDNA inserts of the clones lambda-P11/3, lambda-P6/5 and lambda-P6/6 had sizes of approximately 1300 to 1400 bp. The sequence analysis showed that all three clones were derived from one and the same mRNA. However, the 5' end of the mRNA was missing in the cDNAs. The inserts of the phages lambda-Nr15, lambda-NR19 and lambda-Nr22 had lengths of approximately 1600, 1100 and 1000 bp. Sequence analysis indicated an approximately complete cDNA.

The cDNAs of the two phase groups lambda-P11/3, lambda-P6/5 and lambda-P6/6 and lambda-Nr15, lambda-Nr19 and lambda-Nr22 are derived from two different mRNAs, as was shown by the sequence analysis. The EcoRI inserts of the three clones lambda-P11/3, lambda-P6/5 and lambda-P6/6 were isolated and ligated into the EcoRi-cut Bluescribe M13+ vector (Vector Cloning Systems, 3770 Tansy Street, San Diego, Calif. 92121, USA). The resulting clons were designated pP6/5, pP6/6 and pP11/3.

The EcoRI inserts of the three clones lambda-Nr15, lambda-Nr19 and lambda-Nr22 were isolated and ligated into the EcoRi-cut Bluescribe M13+ vector. The resulting clones were designated pRH201, pRH202 and pRH203.

In order to obtain other cDNA clones, the human placental lambda-gt10 library was investigated once more, this time with the radioactively labelled EcoRI insert of pP11/3 as the probe.

In all, 69 positively-reacting clones were obtained (lambda-VAC1 to lambda-VAC69).

12 of these clones were prepared on a small scale as described above, the cDNA inserts were freed with EcoRI and isolated. It was found that the insert of the clone lambda-VAC10 contains the entire reading frame coding for VAC protein. In order to characterize the cDNAs which code for VAC-alpha and VAC-beta, a Northern blot equipment, sequence analyses and a genomic Southern blot analysis were carried out.

Figure 2:
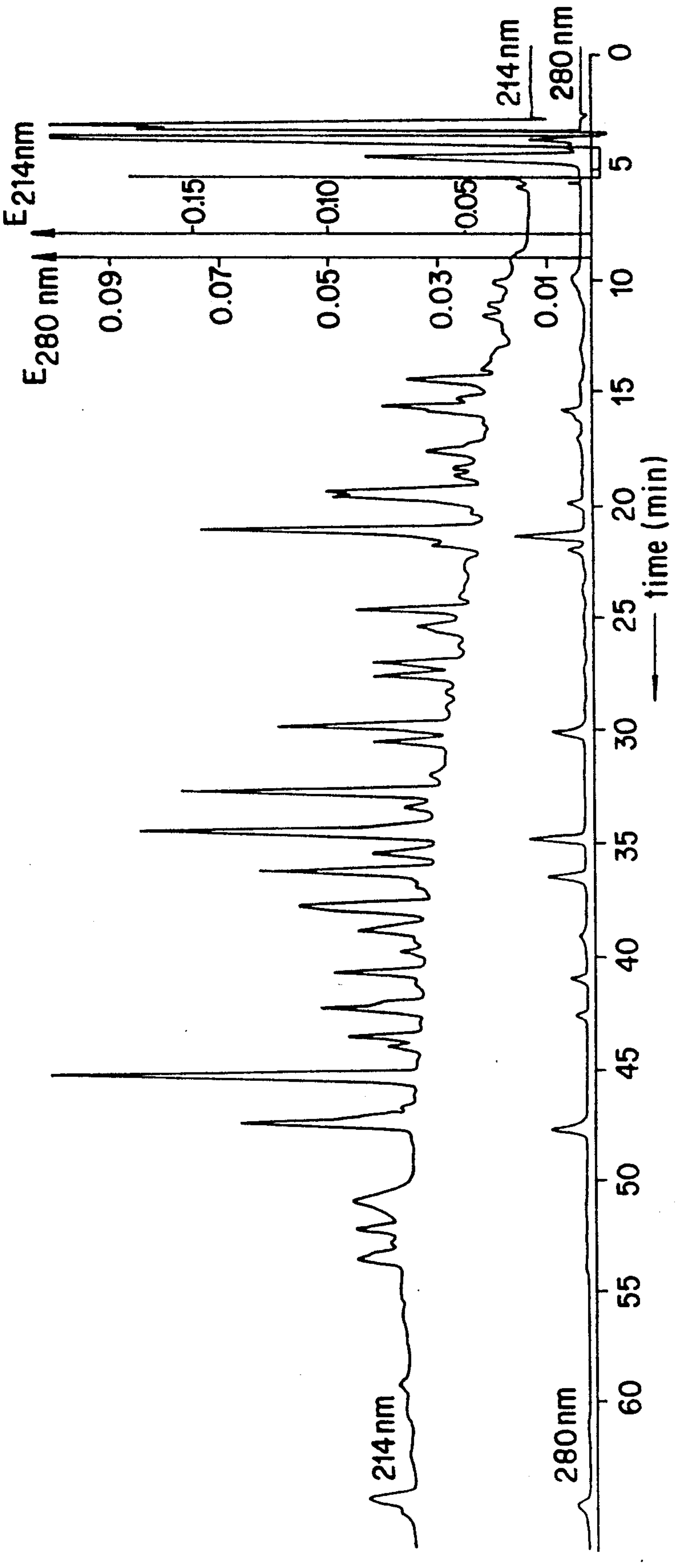
FIG. 2 depicts an HPLC of the tryptic peptides from placenta-VAC.
Figure 3:
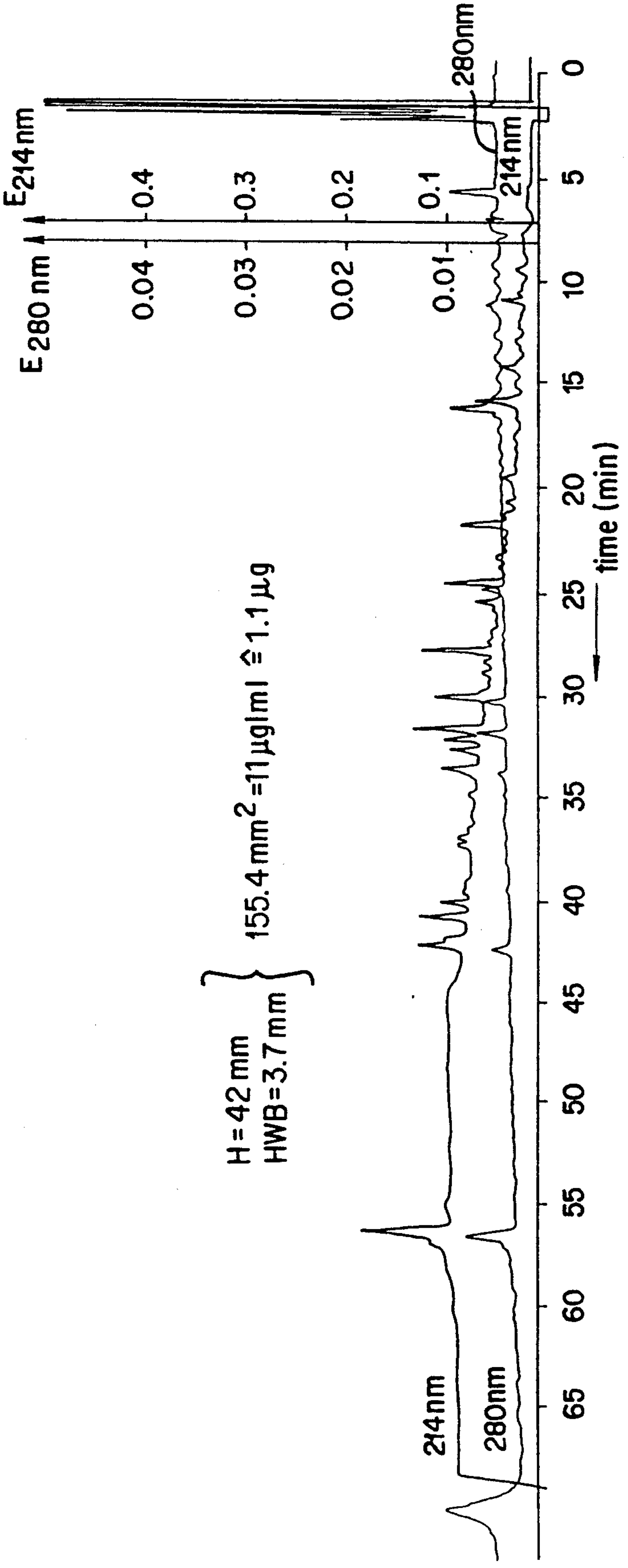
FIG. 3 depicts an HPLC of the tryptic peptides from umbilical cord VAC.
Figure 4A:
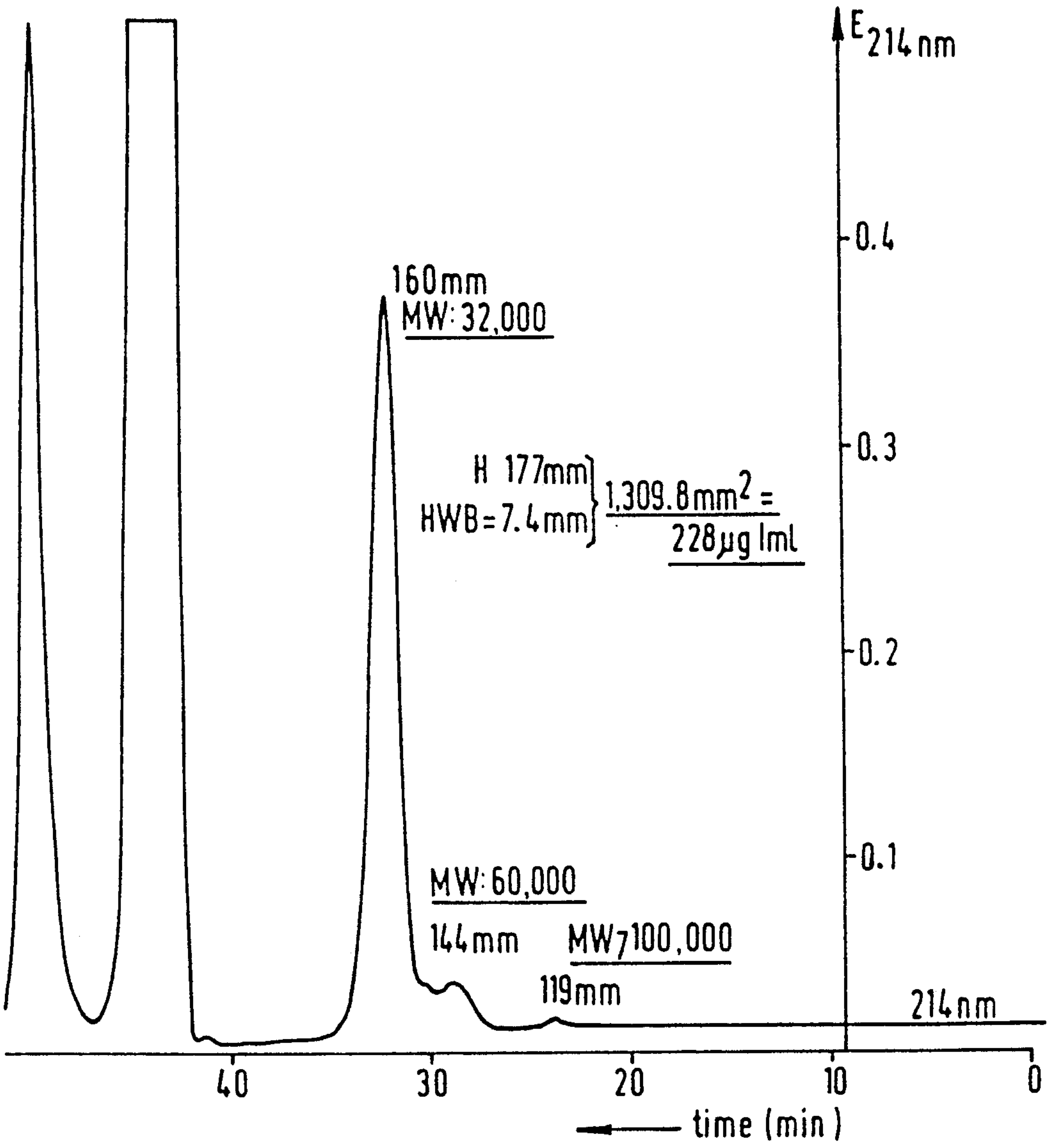
FIG. 4a depicts a gel permeation HPLC of placenta VAC.
Figure 4B:
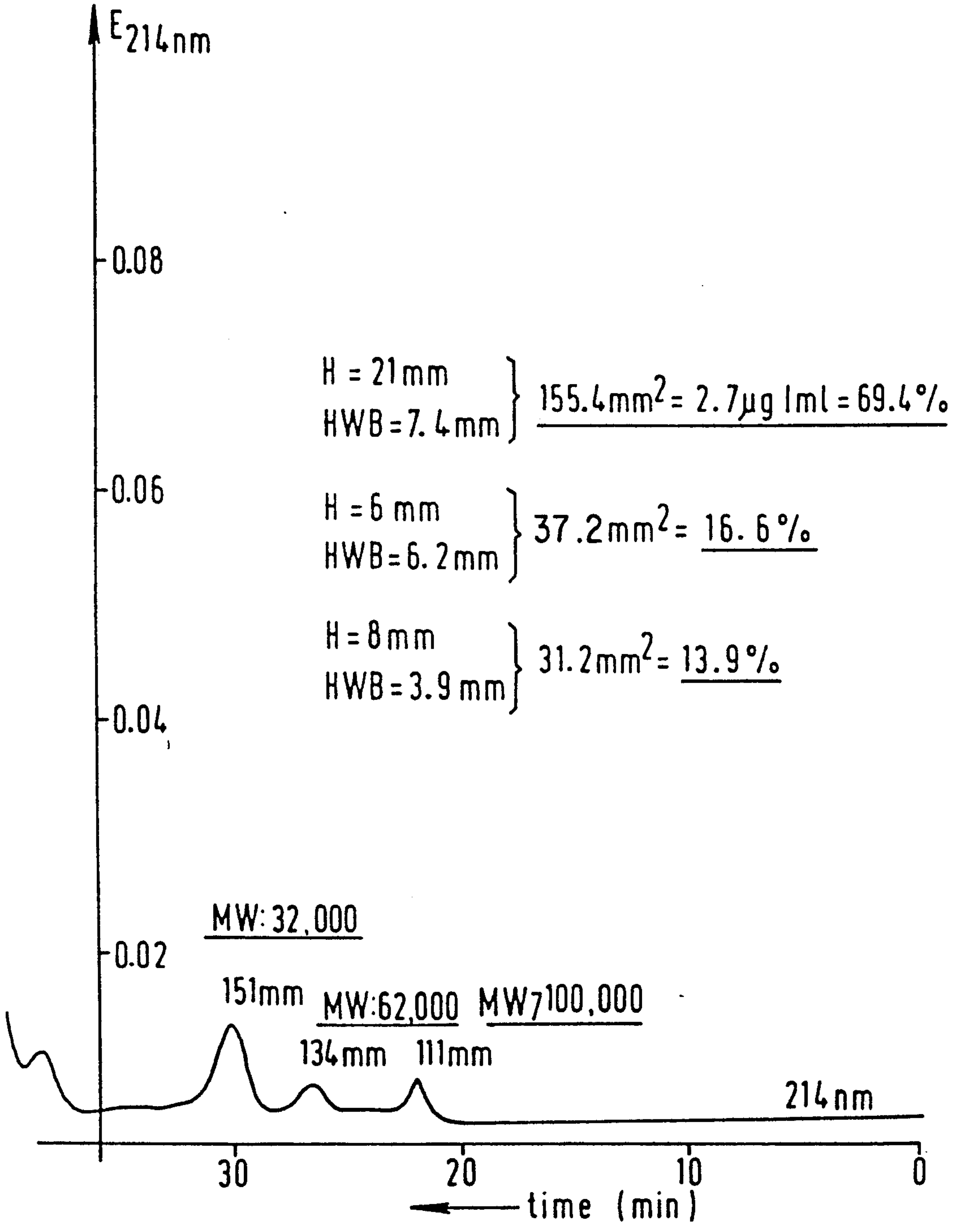
FIG. 4b depicts a gel permeation HPLC of umbilical cord VAC.
Figure 5:
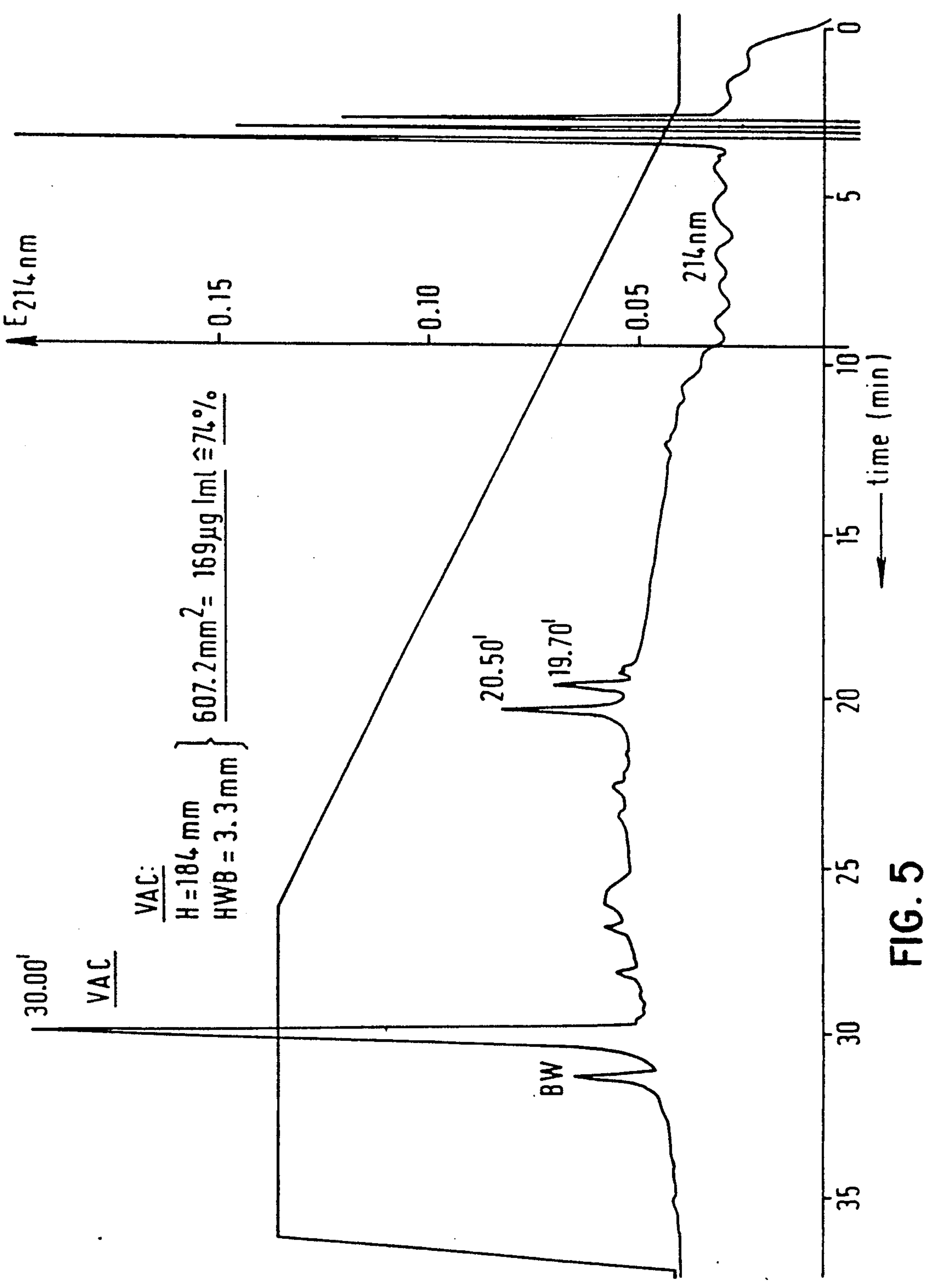
FIG. 5 depicts a reverse phase HPLC of placenta-VAC.
Figure 6:
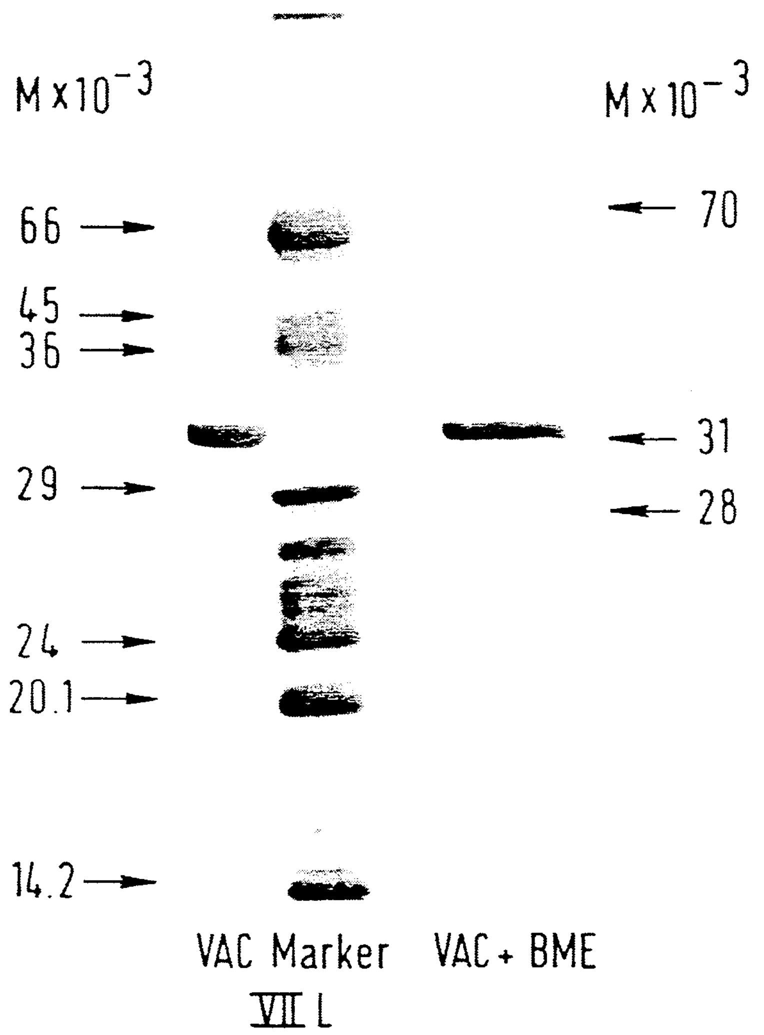
FIG. 6 depicts an SDS gel electrophoresis of placenta VAC.
Figure 9A:
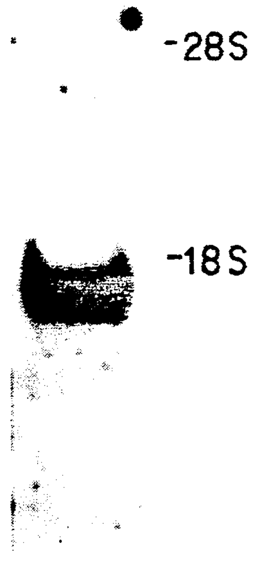
FIGS. 9a and 9b depict Northern blot analysis with VAC-alpha and VAC-beta cDNA.
Figure 9B:
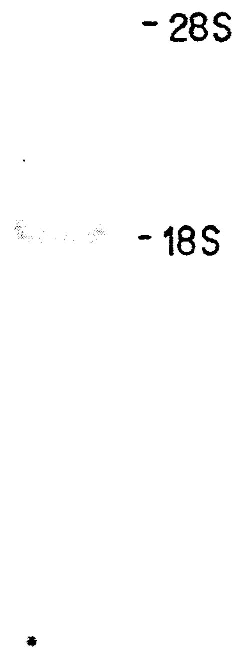

The results are shown in FIGS. 9*a* and 9*b*. The cDNA of the clone pP11/3 hybridizes to an mRNA approximately 1700 bases long ("VAC-alpha"), the cDNA of the clone pRH203 hybridizes to an mRNA approximately 2200 bases long ("VAC-beta").

Since, firstly, the quantity of radioactivity used and the amount of mRNA applied per trace were about the same and secondly the hybridization of a genome blot in the same solution yielded bands of the same intensity with both cDNAs (see below) it can be concluded that the shorter mRNA (VAC-alpha) is represented in larger quantities than the longer VAC-beta) mRNA in placenta.

For sequence analysis of the VAC-alpha cDNA, the cDNA of clones pP6/5, pP6/6 and pP11/3 was totally sequenced and that of the clones lambda-VAC1 to 12 was partially sequenced. The results are shown in FIGS. 10*a*, 10*b*, 10*c*, 10*d* and 10*e*. In all, 1465 bases were sequenced. The cDNA shows a long open reading frame which can code for 320 amino acids. If the DNA sequence is translated into an amino acid sequence, all the sequenced peptides of the tryptic fragments can be accommodated in this sequence (FIGS. 11*a*, 11*b* and 11*c*). Therefore, this cDNA is the one whose corresponding mRNA codes for VAC protein. Since the sequences of the second isolated cDNA code for a similar protein but one which is different from VAC, the name VAC-alpha is introduced here.

The first ATG codon (bases 35–37) is preceded in the same reading frame by a stop codon. The bases 30 to 38 satisfy the Kozak rule fairly well (M. Kozak, *Nature* 308:241–246 (1984)), which gives the consensus sequence near the translation start codon as CC(A/G)-CCAUGG; the corresponding sequence here it TCGCTATGG. The 3' non-translated region is 471 bases long. 15 bases before the start of the poly-A section is the polyadenylation sequence AATAAA (Proudfoot et al., *Nature* 263:211–214 (1976)). If the poly-A section of the mRNA is reckoned to have a chain length of 150 to 200 bases, the total length of the mRNA based on the cDNA sequence is 1600–1650 bases. Since a higher value was determined in the Northern blot experiment the 5' non-translated region is not completely contained in any cDNA.

Unlike all other cDNA clones, the cDNA of clone pP6/5 has C instead of A at position 100. As a result, the triplet 98–100 (22nd codon) would change from GAA to GAC and would code for Asp instead of Glu. This deviation may have a number of causes: a) the reverse transcriptase has incorporated a wrong nucleotide, b) these are the transcripts of two allelic genes which differ at this point or c) there are two non-allelic genes which differ at this position.

The long open reading frame codes for a protein with 320 amino acids, from which the Met-I is probably cleaved, and the following alanine is blocked at the amino group, possibly by acylation. The calculated molecular weight is 35,896 D and is higher than the value according to SDS-PAGE. Certainly, the proportion of charged amino acids (Asp, Glu, Lys, Arg, His) at 30.6% (99/320) is well above average compared with the average value of 25.1%. This would explain the different migration characteristics of the protein in the SDS-PAGE. Within the strongly charged amino acids, the acidic amino acids (Asp and Glu) are predominant, being 54 in number, compared with the base amino acids (Lys and Arg), of which there are 41. This explains the acidic isoelectric point of the VAC-alpha protein (pI=4.4 to 4.8). VAC-alpha contains only one triplet coding for cysteine (amino acid position 316); there is no typical N-glycosylation site (Asn-XXX-Ser/Thr).

Structural analysis of the amino acid sequence (modified according to Pustell et al., *Nucleic Acids Res.* 10:4765–4782 (1982)) yields a fourfold repetition of a 67 amino acid long sequence (FIG. 12), hereinafter referred to as "repeats". Within this sequence, 7 amino acids (10.4%) are kept in all four repeats, 15 amino acids (22.4%) occur in three of the four repeats, and at 28 positions (41.8%) two repeats each contain the same amino acid.

A comparison with published data (M.J. Geisow, *FEBS Letters* 203:99–103 (1986); Geisow et al., *TIBS* 11:420–423 (1986)) surprisingly showed that VAC-alpha thus belongs to a fairly large group of Ca++ dependent phospholipid binding proteins. A consensus sequenceisdescribed(Lys-Gly-fob-Gly-Thr-Asp-Glu-var-var-Leu-Ile-fil-Ile-Leu-Ala-fob-Arg; fob=hydrophobic, fil=hydrophilic, var=variable), which could be involved in the Ca++ binding (Geisow et al., *Nature* 320:636–638 (1986)). This sequence occurs in each of the four repeated 67 amino acid long subsequences of the proteins according to the invention (FIG. 12).

The 6 amino acid long section at the end of each repeat which consists almost exclusively of hydrophobic amino acids is also noticable ("oooooo" in FIG. 12).

Sequence analysis of the clones Nr15, Nr19 and Nr22 showed 1940 bp for the VAC-beta cDNA, which merges into a poly-A section (FIGS. 13*a*, 13*b*, 13*c*, 13*d* and 13*e*) 16 bases before the poly-A section is the polyadenylation signal AATAAA. Certainly, this consensus sequence occurs at the nucleotide position 1704–1709. The reason why this sequence is not used as a polyadenylation signal is not known. The sequence additionally required at the 3' end of the AATAAA sequence, YGTGTTYY (Gill et al., *Nature* 312:473–474 (1984)) does not occur until a relatively long way away (TGTGTTAT, positions 1735–1742); it is possible that this is the explanation for non-acceptance of this first polyadenylation sequence.

The cDNA contains a long open reading frame which extends from the beginning of the cDNA to position 1087. It would contain a coding potential for 362 amino acids. For reasons of analogy with VAC-alpha and owing to the fact that a 34,000 D protein also occurs during purification of VAC (see, E.P.A. 181,465) the first methionine codon (ATG, position 107–109) was taken as the start of translation. The Kozak rule is not satisfied so well here as in VAC-alpha (AAGAGATGG at position 102–110). The resulting protein (VAC-beta) is 327 amino acids long. It has 4 cysteine groups (amino acid positions 161, 206, 250 and 293) and a potential N-glycosylation site (Asn-Lys-Ser, amino acid position 225–227). The calculated molecular weight is 36,837 (FIG. 15). In VAC-beta, as well, there are a larger than average number of charged groups: 97/327 (29.6%), whilst the acid amino acids (Asp+Glu: 49) predominate over the basic amino acids (Lys+Arg 42): an explanation for the lower molecular weight determined according to SDS-PAGE.

VAC-beta also shows an internal repetition of a 67 amino acid long sequence (FIG. 14). Within this sequence 7 amino acids (10.4%) are kept in all four repeats, 17 amino acids (25.4%) occur in three of the four repeats, and at 25 positions (37.7%) two repeats each contain the same amino acid. VAC-beta also shows a high similarity with the 17 amino acid long consensus sequence. The remarks made concerning VAC-alpha apply similarly to VAC-beta.

FIGS. 18*a*, 18*b* and 18*c* show a comparison of the coding regions of VAC-alpha and VAC-beta cDNA. Surprisingly, the DNAs show a degree of homology of only 54.2%, i.e., somewhat less than the two proteins.

In many cases, for example for the expression of proteins, it is advantageous to precede the mature, desired protein/polypeptide by a signal sequence or by a protein sequence native to the host organism, so that a fusion protein is produced as an expression product. The signal sequence coding for a signal peptide may be of microbial origin or may come from mammalian cells; preferably, the signal peptide is homologous to the host organism. In order to be able to convert these products into the desired mature protein, a specific cleavage site is required between the signal/fusion part and the mature protein. For this purpose, an oligonucleotide which codes for the recognition tetrapeptide of the factor Xa protease, for example, may be inserted at this site as described above. As a result, the expressed fusion protein can be cleaved in controlled manner with the factor Xa protease. The mature protein is obtained.

If the codons responsible for methionine, apart from the one at amino acid position 1, are deliberately replaced by codons which code for leucine, isoleucine or valine, any immature or fusion protein which may be obtained can be converted into the mature protein by BrCN cleavage.

Any sequence which codes for a polypeptide with the spectrum of activity of the proteins according to the invention and which hybridizes with the sequences shown (or parts thereof) under stringent conditions (e.g., conditions which select for more than 85%, preferably more than 90% homology) is also included.

The hybridizations are carried out in 6×SSC/5×Denhardt's solution/0.1% SDS at 65° C. The degree of stringency is determined in the washing step. Thus, for selection of DNA sequences with approximately 85% or more homology, suitable conditions are 0.2×SSC/0.01% SDS/65° C. and for selection of DNA sequences with approximately 90% homology or more, the suitable conditions are 0.1×SSC/0.01% SDS/65° C.

The expression vectors may be prepared, for example, by introducing a VAC coding DNA sequence into a vector DNA which contains an expression control sequence in such a way that the expression control sequence regulates the said DNA sequence.

The choice of a suitable vector results from the particular host cell used for the transformation. Suitable hosts include, for example, microorganisms such as yeasts, e.g., *Saccharomyces cerevisiae*, and particularly bacterial strains which have no restriction or modification enzyme, especially strains of *Escherichia coli*, e.g., *e. coli* X1776, *E. coli* HB101, *E. coli* W3110, *E. coli* HB101/LM1035, *E. coli* JA221(30) or *E. coli* K12 strain 294, *Bacillus subtilis, Bacillus stearothermophilus,* Pseudomonas, Haemophilus, Streptococcus and others, also cells of higher organisms, particularly established human or animal cell lines. The preferred host cells are all the strains of *E. coli* particularly *E. coli* HB101, *E. coli* JM101 and *E. coli* W3110.

Theoretically, all vectors which replicate and express the heterologous DNA sequences coding for VAC in the host selected are suitable.

Examples of vectors which are suitable for the expression of the VAC gene in an *E. coli* strain are bacteriophages, e.g., derivatives of the bacteriophage λ, or plasmids, particularly the plasmid colE1 and the derivatives thereof, e.g., pMB9, pSF2124, pBR317 or pBR322. The preferred vectors are derived from plasmid pBR322. Suitable vectors contains a complete replicon and a labelling gene which makes it possible to select and identify the microorganisms transformed with the expression plasmids on the basis of a phenotypical feature. Suitable markings may give the microorganism resistance to heavy metals, antibiotics and the like, for example. Moreover, preferred vectors according to this invention contain, in addition to the replicon and labelling gene regions, recognition sequences for restriction endonucleases, so that at these points the DNA sequence coding for the amino acid sequence of VAC and optionally the expression control sequence can be inserted.

A preferred vector, the plasmid pBR322, contains an intact replicon, labelling genes (tet® and amp®) which give resistance to tetracycline and ampicillin and a number of unique recognition sequences for restriction endonucleases, e.g., PstI (cuts in the amp® gene, the tet® gene remains intact), BamHI, HindIII, SalI (all cut in the tet® gene whilst the amp® gene remains intact), NruI and EcoRI.

A number of expression control sequences may be used to regulate the VAC expression. In particular, expression control sequences of strongly expressed genes of the host cell which is to be transformed are used. In the case of pBR322 as the hybrid vector and *E. coli* as the host organism, for example, the expression control sequences (which contain inter alia the promoter and the ribosomal binding site) of the lactose operon, tryptophan operon, arabinose operon and the like, the β-lactamase gene, the corresponding sequence of the phage λN gene or the phage fd-layer protein gene and others are suitable. Whilst the promoter of the β-lactamase gene (β-lac gene) is already contained in the plasmid pBR322, the other expression control sequences must be introduced in the plasmid. The preferred expression control sequence in the present invention is that of the tryptophan operon (trp po) and that of *Serratia marcescens* and also of *E. coli* and the alkaline phosphatase promoter or the hybrid thereof.

In addition to these particularly common promoters, other microbial promoters have also been developed and used. The genetic sequence for the proteins according to the invention may, for example, be used under the control of the leftward promoter of the bacteriophage lambda ($P_L$). This promoter is a particularly effective controllable promoter. Control is made possible by the lambda repressor of which adjacent restriction cutting sites are known. A temperature-sensitive allele of this repressor gene may be inserted into a vector which contains a protein gene sequence. If the temperature is increased to 42° C., the repressor is inactivated and the promoter is activated. By using this system it is possible to establish a clone bank in which a functional protein gene sequence is placed close to a ribosome binding site at varying distances from the lambda $P_L$ promoter. These clones can then be checked and those with the highest yield selected.

The expression and translation of a sequence coding for the proteins according to the invention may also be effected under the control of other regulating systems which may be regarded as "homologous" to the organism in its untransformed form. Thus, for example, chromosomal DNA from a lactose-dependent *E. coli* contains a lactose or lac-operon which allows the degradation of lactose by secreting the enzyme beta-galactosidase.

The lac-control elements may be obtained from the bacteriophage lambda-plac5, which is infectious for *E. coli*. The lac-operon of the phage may be obtained from the same bacterial species by transduction. Regulating systems which may be used in the process according to the invention may originate from plasmid DNA which is native to the organism. The lac-promoter-operator system may be induced by IPTG.

Other promoter-operator systems or parts thereof may be used with equally good effect: for example, colicin $E_1$-operator, galactose operator, xylose-A operator, ta-promoter, etc.

In addition to prokaryotes, eukaryotic microorganisms such as yeast cultures may also be used. *Saccharomyces cerevisiae* is the most commonly used of the eukaryotic microorganisms, although a number of other species are generally obtainable.

Vectors suitable for replication and expression in yeast contain a yeast replication start and a selective genetic marker for yeast. Hybrid vectors which contain a yeast replication start, e.g., the chromosomal autonomically replicating segment (ars), are retained extrachromosomally after transformation within the yeast cell and are replicated autonomously during mitosis. For expression in Saccharomyces, for example the plasmid YRp7 (Stinchcomb et al., *Nature* 282:39 (1979)); (Kingsman et al., *Gene* 7:141 (1979)); Tschumper et al., *Gene* 10:157 (1980)) and the plasmid Yep13 (Bwach et al., *Gene* 8:121–133 (1979)) are conventionally used. The plasmid YRp7 contains the TRP1 gene which is a selectable marker for a yeast mutant which is incapable of growing in tryptophan-free medium; for example ATCC No. 44076.

The presence of the TRP1 defect as a characteristic of the yeast host genome constitutes an effective aid to detecting transformation, when cultivation is carried out without tryptophan. The situation is very similar with the plasmid YEp13, which contains the yeast gene LEU 2, which can be used to complement a LEU 2-minus mutant.

Other suitable marking genes for yeast are, in general, in the case of auxotrophic yeast mutants, genes which complement the host defects. Corresponding genes ensure prototrophy in an auxotrophic yeast mutant, e.g., the URA3 and HIS3 gene. Preferably, yeast hybrid vectors also contain a replication start and a marker gene for a bacterial host, particularly *E. coli*, so that the construction and cloning of the hybrid vectors and their precursors can take place in a bacterial host. Other expression control sequences which are suitable for expression in yeast include, for example, those of the PHO3 or PHO5 gene, and also promoters involved in glycolytic degradation, e.g., the PGK and GAPDH promoter.

Other suitable promoter sequences for yeast vectors contain the 5′-flanking region of ADH I (Ammerer G., *Methods of Enzymology* 101:192–201 (1983)), 3-phosphoglycerate kinase (Hitzeman et al., *J. Biol. Chem.* 255:2073 (1980)), or other glycolytic enzymes (Kawasaki and Fraenkel, *BBRC* 108:1107–1112 (1982)) such as enolase, glyceraldehyde-3-phosphate dehydrogenase, hexokinase, pyruvate decarboxylase, phoshofructokinase, glucose-6-phosphate isomerase and glucokinase. By constructing suitable expression plasmids the termination sequences associated with these genes may also be inserted into the expression vector at the 3′-end of the sequence which is to be expressed, on order to ensure polyadenylation and termination of the mRNA.

Other promoters which also have the advantage of transcription controlled by growth conditions are the promoter regions of the genes for alcohol dehydrogenase-2, isocytochrome C, acid phosphatase, degradation enzymes which are coupled to nitrogen metabolism, the above-mentioned glyceraldehyde-3-phosphate dehydrogenase and enzymes which are responsible for the processing of maltose and galactose. Promoters which are regulated by the yeast mating type locus, for example promoters of the genes BAR1, MFα1, STE2, STE3 and STE5, may be used in temperature-regulated systems by the use of temperature-dependent sir mutations (Rhine, Ph.D. Thesis, University of Oregon, Eugene, Oregon (1979), Herskowitz and Oshima, *The Molecular Biology of the Yeast Saccharomyces, Part I,* 181–209 (1981), Cold Spring Harbour Laboratory)). These mutations affect the expression of the resting mating type cassettes of yeasts and thus indirectly the mating type dependent promoters. Generally, however, any plasmid vector which contains a yeast-compatible promoter, original replication and termination sequences, is suitable.

Thus, it is also possible to use hybrid vectors which contain sequences homologous to the yeast 2μ plasmid DNA. Hybrid vectors of this kind are incorporated within the cell by recombination with existing 2μ plasmids or replicate autonomously. 2μ sequences are particularly suitable for plasmids with a high transformation frequency and permit a high copy number.

In addition to microorganisms, cell cultures of multicellular organisms are also suitable host organisms. In theory, any of these cultures may be used, whether obtained from vertebrate or invertebrate animal cultures. However, the greatest interest has been in vertebrate cells, with the result that the multiplication of vertebrate cells in culture (tissue culture) has become a routine method in recent years (*Tissue Culture*, Academic Press, Editors Kruse and Patterson, (1973)). Examples of useful host cell lines of this kind include VERO and HeLa cells, CHO cells and WI38, BHK, COS-7 and MDCK cell lines. Expression vectors for these cells generally contain (when necessary) a replication starting point, a promoter which is located in front of the gene to be expressed, together with any necessary ribosome binding site, RNA splicing site, polyadenylation site and transcriptional termination sequences.

When used in mammalian cells, the control functions in the expression vector are often obtained from viral material. For example, the promoters normally used originate from polyoma, adenovirus 2 and particularly frequently from Simian virus 40 (SV 40). The early and late promoters of SV 40 are particularly useful since both can be easily obtained from the virus as a fragment which also contains the viral replication site of the SV 40 (Fiers et al., *Nature* 273:113 (1978)). It is also possible to use smaller or larger fragments of SV 40, provided that they contain the sequence, approximately 250 bp long, which extends from the HindIII cutting site to the BglI cutting site in the viral replication site. Furthermore it is also possible and often desirable to use promoter or control sequences which are normally linked to the desired genetic sequences, provided that these control sequences are compatible with the host cell systems.

A replication starting point may either be provided by corresponding vector construction in order to incorporate na exogenic site, for example from SV 40 or other viral sources (e.g., polyoma, adeno, VSV, PBV, etc.) or it may be provided by the chromosomal replication mechanisms of the host cell. If the vector is integrated into the host cell chromosome, the latter measure is usually sufficient.

To achieve effective expression, the VAC gene must be arranged correctly ("in phase") with the expression control sequence. It is advantageous to link the expression control sequence in the region between the main mRNA start and the ATG of the gene coding sequence, which is naturally linked to the expression control sequence (e.g., the $\beta$-lac coding sequence if the $\beta$-lac promoter is used), to the VAC gene which preferably brings with it its own translation start signal (ATG) and translation stop signal (for example TAG). This ensures effective transcription and translation.

For example, a vector, particularly pBR322, is cut with a restriction endonuclease and, optionally after modification of the linearized vector thus formed, an expression control sequence provided with corresponding restriction ends is introduced. The expression control sequence contains at the 3' end (in the direction of translation) the recognition sequence of a restriction endonuclease, so that the vector which already contains the expression control sequence is digested with said restriction enzyme and the VAC gene provided with the corresponding ends can be used. A mixture of two hybrid plasmids is thus formed containing the gene in the right or wrong orientation. It is advantageous to cleave the vector which already contains the expression control sequence with a second restriction endonuclease within the vector DNA and to use the VAC gene provided with the right ends in the resulting vector fragment. All operations on the vector are preferably carried out so that the function of the replicon and of at least one marking gene are not affected.

In a preferred embodiment, a vector derived from pBR322, which contains an expression control sequence, particularly that of the tryptophan operon (trp po) and which carries at its 3' end (between the main mRNA start and the first ATG) the recognition sequence for a restriction endonuclease, e.g., EcoRl, which preferably forms cohesive ends, is digested with the above-mentioned restriction endonuclease and in the vector-DNA part with a second restriction endonuclease which forms flat or preferably cohesive ends, e.g., BamHI, after which the vector thus linearized is linked with the VAC-DNA having corresponding ends (e.g., with an EcoRI end before the ATG start and a BamHI end after the translation stop codon). Linking is effected in known manner by pairing the complementary (cohesive) ends and ligation, e.g., with $T_4$-DNA ligase.

Preferably, the DNA sequences may also be expressed in the expression plasmid pER103 (Rastl-Dworkin et al., *Gene* 21, 237-248 (1983) and EP-A-0115613 - deposited at the DSM under No. DSM 2773 on Dec. 20, 1983), in the plasmid parpER33 (EP-A-O115613) or the plasmid pRH100, since these vectors all contain regulatory elements which lead to a high expression rate for the cloned genes. According to the invention, the plasmid pRH100 which contains the regulatable tryptophan promoter from *Serratia marcescens* and an artificial ribosome binding site, is used as the expression vector for the synthetic protein gene. In order to prepare the expression plasmid pRH100, the pladmis pER103 (Dworkin-Rastl et al., *Gene* 21:237-248 (1983), EP-A-0115613) was linearized with the restriction endonuclease HindIII and the oligonucleotide sequence

```
5' AGCTTAAAGATGAGCTCATCTTTA      3'
3'      ATTTCTACTCGAGTAGAAATTCGA 5'
```

was inserted.

The VAC-DNA provided with corresponding (in particular EcoRl and BamHl) ends, obtained by the mRNA method, from genomic DNA or synthetically, can be cloned into a vector, e.g., pBR322, before being introduced into an expression plasmid, in order to obtain larger quantities of VAC-DNA, for example for sequence analysis. Isolation of the clones which contain the hybrid plasmid is carried out, for example, with a VAC-DNA specific, radioactively labelled oligonucleotide probe (see above). The VAC-DNA is characterized, for example, using the method of Maxam and Gilbert.

Suitable host cells are for example the above-mentioned microorganisms, such as strains of *Saccharomyces cerevisiae, Bacillus subtilis* and, in particular, *Escherichia coli*. Transformation with the expression plasmids according to the invention is effected, for example, as described in the literature, for *S. cerevisiae* (12), *B. subtilis* (13) and *E. coli* (14). The transformed host cells are advantageously isolated from a selective nutrient medium to which is added the biocide against which the marker gene contained in the expression plasmid gives resistance. If, as is preferred, the expression plasmids contain the amp ® gene, ampicillin is added to the nutrient medium accordingly. Cells which do not contain the expression plasmid are killed off in such a medium.

The invention also relates to the transformed host cells which can be obtained by the method described.

The transformed host cells can be used to prepare compounds with VAC activity. The process for preparing this compound is characterized in that the transformed host cells are cultivated and the produce is released from the host cells and isolated.

The process for preparing compounds with VAC activity and salts of such compounds is characterized in that host cells transformed with an expression plasmid which contains a DNA sequence coding for the amino acid sequence of VAC and regulated by an expression control sequence are cultivated in a liquid nutrient medium which contains assimilable carbon and nitrogen sources and the product is freed from the host cells and isolated and, if necessary, a product obtainable according to this process is mixed with a reducing agent suitable for breaking the disulphide bonds and the reduced polypeptide obtained is, if desired, treated with an oxidizing agent suitable for the fresh formation of disulphide bonds and, if desired, a VAC compound obtained is converted into another VAC compound, a mixture of compounds with VAC activity obtained by the process is separated into the individual components and/or, if desired, a salt obtained is converted into the polypeptide and a polypeptide obtained is converted into the corresponding salt thereof.

The transformed host cells according to the invention are cultivated in a manner known per se. Thus, various carbon sources may be used to cultivate the transformed host mocroorganisms according to the invention. Examples of preferred carbon sources include assimilable carbohydrates, such as glucose, maltose, mannitol or lactose, or an acetate which may be used either on its own or in suitable mixtures. Suitable nitrogen sources include, for example, amino acids such as casamino acids, peptides and proteins and the breakdown products thereof such as tryptone, peptone or meat extracts; also yeast extracts, malt extract, and also ammonium salts, e.g., ammonium chloride, sulphate or nitrate, which may be used either on their own or in suitable mixtures. Inorganic salts which may also be used, include for example sulphates, chlorides, phosphates and carbonats of sodium, potassium, magnesium and calcium.

The medium also contains, for example, growth promoting substances such as trace elements, e.g., iron, zinc, manganese and the like and preferably substances which exert a selection pressure and prevent the growth of cells which have lost the expression plasmid. Thus, for example, ampicillin is added to the medium if the expression plasmid contains an amp ® gene. The addition of antibiotically active substances in this way also ensures that any contaminating, antibiotic-sensitive microorganisms are killed off.

The conditions of cultivation, such as temperature, pH of the medium and fermentation time, are selected so as to obtain the maximum VAC titre. Thus, an *E. coli* or yeast strain is preferably cultivated nder aerobic conditions in a submerged culture with shaking or stirring at a temperature of about 20° to 40° C., preferably about 30° C., and at a pH of from 4 to 9, preferably at pH 7, for about 4 to 20 hours, preferably 8 to 12 hours. The expression product accumulates within the cells.

When the cell density has reached a sufficient level, the cultivation is stopped and if necessary the product is freed from the cells of the microorganism. For this purpose, the cells are destroyed, e.g., by treating with a detergent such as SDS or triton or lysed with lysozyme or an enzyme with a similar activity. Alternatively or additionally, mechanical forces such as shear forces (e.g., an X press, French press or Dyno-Mill) may be used or the cells may be broken up by shaking with glass beads or aluminum oxide or by alternately freezing, e.g., in liquid nitrogen, and thawing, e.g., to 30° to 40° C., or by ultrasound. The resulting mixture which contains proteins, nucleic acids and other cell constituents is concentrated with proteins in known manner after being centrifuged. Thus, for example, the majority of the non-protein constituents are separated off by polyethyleneimine treatment and the proteins including the VAC compounds are precipitated, for example, by saturation of the solution with ammonium sulphate or other salts. Other purification steps include, for example, chromatographic methods such as ion exchange chromatography, HPLC, reverse phase HPLC and the like. Thus, the components of the mixture are separated by dialysis, after charging using gel electrophoresis or carrier-free electrophoresis, in accordance with molecular size using a suitable Sephadex column, by affinity chromatography, e.g., with antibodies, particularly monoclonal antibodies, or with thrombin coupled to a suitable carrier for affinity chromatography, or by other methods, particularly those known from the literature.

For example, isolation of the expressed VAC compounds comprises the following steps. Separation of the cells from the culture solution by centrifuging; preparation of a crude extract by destruction of the cells, e.g., by treating with a lysing enzyme and/or alternate freezing and re-thawing; removing the insoluble matter by centrifuging; precipitating the DNA by the addition of polyethyleneimine; precipitating the proteins by means of ammonium sulphate; affinity chromatography of the dissolved precipitate on a monoclonal anti-VAC antibody column; removal of salts from the solution thus obtained by dialysis or chromatography on Sephadex G25 or Sephadex G10.

Other purification steps include gel filtration on Sephadex G50 (or G75) and reverse phase HPLC. On Sephadex G50 (or G75) and reverse phase HPLC. Salts may be removed on Sephadex G25.

The VAC activity can be detected using the test with anti-VAC antibodies (e.g., monoclonal antibodies obtainable from rabbits/mice or from hybridoma cells) or the tests described in EPA 0181465 may be used.

As already mentioned, the alkaline phosphatase promoter is particularly suitable for expression of the proteins according to the invention.

The gene for alkaline phosphatase (phoA) from *E. coli* is subject to strict regulation. In the presence of phosphate the gene is switched off completely and in the absence of phosphate in the medium gene expression takes place. Shuttleworth et al., *Nucleic Acids Res.* 14:8688 (1986), and Chang et al., *Gene* 44:121–125 (1986), describe the nucleotide sequence of this gene. In order to construct a suitable expression vector, the promoter region of the pho-A gene was assembled from several oligonucleotides and inserted into EcoRI-ClaI cut pAT153 (Amersham). In front of the ribosomal binding site, an XhoI site was introducted.

Original EcoRI site is destroyed when the synthetic DNA fragment is ligated in. A translation start ATG was provided after the ribosomal binding site the G of which is the first nucleotide of a SacI (=SstI) site. The expression vector can be linearized by cutting with SacI at this site and the 3′ overhang can be converted into a straight end by treating with DNA polymerase I - Klenow fragment in the presence dGTP. In this way, any desired gene can be inserted at this point; for correct expression it must begin with the first base of the coding region.

The HindIII-SalI fragment of the pAT section was removed and replaced by the alkaline phosphatase transcription terminator. The original SalI site was destroyed. To do this, it was reintroduced in front of the terminator together with the BamHI site which was also deleted from pAT153. The sequence of the synthetically produced DNA is shown in FIG. 21. The resulting vector is referred to as pRH284T. In order to prepare a vector which is suitable for expressing VAC-alpha, a DNA molecule coding for VAC-alpha was introduced into the pRH284T. For this purpose, the cDNA clone pP6/5 was cut with BglII and PstI and the 980 bp long fragment which contains the majority of the coding region and about 200 bp of 3′ non-translated region was isolated. The missing 5′ end of the coding region was replaced using oligonucleotides. A KpnI cutting site was simultaneously introduced into the VAC-cDNA by two mutations (GGC →GGT, Gly-7 and ACT→ACC, Thr-8).

The oligonucleotides had the following appearance:

|EBI-678 || EBI-677

GCACAGGTTCTCAGAGGTACCGTGACTGACTTCCCTGGATTTGATGAGCGGGCT

CGTGTCCAAGAGTCTCCATGGCACTGACTGAAGGGACCTAAACTACTCGCCCGA

| EBI-680 | |

GATGCAGAAACTCTTCGGAAGGCTATGAAAGGCTTGGGCACAGATGAGGAGAGC

CTACGTCTTTGAGAAGCCTTCCGATACTTTCCGAACCCGTGTCTACTCCTCTCG

EBI-

| | EBI-682 |

ATCCTGACTCTGTTGACATCCCGAAGTAATGCTCAGCGCCAGGAAATCTCTGCA 3′

TAGGACTGAGACAACTGTAGGGCTTCATTACGAGTCGCGGTCCTTTAGAG 5′

679 | | EBI-681 |

Figure 22:
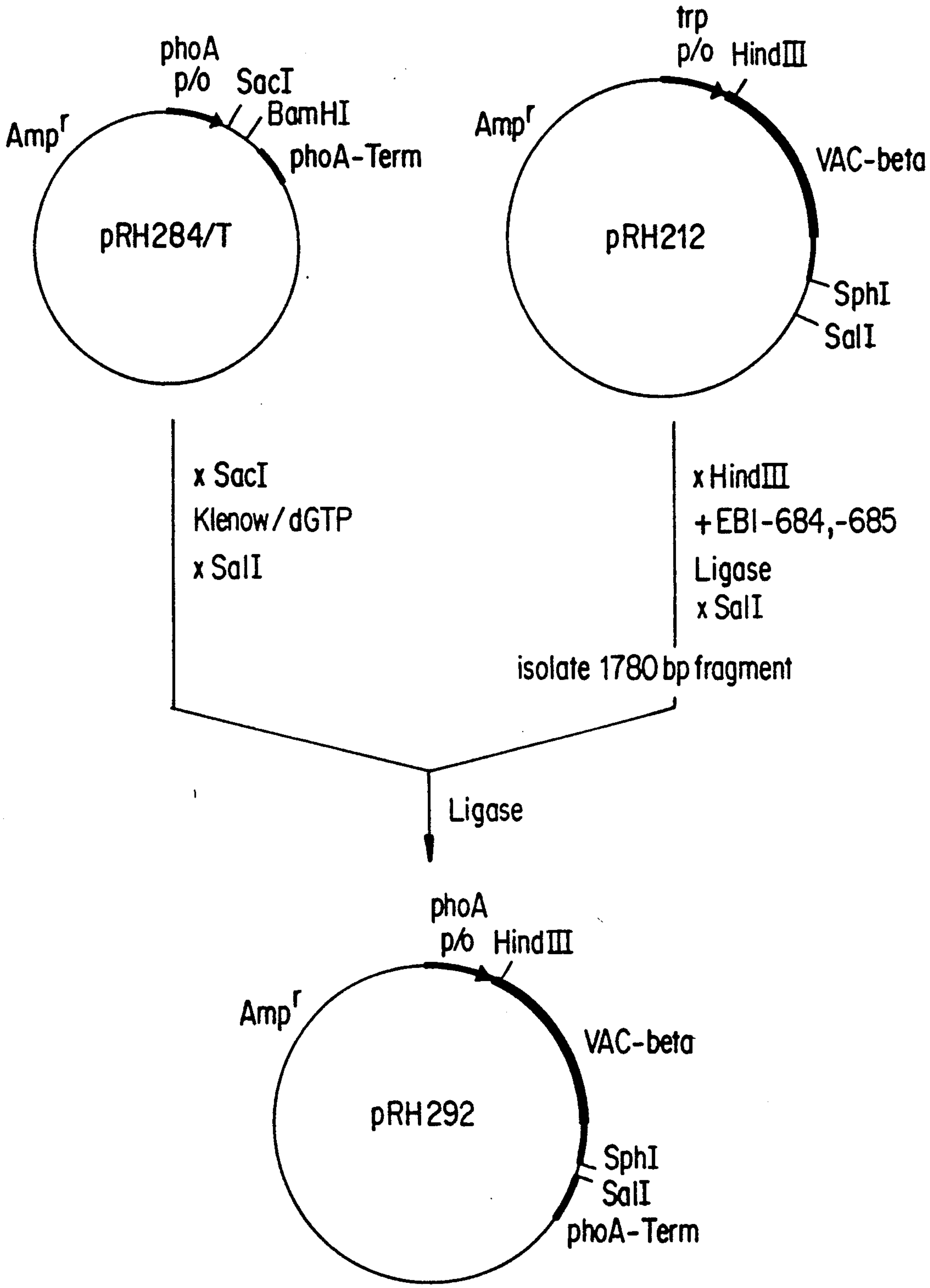
FIG. 22 depicts the construction of pRH291.

The vector thus produced was designated pRH291 (FIG. 22).

Figure 23:
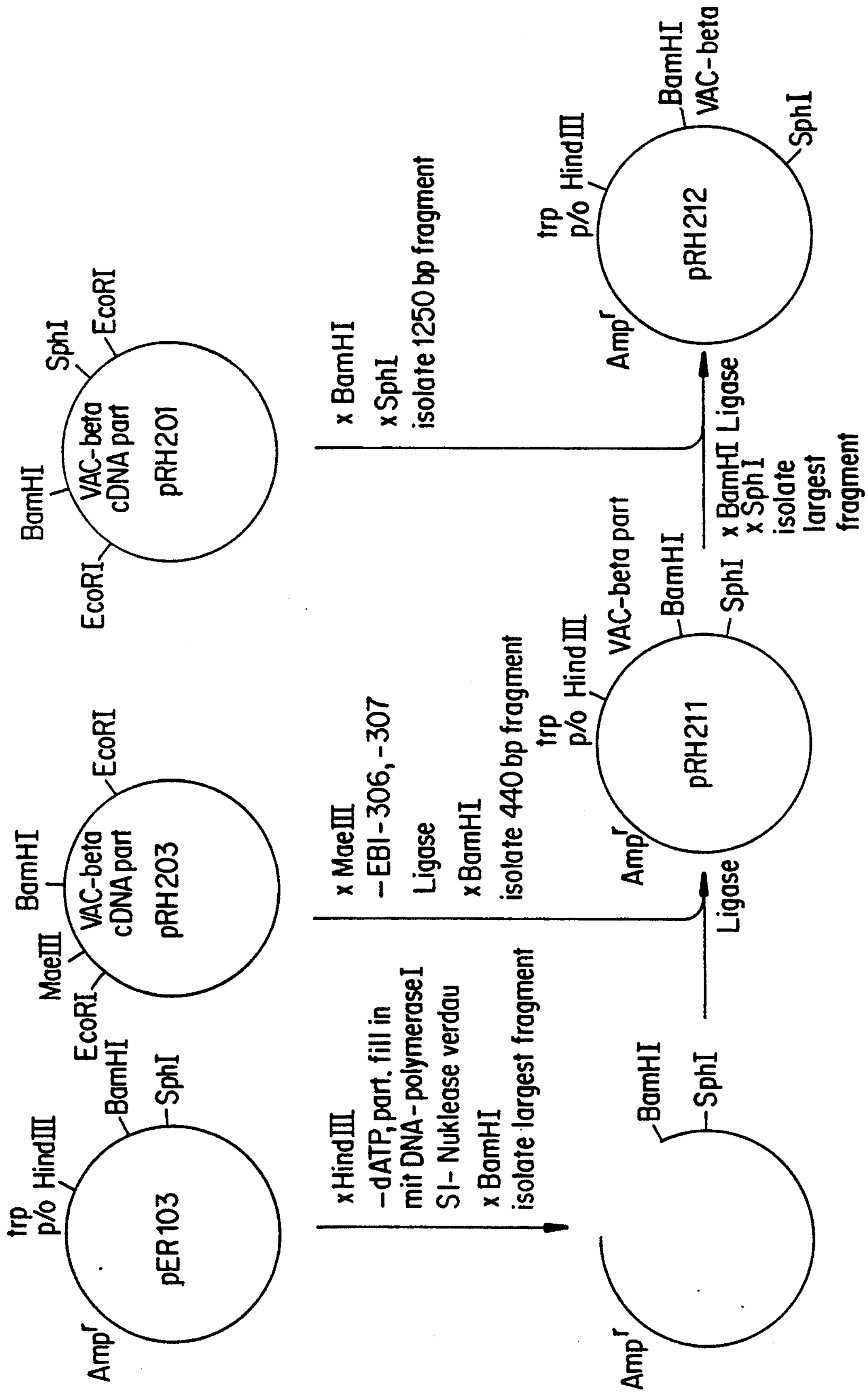
FIG. 23 depicts the construction of pRH212.

In order to express VAC-beta, the plasmid pER103 was preferably used as expression vector (Rastl-Dworkin et al., *Gene* 21:237–248 (1983)). The vector was linearised with HindIII. The 5′ overhanging end was partially filled in with dATP and DNA polymerase I/Klenow fragment and the remaining single strand residue was digested with S1 nuclease. The vector was cut with BamHI and the large fragment was isolated (FIG. 23). The DNA molecule coding for VAC-beta was ligated into the vector thus prepared. For this purpose, the 440 bp long MaeIII-BamHI fragment which contains the codons 13 to 157 was isolated from the clone pRH203. The missing 5′ end was supplemented using oligonucleotides:

EBI-307
5′ CCATGGCTTGGTGGAAAGCTTGGATCGAACAGGAAGGT 3′
3′ GGTACCGAACCACCTTTCGAACCTAGCTTGTCCTTCCACAGTG 5′ EBI-306

Optimum codons were used for *E. coli* (e.g., Grantham et al., *Nucleic Acids Res.* 8:1893–1912 (1980)). This codon exchange resulted in a new HindIII site at codons 5 to 7. After re-cutting with BamHI, the 5′ terminal VAC fragment was ligated into the prepared pER103 vector. The vector formed was designated pRH211. In order to complete the region coding for VAC-beta, the 1230 bp long BamHI-SphI fragment was isolated from the clone pRH201. The approximately 200 bp long pBR322 section from BamHI to SphI from the plasmid pRH211 was removed and replaced by the corresponding VAC cDNA part. This reslted in the vector pRH212. The EcoRI-BamHI fragment which contains the Trp promoter (*S. marcescens*), the ribosomal binding site and the synthetically produced beginning of the VAC-beta gene was checked by sequencing. The plasmid-encoded VAC-beta was detected in a maxicell system (Sancar et al., *J. Bacteriol.* 137:692–693 (1979)).

The construction of an expression vector starting from pRH284T is particularly preferred for the expression of VAC-beta. For this purpose, the insert coding for VAC-beta was ligated into the expression vector in suitable manner. The vector pRH212, for example, may be used as starting material for this insert.

The expression vector pRH284T was linearised with SacI and the 3′ overhanging ends were converted into straight ends using DNA polymerase I/Klenow fragment and dGTP. The vector ws recut with SalI and the large fragment was isolated. The HindIII-SalI insert of clone pRH212 was isolated. The pair of oligonucleotides

Figure 24:
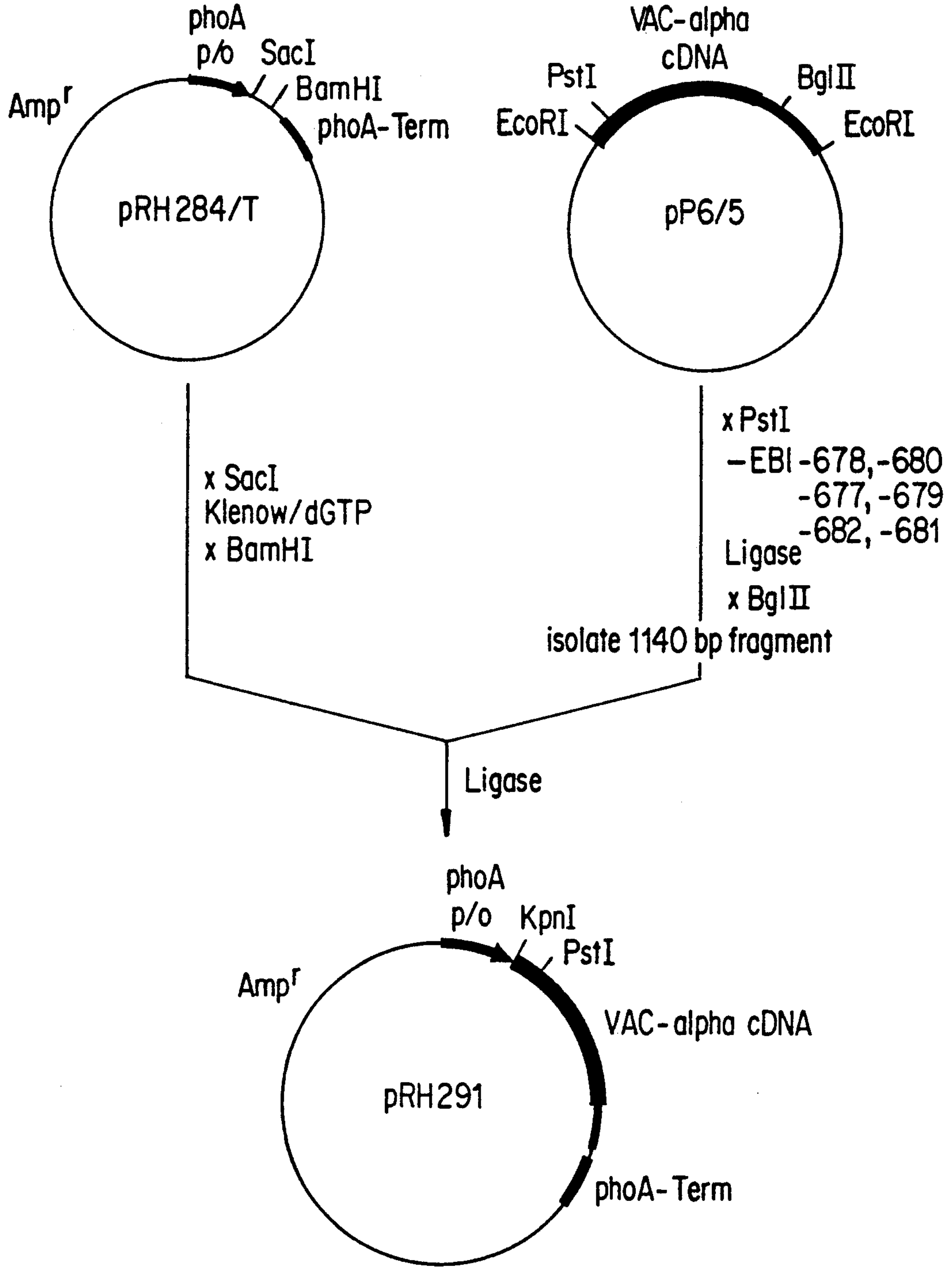
FIG. 24 depicts the construction of pRH292.

5′ GCTTGGTGGAA 3′ EBI-684
3′ CGAACCACCTTTCGA 5′ EBI-685 were ligated with the VAC-beta insert and the prepared pRH284T. *E. coli* HB101 was transformed with the ligase solution. The resulting clone was designated pRH292 (FIG. 24).

Figure 42:
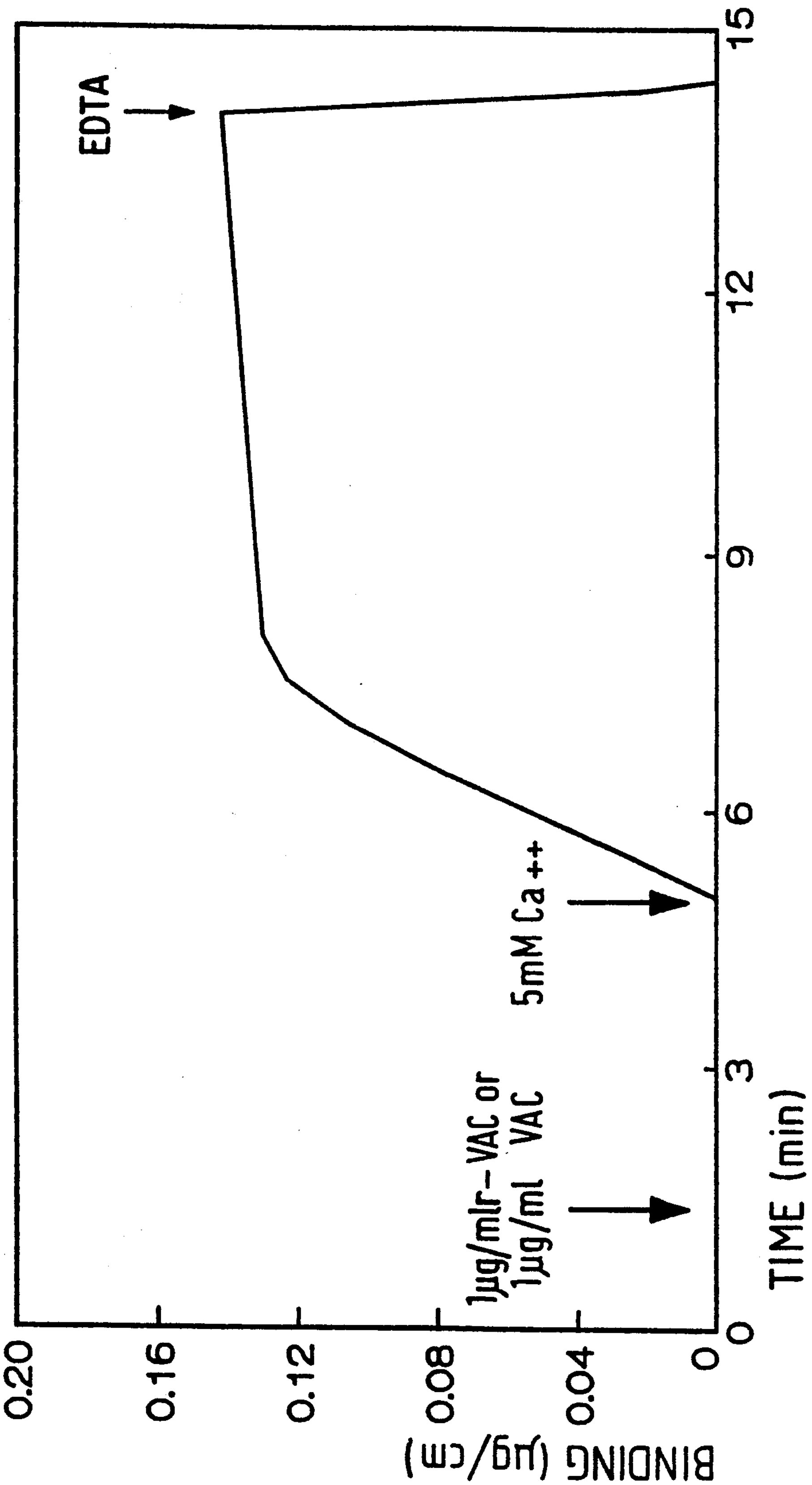
FIG. 42 depicts the binding of VAC to phospholipid double layers.
Figure 43:
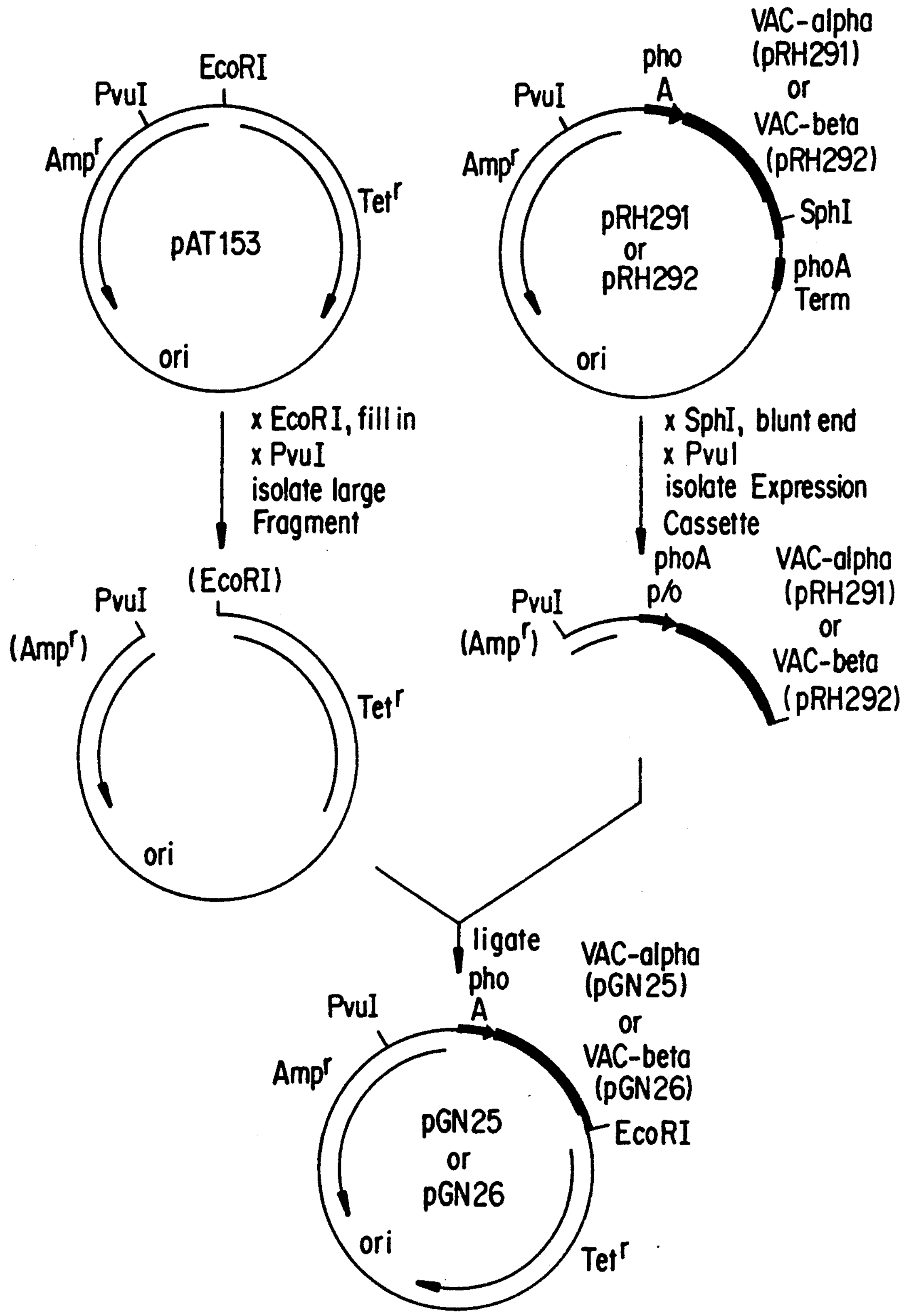
FIG. 43 depicts the construction of pGN25 and pGN26.
Figure 44:
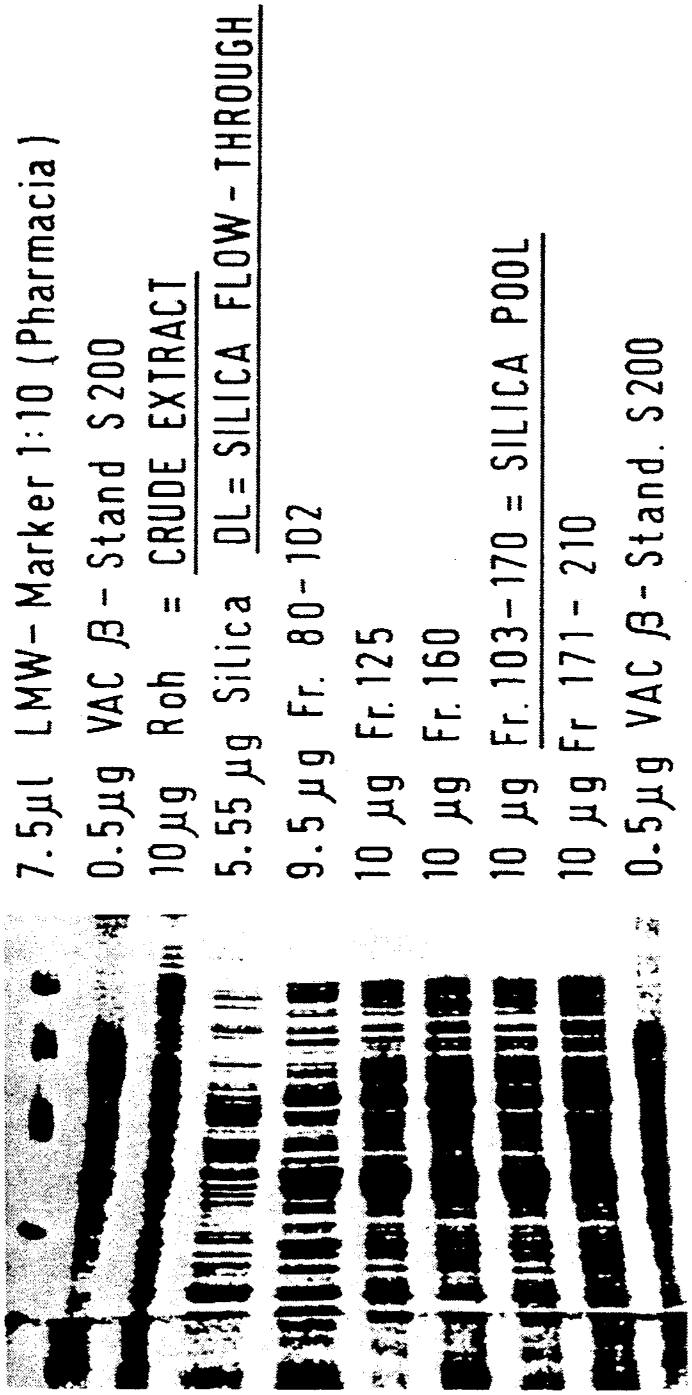
FIG. 44 depicts the purification of recombinant VAC-β; Coomassie Blue stained 2.5% SDS-PAGE gel electrophoresis gel.

Since the tetracycline resistance gene has been deleted from the promoter to the SalI site in the expression vectors pRH291 (VAC-$\alpha$) and pRH292 (VAC-$\beta$), these vectors cannot confer any tetracycline resistance. Tetracycline-resistant expression vectors are obtained for example by the construction according to the plan in FIG. 42. VAC-$\alpha$ and VAC-$\beta$ cDNA each have an SphI site in the 3' untranslated region. In the lactamase gene of the vector there is a PvuI site. Both recognition sequences are singular. Therefore, by cutting with PvuI and SphI, part of the B-lactamase gene, the phoA promoter and the cDNA containing the entire coding part of the VAC-$\alpha$ or $\beta$ plus some 3' untranslated cDNA can be freed from the two expression vectors. On the other hand by cutting with PvuI and EcoRI the remainder of the B-lactamase gene, the replication origin and the entire tetracycline resistance gene including the promoter can be freed from the plasmid pAT153. If the SphI or EcoRI ends are straightened by enzymatic treatment, compatible ends are obtained. If vector fragment and the fragment containing VAC-$\alpha$ or VAC-$\beta$ cDNA are ligated, expression vectors are formed which contain the complete tetracycline resistance gene: pGN25 (VAC-$\alpha$), pGN26 (VAC-$\beta$).

Competent host organisms, particularly, *E. coli*, more especially, *E. coli* HB101 were transformed with the expression vectors thus prepared and cultivated in suitable media.

A medium which is well suited to the expression of VAC-alpha and VAC-beta will now be described with its components:

| | | |
|---|---|---|
| 0.2-2.0 | g/l | $(NH_4)_2HPO_4$ |
| 0.1-1.5 | g/l | $K_2HPO_4.3H_2O$ |
| 0.1-5 | g/l | KCl |
| 0.1-10 | g/l | NaCl |
| 0-5 | g/l | $NH_4Cl$ |
| 0.1-5 | g/l | $MgSO_4.7H_2O$ |
| 0.001-0.1 | g/l | $CaCl_2$ |
| 1-50 | mg/l | thiamine.HCl |
| 0.5-100 | mg/l | $(NH_4)_2Fe(SO_4)_2.6H_2O$ |
| 0.1-5 | mg/l | $AlCl_3.6H_2O$ |
| 0.1-10 | mg/l | $CoCl_2.6H_2O$ |
| 0.2-5 | mg/l | $KCr(SO_4)_2.12H_2O$ |
| 0.1-5 | mg/l | $CuSO_4.5H_2O$ |
| 0.05-1 | mg/l | $H_3BO_3$ |
| 0.1-5 | mg/l | $MnSO_4.H_2O$ |
| 0.1-5 | mg/l | $NiSO_4.6H_2O$ |
| 0.1-5 | mg/l | $Na_2MoO_4.2H_2O$ |
| 0.1-5 | mg/l | $ZnSO_4.7H_2O$ |
| 10-30 | g/l | casein hydrolysate (Merck Art. No. 2238) |
| 0-100 | g/l | casein hydrolysate (Sigma C9386) |
| 0.10-1 | mg/l | cysteine |
| 0-10 | g/l | yeast extract (Difco) |
| 0-2 | g/l | citric acid |
| 0-50 | g/l | glucose (start) |
| 5-50 | g/l | glucose, (fed in during fermentation) |

A medium with the following composition is particularly suitable:

Media:

1) Preliminary culture
10 g/l tryptone
5 g/l yeast extract
4 g/l glucose
9 g/l $Na_2HPO_4.2H_2O$
1 g/l $NH_4Cl$
1 g/l KCl
1 ml/l 1M $MqSO_4.7H_2O$
100 mg/l ampicillin
Starting pH=7.2

2) Main culture
0.68 g/l $(NH_4)_2HPO_4$
0.62 g/l $K_2HPO_43H_2O$
2.33 g/l KCl
0.5 g/l NaCl
0.53 g/l $NH_4Cl$
1.23 g/l $MgSO_4.7H_2O$
0.011 g/l $CaCl_2$
10 mg/l thiamine.HCl
3.92 mg/l $(NH_4)_2Fe(SO_4)_2.6H_2O$
0.72 mg/l $AlCl_3.6H_2O$
0.71 mg/l $CoCl_2.6H_2O$
1.5 mg/l $KCr(SO_4)_2.12H_2O$
0.75 mg/l $CuSO_4.5H_2O$
0.19 mg/l $H_3BO_3$
0.51 mg/l $MnSO_4.H_2O$
0.79 mg/l $NiSO_4.6H_2O$
0.73 mg/l $Na_2MoO_4.2H_2O$
0.86 mg/l $ZnSO_4.7H_2O$
21 g/l casein hydrolysate (Merck Art. No. 2238)
25 g/l casein hydrolysate (Sigma C9386)
100 mg/l cysteine
2 g/l yeast extract
1 g/l citric acid
11 g/l glucose.$H_2O$ (start or feed)

For fermentation, for example the pre-culture medium was inoculated with *E. coli* transformed with the corresponding expression vector and incubated with stirring and with the introduction of oxygen. Some of this pre-culture was then transferred into a fermenter with the main culture medium and cultivated with stirring and aeration. During the fermentation period, the concentration of glucose and the partial oxygen pressure were observed and adjusted to the optimum. After about 20 hours' fermentation the mixture was cooled, the nutrient medium was separated from the biomass and frozen.

Figure 25A:
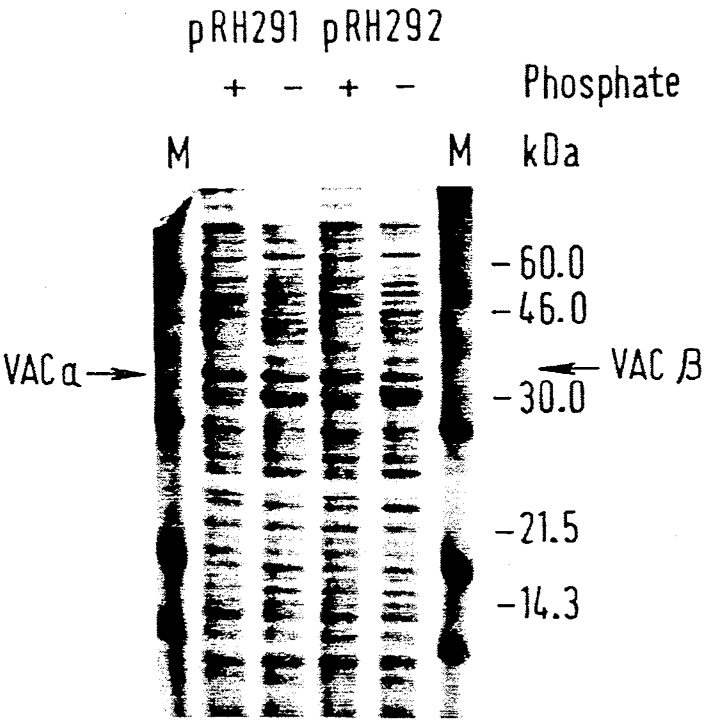
FIGS. 25a and 25b depict an SDS gel electrophoresis of the expressed proteins
25a) Coomassie Blue stained protein gel
25b) Western blot
   Legend: M=Molecular weight marker
   +phosphate=inhibition of VAC expression
   −phosphate=VAC expression (pho promoter induced)
Figure 25B:
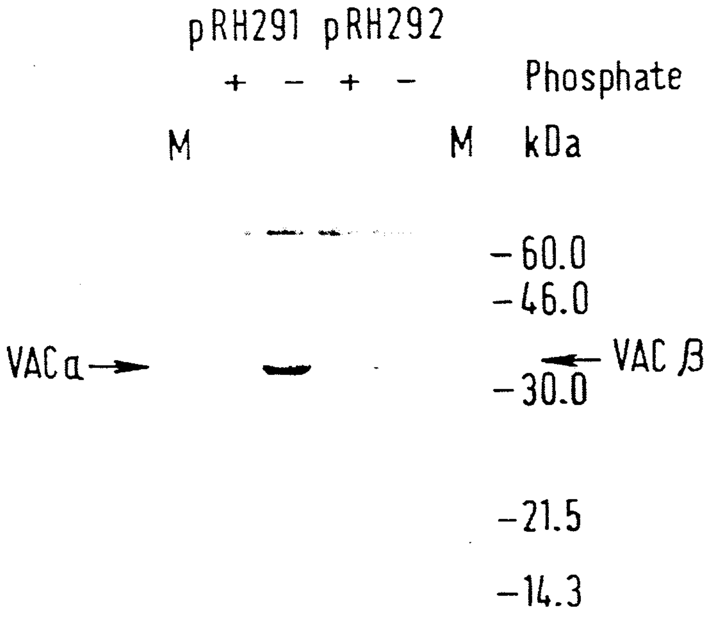
Figure 26:
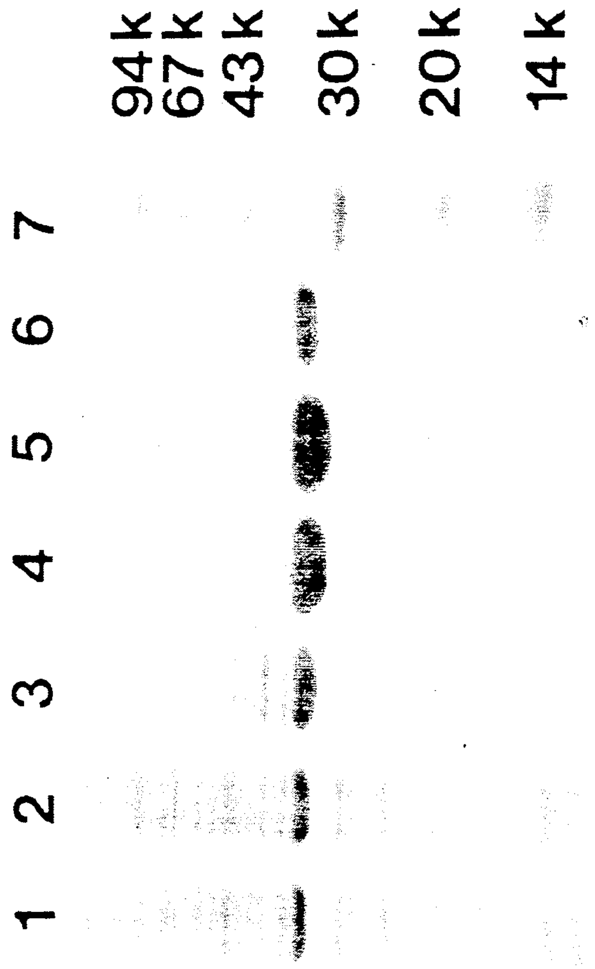
FIG. 26 depicts the purification of VAC-alpha; Coomassie Blue stained SDS gel electrophoresis gel.
Bands:
1: Crude extract
2: Ammonium sulphate pellets (dissolved and dialyzed)
12: 5 mcg of DEME-FF Sepharose fractions 1-11
3: VAC pool after DEAE-FF Sepharose chromatography
4: VAC pool after Sephacryl-S 200 HR chromatography
5: Purified VAC after Q-Sepharose-FF chromatography
6: Purified natural VAC from human placenta
7: Modecular weight marker (Pharmacia; 94kD, 67 kD, 43kD, 30kD, 20kD and 14kD)
Figure 27:
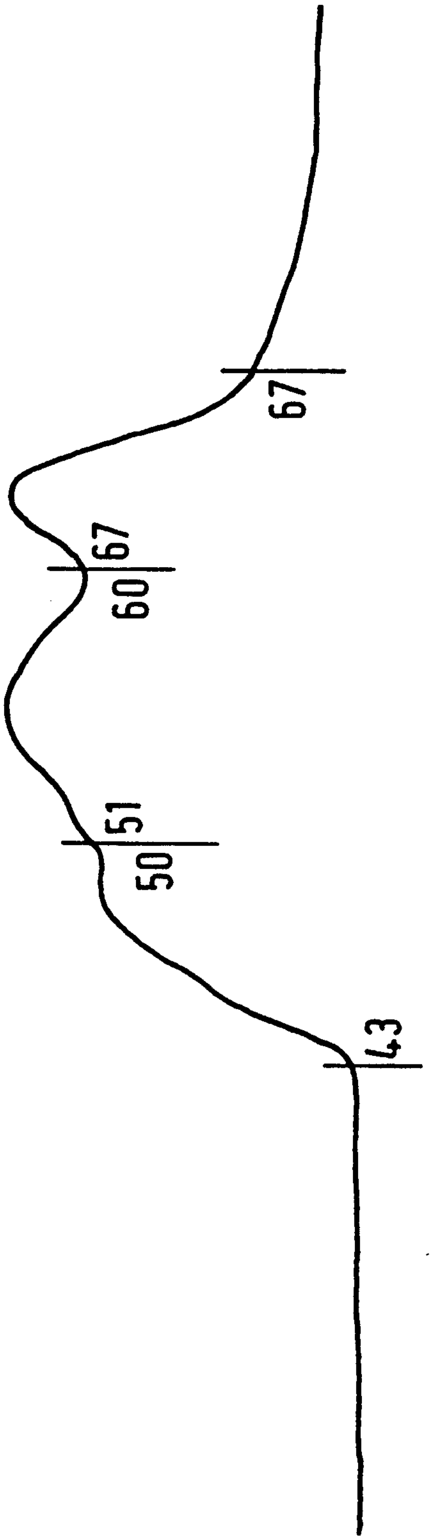
FIG. 27 depicts Sephacryl S-200 HR chromatography of pre-purified r-VAC-α.
Figure 28:
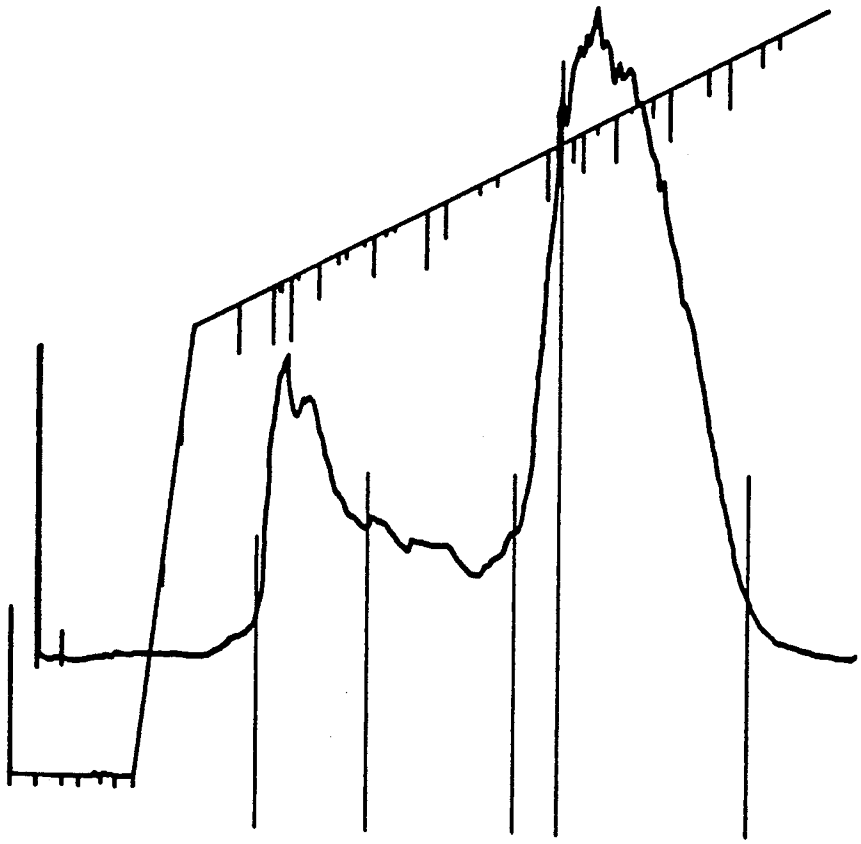
FIG. 28 depicts Q-Sepharose-FF chromatography of pre-purified r-VAC-α.
Figure 29:
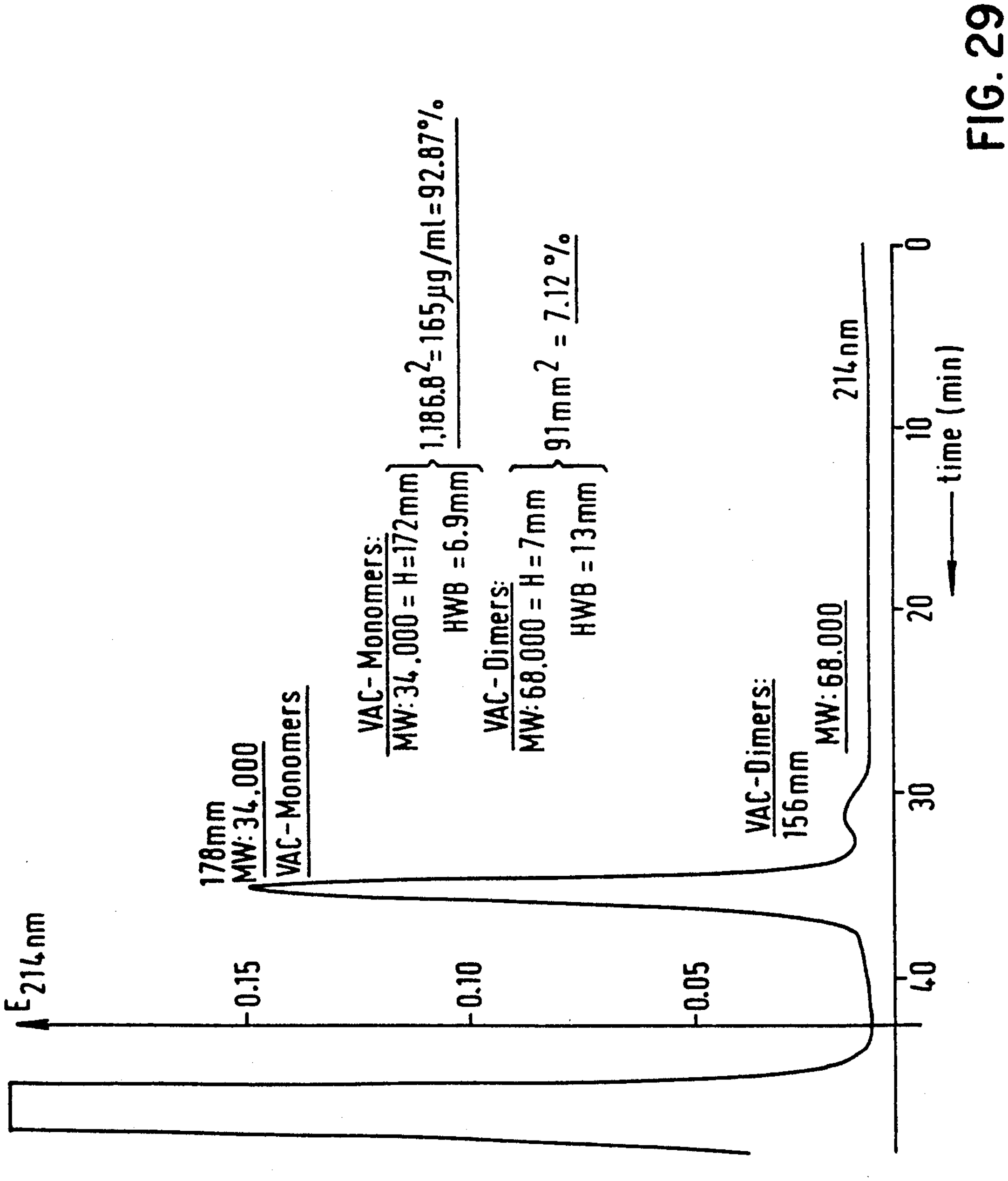
FIG. 29 depicts a gel permeation HPLC of natural VAC.
Figure 30:
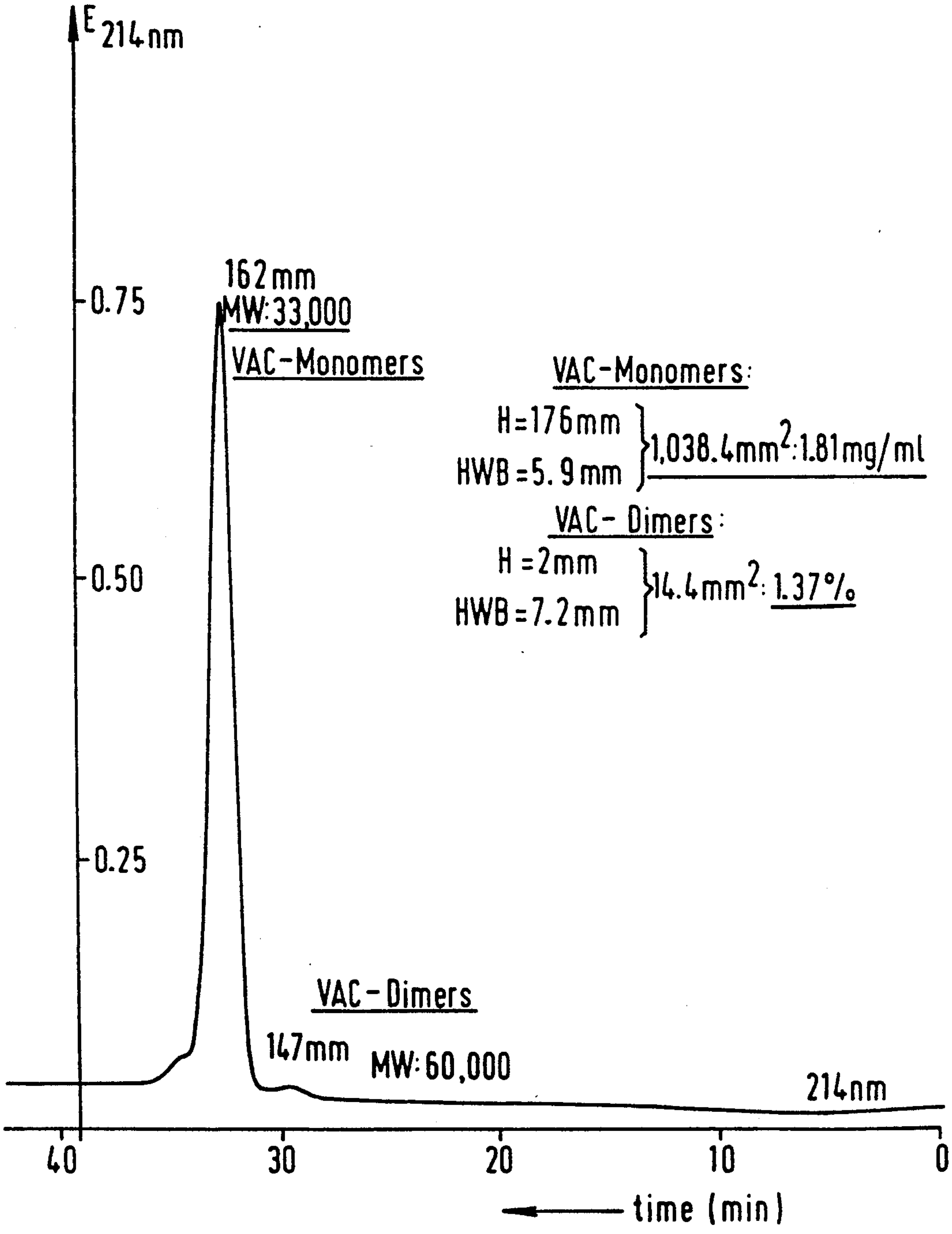
FIG. 30 depicts a gel permeation HPLC of recombinant VAC-α.
Figure 31:
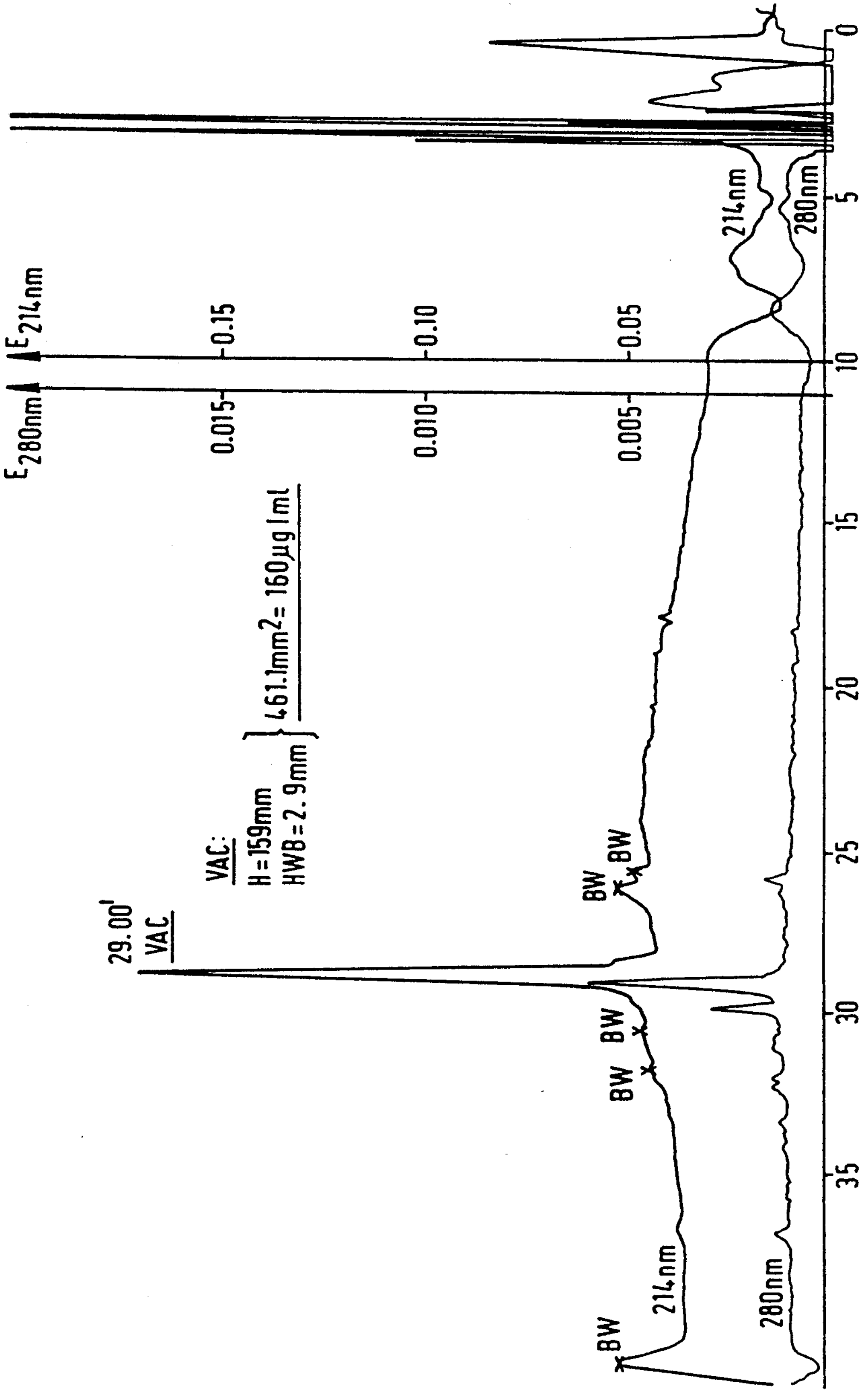
FIG. 31 depicts a reverse phase HPLC of natural VAC.
Figure 32:
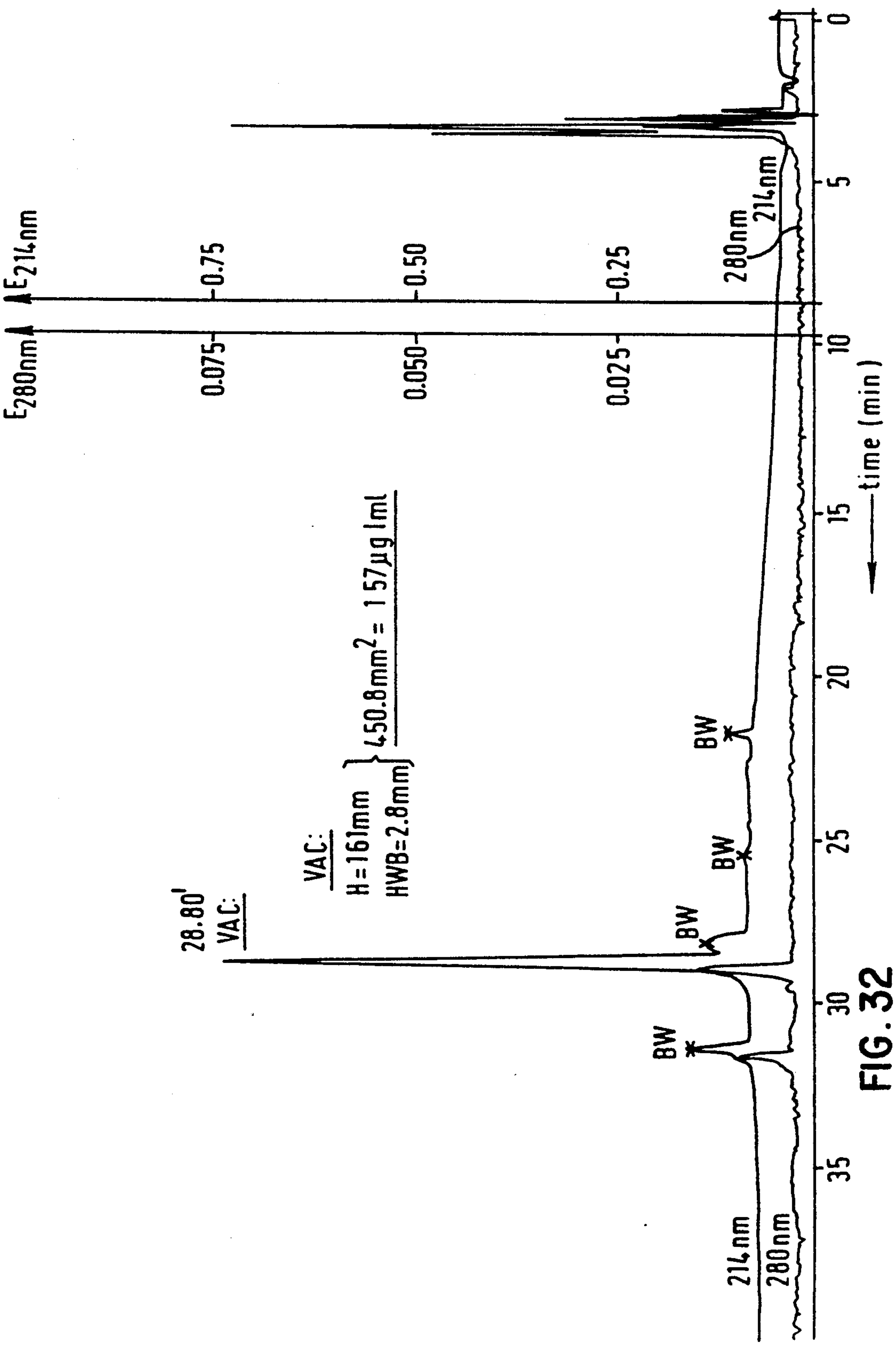
FIG. 32 depicts a reverse phase HPLC of recombinant VAC-α.
Figure 33:
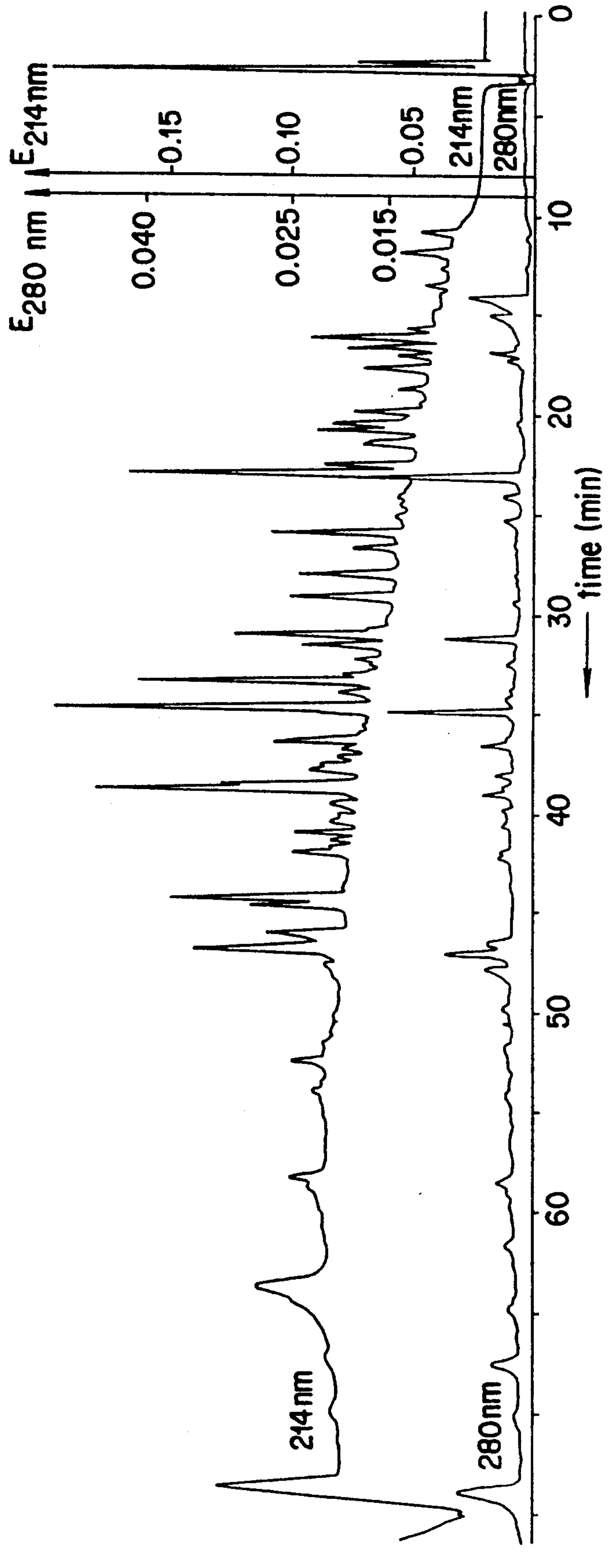
FIG. 33 depicts an HPLC of the tryptic fragments from natural VAC.
Figure 34:
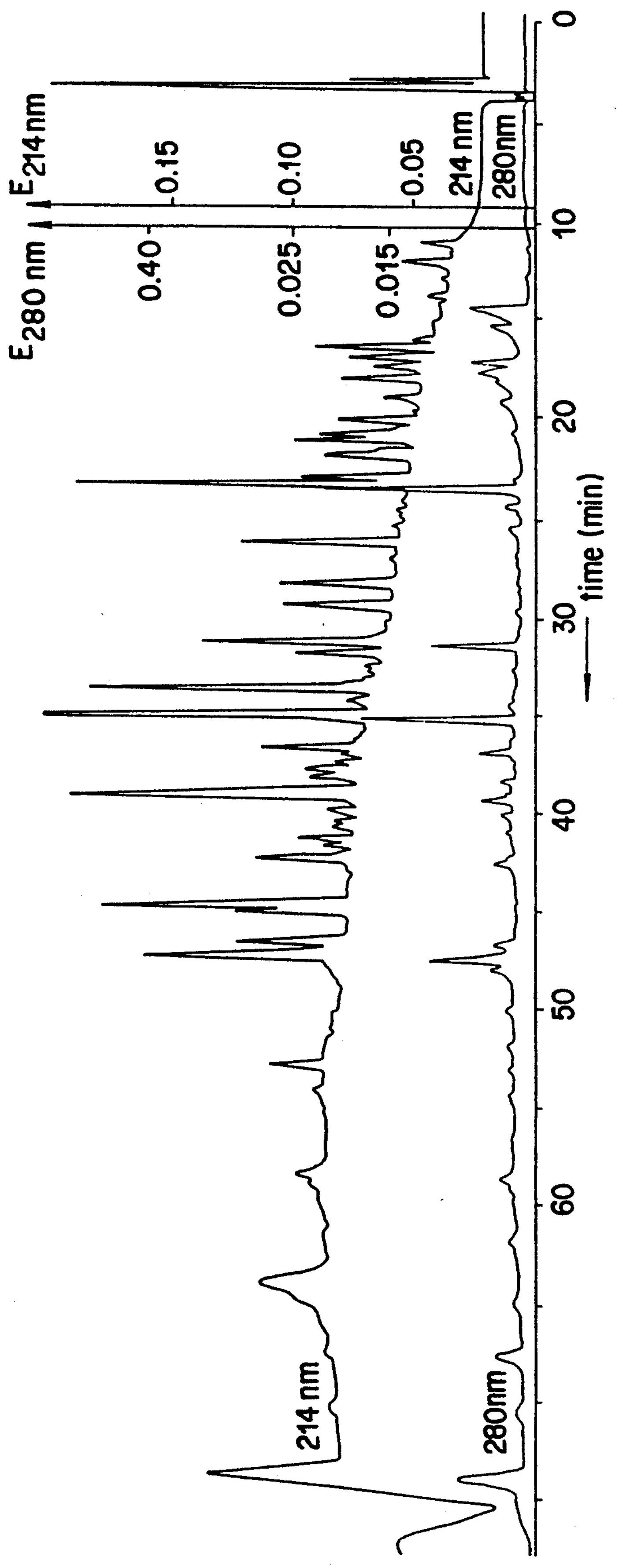
FIG. 34 depicts an HPLC of the tryptic fragments from recombinant VAC-α.
Figure 35:
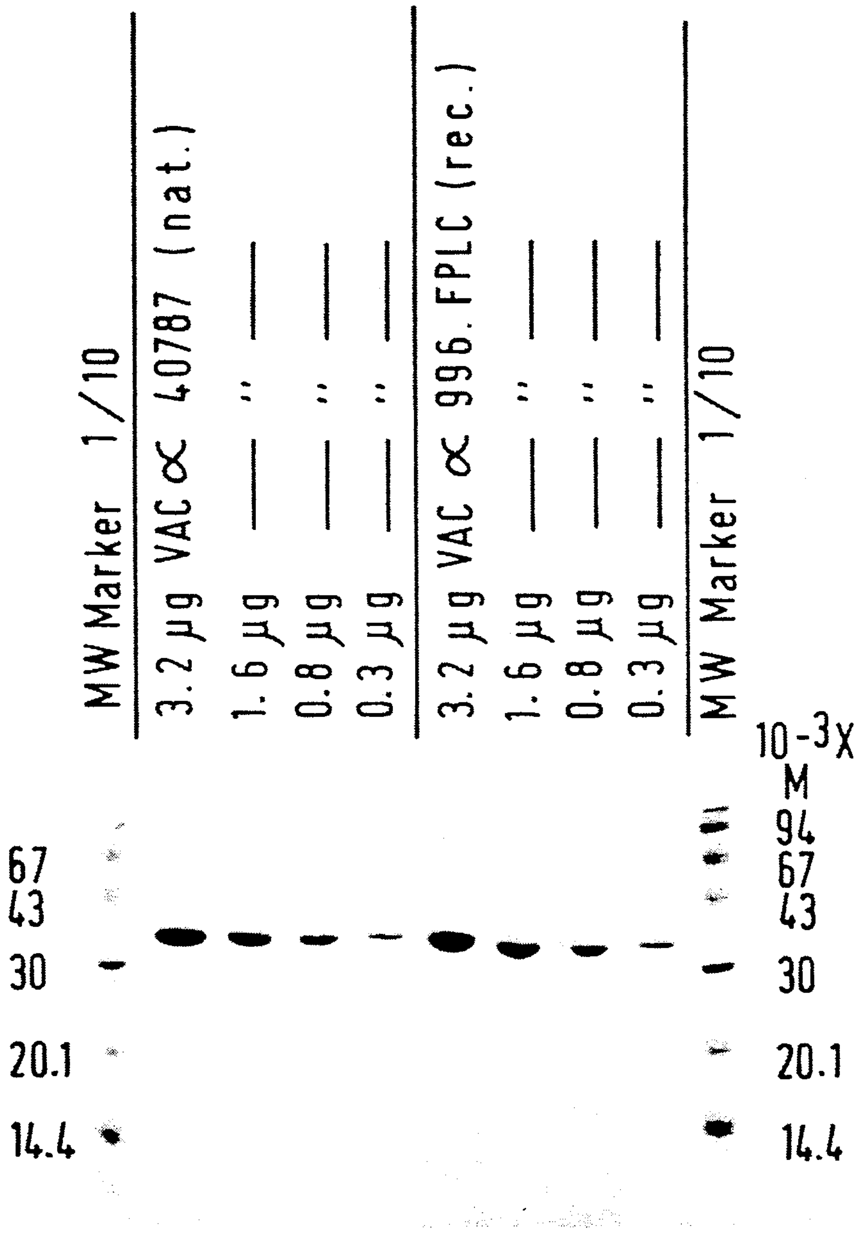
FIG. 35 depicts an SDS gel from a comparison between natural and recombinant VAC-α in the presence or absence of DTT.
Figure 36:
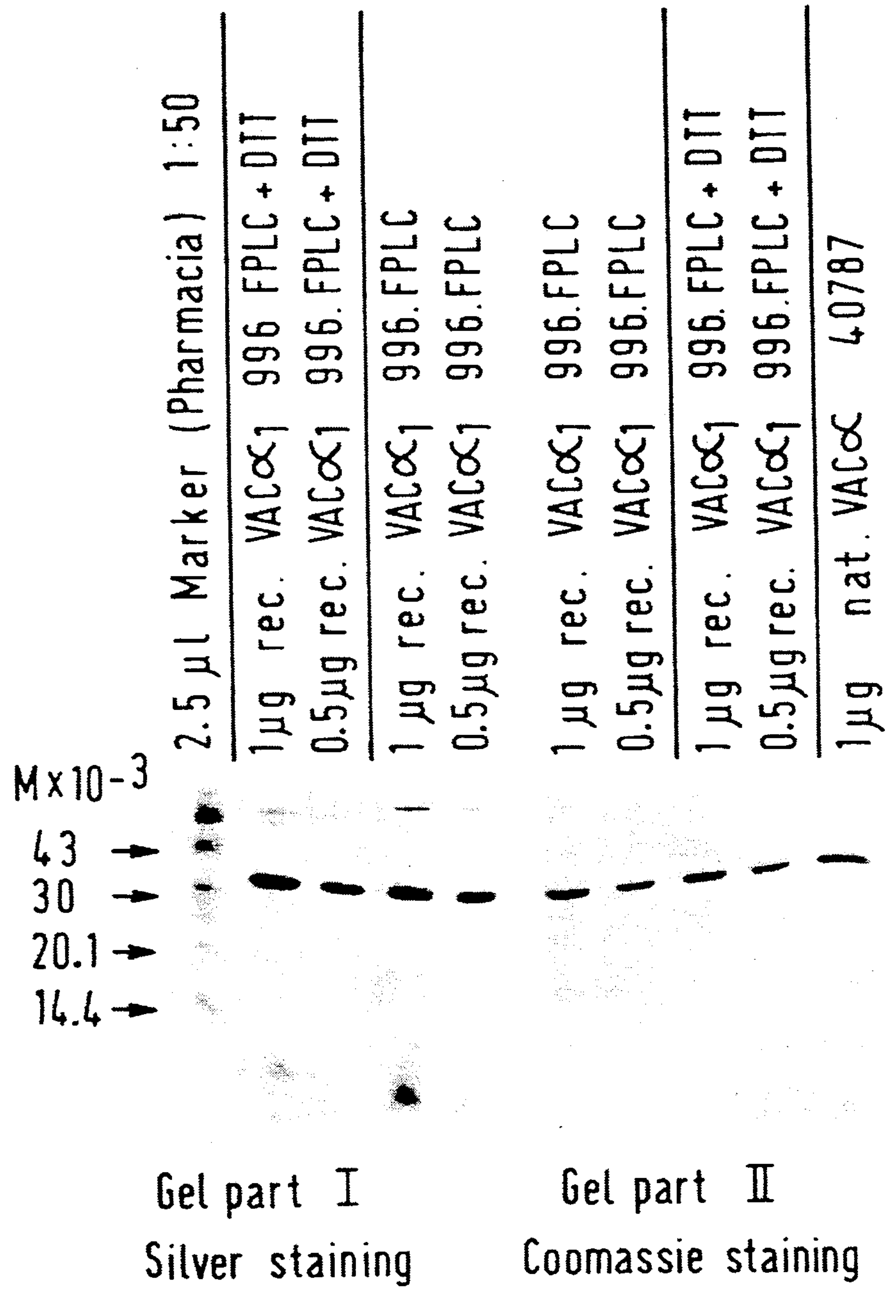
FIG. 36 depicts a 15% PAGE-SDS gel from recombinant VAC-α in the presence or absence of DTT.
Figure 37:
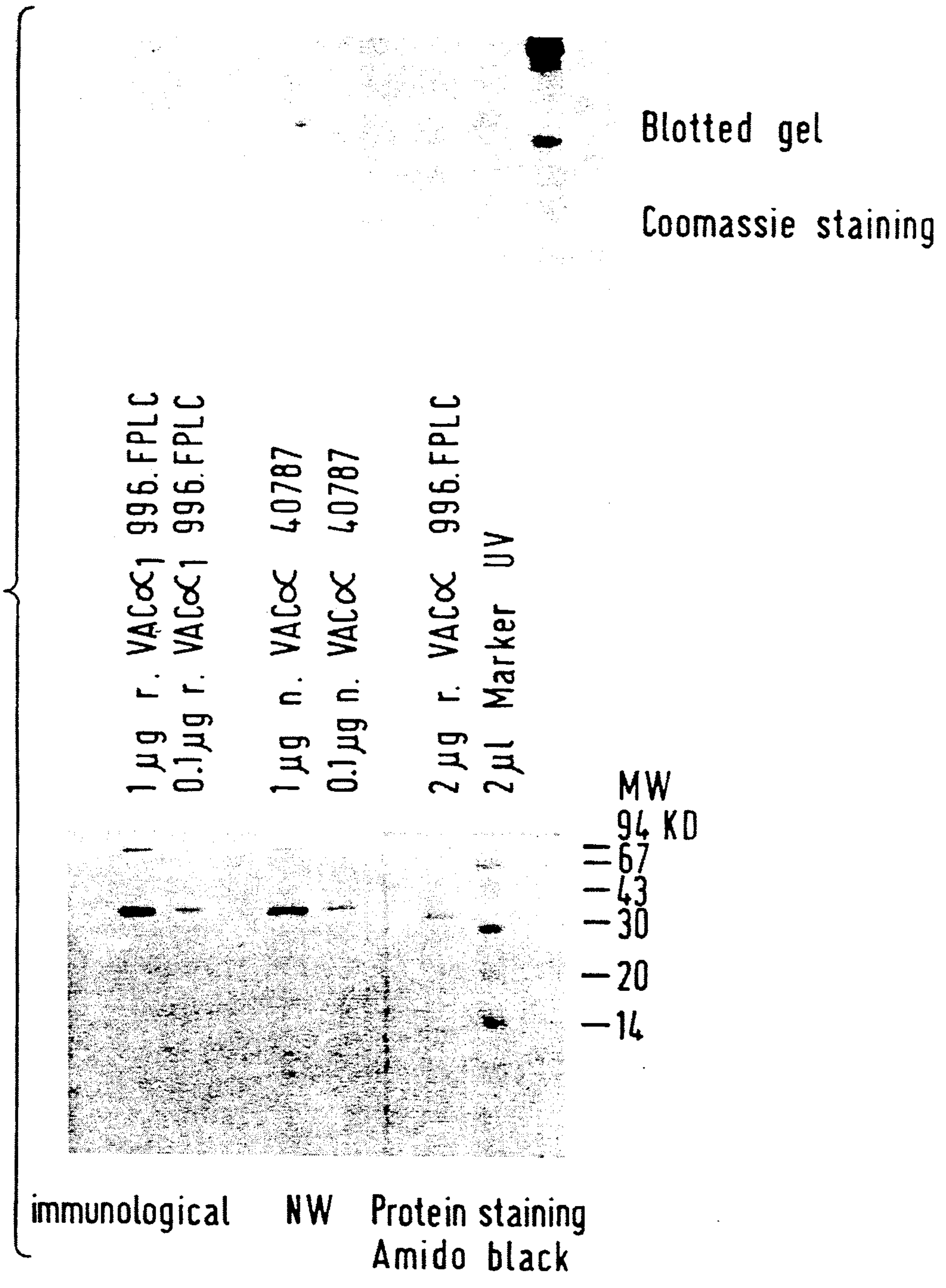
FIG. 37 depicts a Western Blot analysis of natural VAC and recombinant VAC-α separated on 15% SDS-PAGE.
Figure 38A:
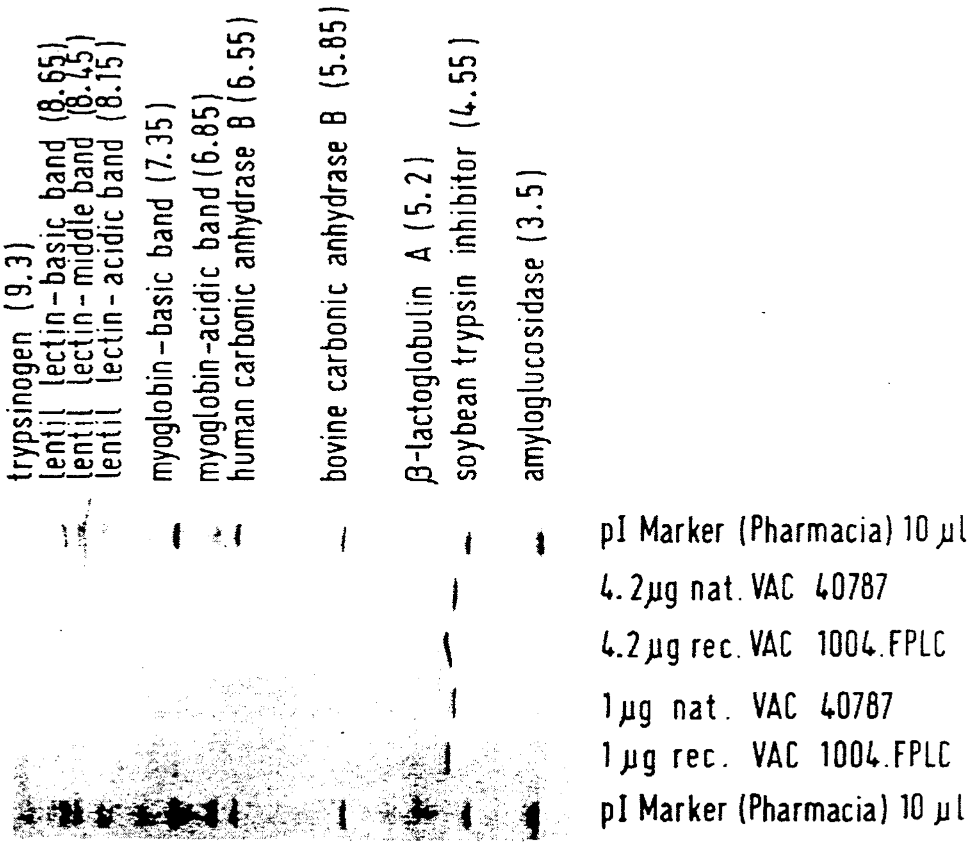
FIG. 38a depicts an isoelectric focussing gel of natural VAC and recombinant VAC-α (LKB AMPHOLINE PAGIF pH 3.5-9.5), visualized by Coomassie staining.
Figure 38B:
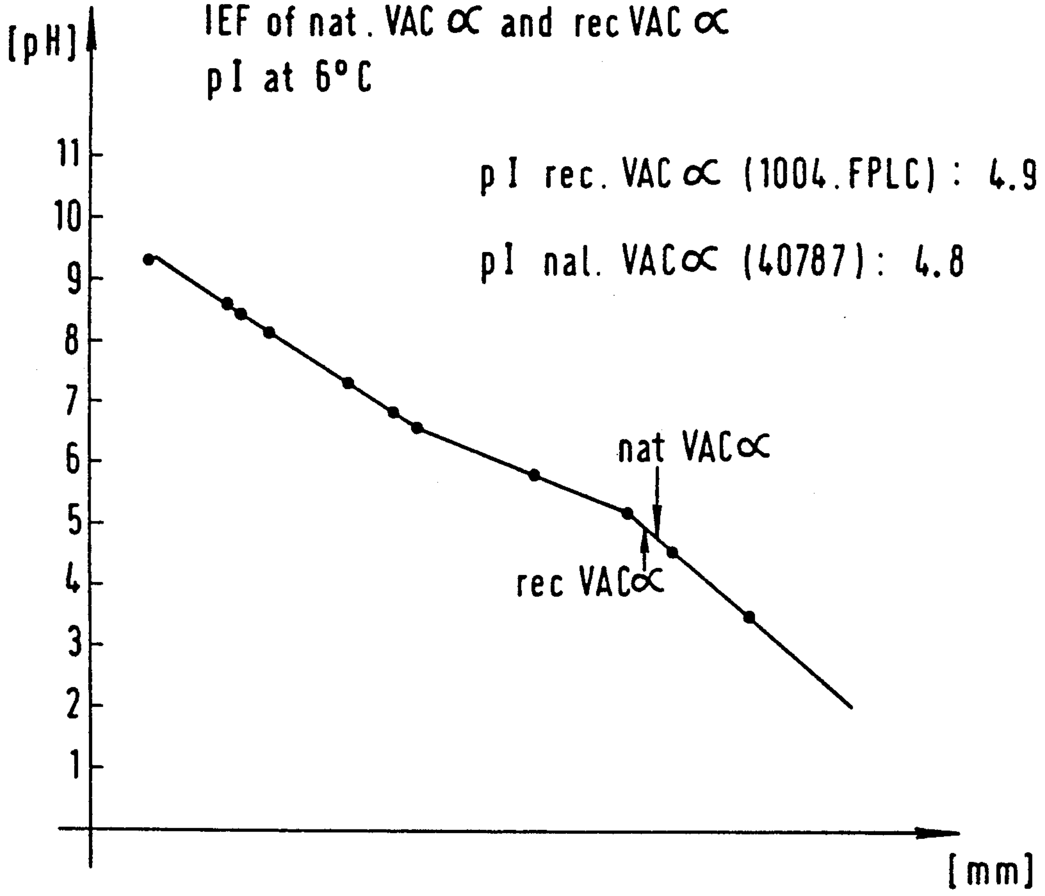
FIG. 38b depicts a graphical representation of the results of isoelectric focusing.
Figure 39:
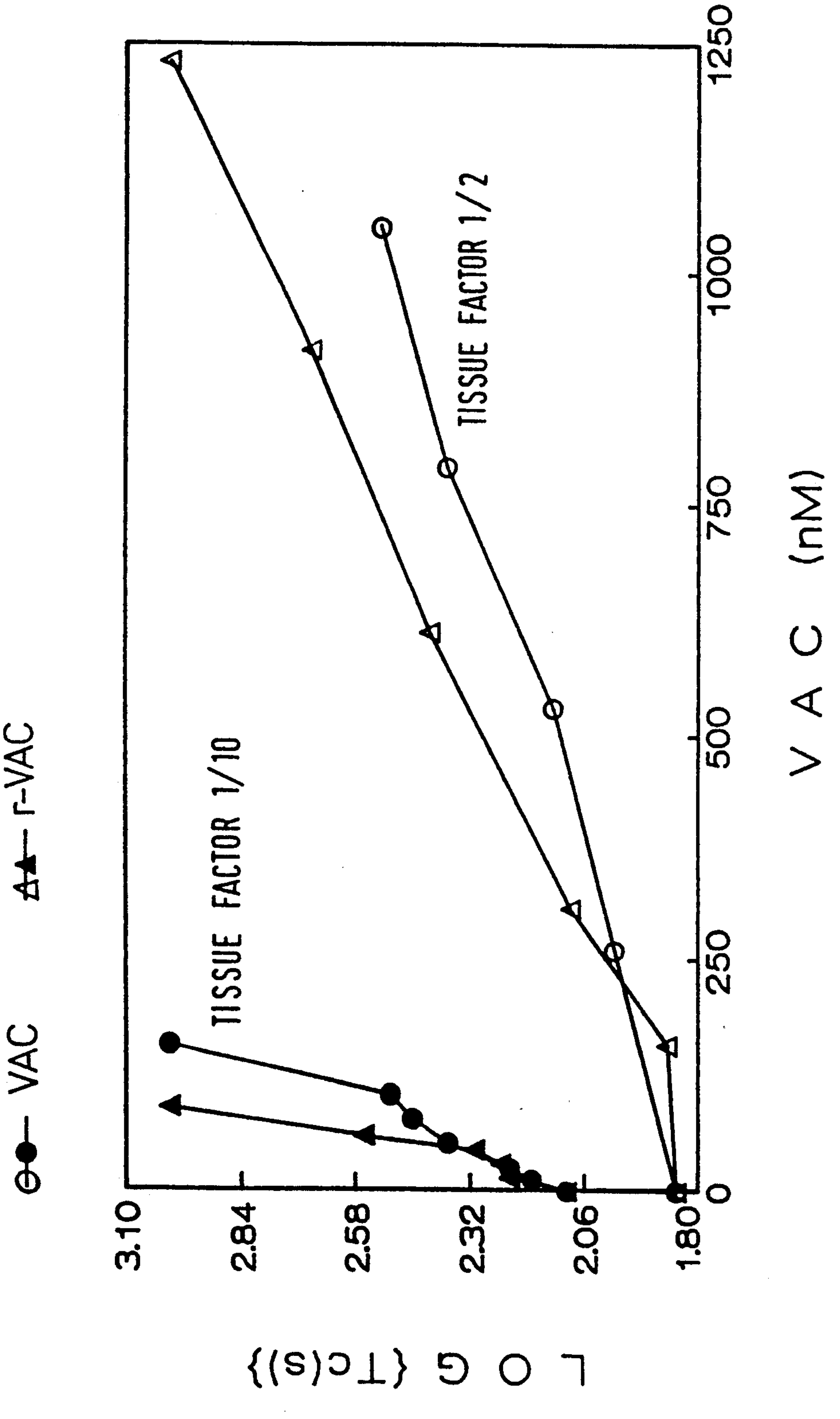
FIG. 39 depicts a modified prothrombin time test with natural and recombinant VAC.
Figure 40:
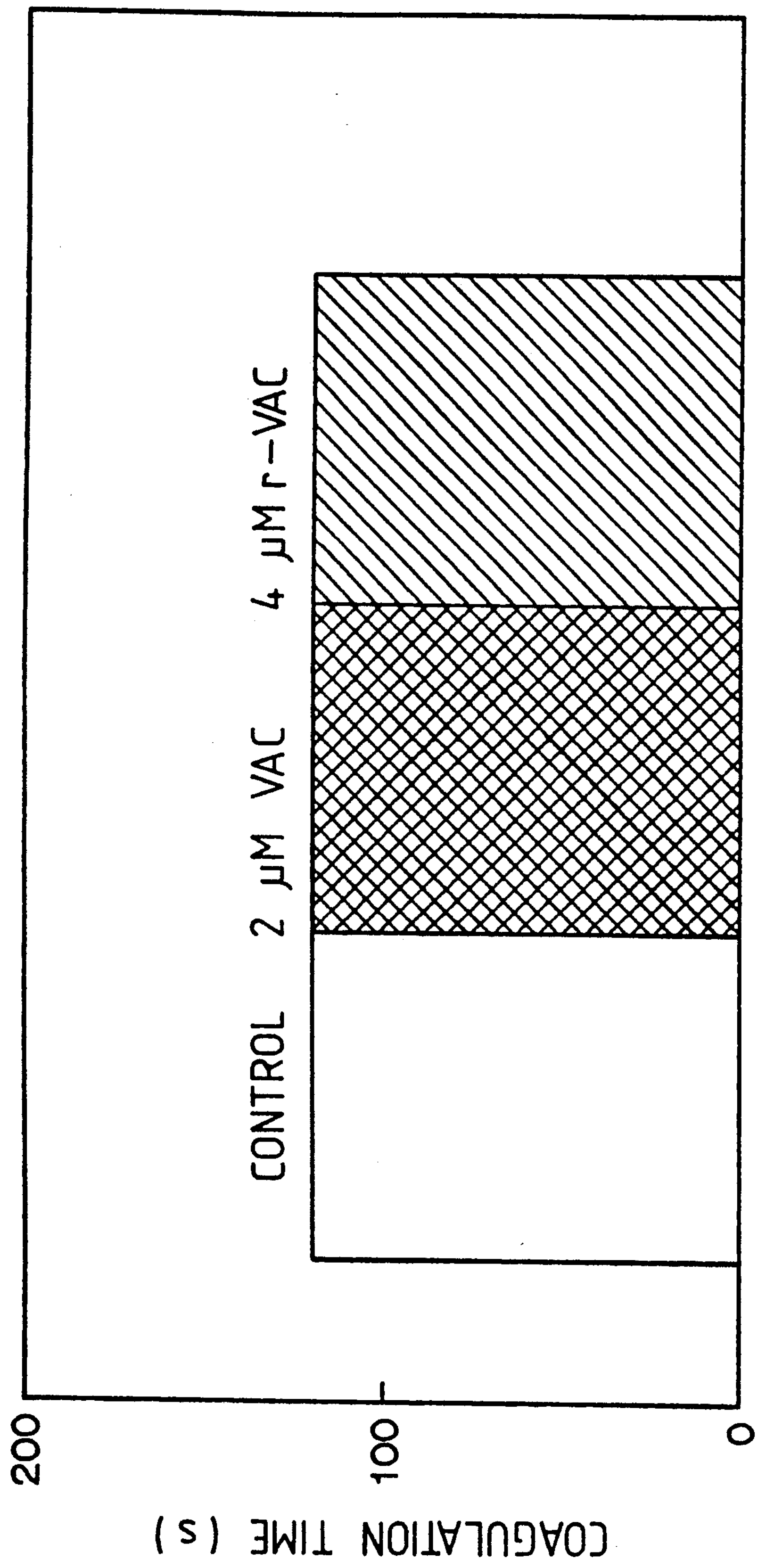
FIG. 40 depicts a thrombin time test with natural and recombinant VAC.
Figure 41:
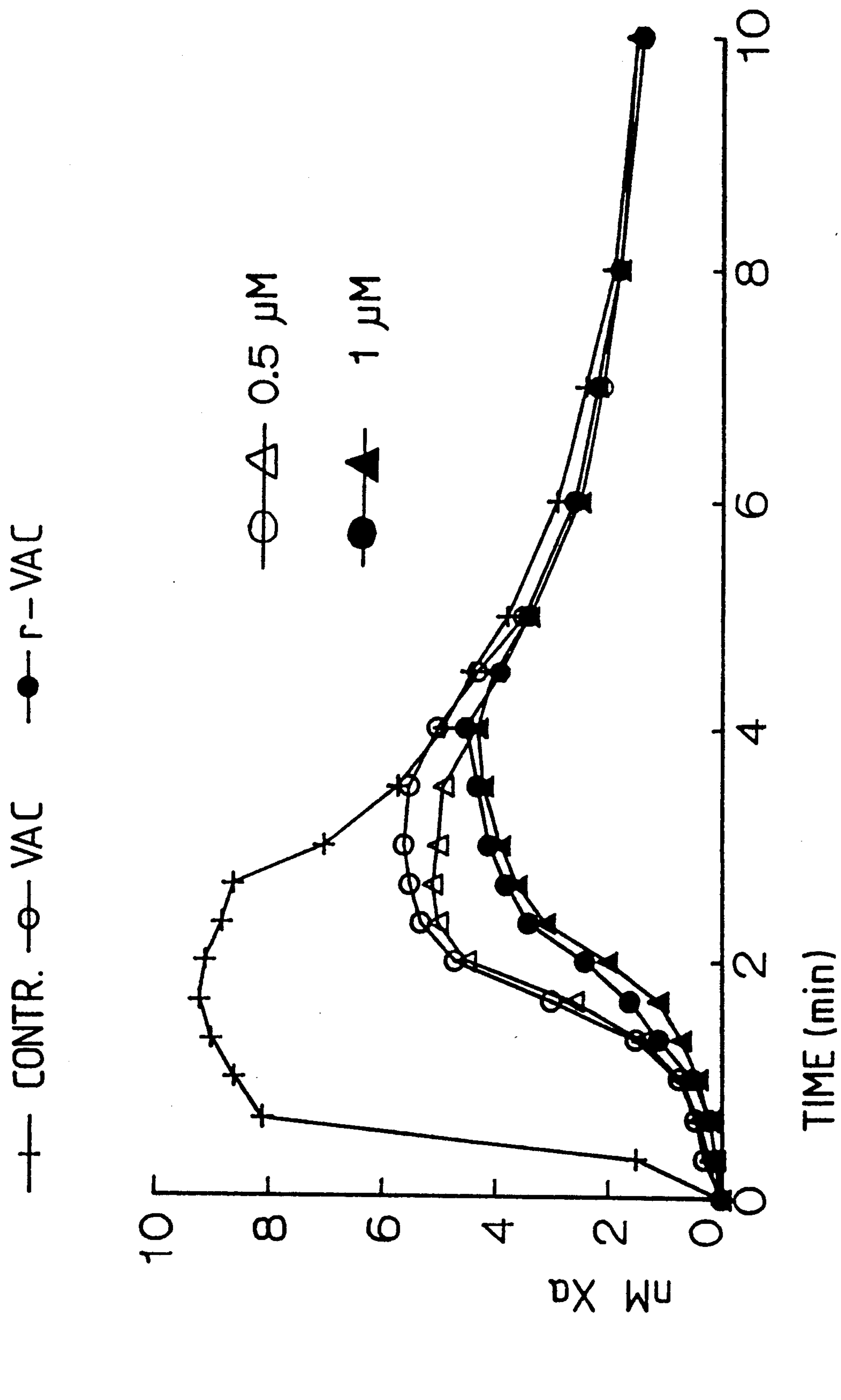
FIG. 41 depicts factor Xa formation in plasma by natural and recombinant VAC.

The expressed proteins were detected, for example, by Western blot. The results are shown in FIGS. 25*a* and 25*b*.

"+phosphate" is the control withou any expression, "−phosphate" indicates the expression of VAC-alpha (clone HR101/pRH291) or VAC-beta (clone HB101/pRH292) protein under the control of the alkaline phosphatase promoter. Roth VAC-alpha and VAC-beta protein can already be detected on the stained gel. The quantity of VAC proteins formed is, surprisingly, at least 20 mg/l/$OD_{600nm}$ bacterial culture.

The Western blot clearly shows the stained VAC-alpha band. In addition, some proteins of lower molecular weight can be seen in the range up to 30 kD, possibly formed by proteolytic cleavage at the N and/or C terminus of the VAC-alpha protein. Another noticeable feature is a protein recognized by the antiserum in the range below 20 kD, which could be a half molecule of VAC-alpha protein formed by proteolysis. Surprisingly, VAC-beta was also recognized by anti-VAC antiserum. Since this band is much more faintly colored than the VAC-alpha band but the VAC-beta band in the Coomassie Blue stained gel corresponds to the VAC-alpha in its intensity, it can be concluded that recognition of the VAC-beta protein by the anti-VAC antiserum is substantially poorer than recognition of the VAC-alpha protein.

In order to isolate and purify the expressed proteins, the frozen biomass was suspended in a suitable lysis buffer. The cells were then mechanically destroyed, for example using a Manton-Gaulin press. After the addition of a precipitating agent for non-protein constituents such as polyethyleneimine the solid components were removed, for example, by centrifuging. After the proteins had been precipitated, preferably by ammonium sulphate fractionation, dissolving of the precipitate, removal of the precipitation agent and clarification of the solution, the extract thus obtained was subjected to various chromatographic purification steps. Instead of the precipitation of the proteins the crude VAC extract can also be purified by chromatographic preliminary purification so that it can then be subjected to a purification cycle. $SiO_2$ has proved suitable, for example, as a column material for the preliminary purification, but other materials with similar properties are also suitable. Silica Catalyst Carrier, grade 953Tv made by Messrs Grace was used.

A chromatographic purification cycle suitable for purifying the proteins consisted of for example a DEAE fast flow Sepharose, a Sephacryl S-200 High Resolution and a Q-Sepharose Fast Flow Chromatography. The purity of the proteins thus obtained was determined by SDS-PAGE, Western blot, gel permeation HPLC, reverse HPLC and isoelectric focussing.

The parameters which have to be adhered to for all the steps of cultivation, isolation and purification, such as temperature, ratios of quantities, sequence of the individual steps, pH values, particular reagents, etc. are known to those skilled in the art. The examples which follow may, if desired, be suitably modified in a manner known to the person skilled in the art.

It is particularly important to determine whether a VAC protein produced by genetic engineering and hereinafter referred to as r-VAC for short, is identical to the VAC protein obtained from natural material (see EPO 0 181 465), hereinafter referred to as VAC, identical both in its structure and its biological properties.

The following methods were used to answer these questions:

1. gel permeation HPLC
2. reverse phase HPLC
3. N-terminal sequencing
4. tryptic peptide map
5. SDS gel electrophoresis
6. Western blot
7. isoelectric focussing The gel permeation HPLC shows a molecular weight of 34,000 for VAC and 33,000 for r-VAC, which can be regarded as equivalent within the range of accuracy of the method. It should be born in mind that strictly speaking the column used differentiates not according to molecular weight buy according to molecular size.

In reverse phase HPLC, both proteins elute after a retention time of about 29 minutes.

N-terminal sequencing of the r-VAC up to amino acid 39 showed a 100% agreement with the expected sequence. N-terminal methionine, often additionally found in proteins produced by genetic engineering, could not, surprisingly, be detected. As expected, the N-terminus of r-VAC is present in unblocked state.

A comparison of tryptic fragmentation showed a virtually identical peptide pattern.

A comparison of the two proteins by SDS-PAGE also showed virtually identical behavior. Both contain dimeric forms which are obviously bound via disulphide bridges and can be reduced by dithiothreitol.

Similarly immunological comparison by Western blot confirmed that the two proteins were identical.

The difference of +0.1 pH units in r-VAC found when determining the isoelectric point can be explained by the free N-terminus.

To check the biological activity of r-VAC, various coagulation tests were carried out and the results were compared with those which are obtained with VAC from natural material. All the tests carried out, the modified prothrombin time test and the thrombin test, as well as the factor $X^a$ generation in tissue factor-activated plasma clearly prove that r-VAC has biological activity and that this is indistinguishable from that of VAC from natural material.

Tests have shown that disulphide bridges have nothing to do with the coagulation-inhibiting activity of natural VAC. Depending on the choice of host cell, it cannot be ruled out that the cysteine groups will become linked in the primary translation product, forming disulphide bridges, in a way which differs from the naturally occurring process. It is possible that the "false" tertiary structure of the product established will lead to a reduction in or even loss of, but possibly an improvement in, the valuable pharmacological properties, particularly the coagulation-inhibiting activity, and this can be determined using the above-mentioned VAC assays. In such cases it may be convenient to cleave the disulphide bonds with a suitable reducing agent and to treat the reduced polypeptide with a suitable oxidizing agent to re-form the disulphide bonds. Using the VAC activity of the product formed it is possible to determine whether the conditions selected (reducing and/or oxidizing agent) have resulted in the desired increase in biological activity or whether the conditions have to be modified in known manner.

Examples of suitable reducing agents for cleaving disulphide bridges include thiol compounds such as thiophenol, 4-nitrothiophenol, 1,4-butanedithiol and particularly 1,4-dithiothreitol. The reduction is advantageously carried out in an aqueous/alkaline medium, for example in a dilute aqueous solution of an alkali metal hydroxide, e.g., sodium hydroxide, alkali metal carbonate, e.g., sodium carbonate, or an organic base, particularly a tri-lower alkylamine, e.g., triethylamine, at ambient temperature.

Oxidizing agents which are suitable for re-forming disulphide bonds in the reduced polypeptides include, for example, oxygen from the air, which is passed through an aqueous solution of the polypeptide, to which, if desired, a catalytic quantity of a salt of a transition metal has been added, e.g., iron(III) sulphate, iron (III) chloride or copper (II) sulphate; iodine, also in the form of the potassium iodine adduct $KI_3$, which is used in alcoholic, e.g., methanolic, or aqueous-alcoholic, e.g., aqueous-methanolic solution; potassium hexacyanoferrate (III) in aqueous solution; 1,2-diiodoethane or dimethyl or diethyl azodicarboxylate, which are reacted in water or in a mixture consisting of water and a water-miscible alcohol, e.g., methanol. The oxidation is carried out, in particular, at ambient temperature.

The separation of the reagents, particularly the salts and the oxidizing or reducing agents and their secondary products from the desired VAC compound is effected by methods known per se, for example by molecular weight filtration, e.g., using Sephadex or Biogel.

A mixture of compounds with VAC activity obtainable according to this process can be separated into the individual components in known manner. Suitable methods of separation include, for example, chromatographic methods such as adsorption chromatography, ion exchange chromatography, HPLC or reverse phase HPLC, and also multiplicative distribution or electrophoretic methods, e.g., electrophoresis on cellulose acetate or gel electrophoresis, particularly polyacrylamide gel electrophoresis ("PAGE").

To simplify the following Examples, any methods which recur frequently are described in abbreviated form.

Plasmids are written with a small "p", followed by capital letters and numbers. Starting plasmids are commercially obtainable or pubicly available without restriction. They may also be constructed from such plasmids using published methods.

The "cutting" or "digestion" of DNA refers to the catalytic cleavage of the DNA by means of restriction endonucleases (restriction enzymes) at specific sites for this purpose, known as restriction sites. Restriction endonucleases are commercially available and are used under the conditions recommended by the manufacturers (buffer, bovine serum albumin (BSA) as carried protein, dithiothreitol (DTT) as antioxidant).

Restriction endonucleases are written with a capital letter, usually followed by small letters and normally a Roman numeral. The letters depend on the microorganism from which the restriction endonuclease in question was isolated (for example: SmaI: *serratia marcescens*). Usually, approximately 1 mcg of DNA is cut with one or more units of the enzyme in about 20 mcl of buffer solution. Normally, an incubation period of 1 hour at 37° C. is used, but may vary depending on the instructions for use provided by the manufacturer. After the cutting, the 5' phosphate group is sometimes removed by incubation with alkaline phosphatase from calves' intestines (CIP). This serves to prevent undesired reactions of the specific site in a subsequent ligase reaction (e.g., circularization of a linearised plasmid without insertion of a second DNA fragment). Unless otherwise stated, DNA fragments are normally not dephosphorylated after cutting restriction endonucleases. The reaction conditions for incubation with alkaline phosphatase may be found, for example, in the M13 Cloning and Sequencing Handbook (Cloning and Sequencing Handbook, published by Amersham, PI/129/83/12). After incubation, protein is eliminated by extraction with phenol and chloroform and the DNA is precipitated from the aqueous phase by the addition of ethanol.

"Isolation" of a specific DNA fragment indicates that the cut DNA is separated on a 1% agarose gel, for example. After electrophoresis and making the DNA visible in UV light by staining with ethidium bromide (EtBr), the desired fragment is located by means of molecular weight markers which have been applied and bound to DE 81 paper (Schleicher and Schüll) by further electrophoresis. The DNA is washed by rinsing with low salt buffer (200 mM NaCl, 20 mM Tris pH=7.5, I mM EDTA) and then eluted with a high salt buffer (1 M NaCl, 20 mM Tris pH=7.5, 1 mM EDTA). The DNA is precipitated by the addition of ethanol. "Southern Analysis" is the method by which the presence of a specific DNA fragment in a DNA mixture is demonstrated by hybridization with a known, labelled oligonucleotide probe or a labelled DNA fragment. Unless otherwise specified, Southern Analysis hereinafter means the separation of the DNA mixture on a 1% agarose gel, denaturing and transfer to nitrocellulose filters (Schleicher and Schüll, BA 85) using the method of E. Southern. *J. Mol. Biol.* 98:503-517 (1978), and hybridization as described in Hauptmann et al., *Nucleic Acids Res.* 13:4739-4749 (1985).

"Transformation" refers to the introduction of DNA into an organism so thatthe DNA can be replicated therein, either extra-chromosomally or as a chromosomal integrant. Transformation of *E. coli* follows the method specified in the M13 Cloning and Sequencing Handbook (Cloning and Sequencing Handbook published by Amersham, PI/129/83/12).

"Sequencing" of a DNA indicates the analysis of the nucleotide sequence in a DNA. To do this, the DNA is cut with various restriction enzymes and the fragments are introduced into correspondingly cut M13 mp8, mp9, mp18 or mp19 double-stranded DNA, or the DNA is introduced by ultrasound, subsequent repair of the ends and size selection into SmaI cut, dephosphorylated M13 mp8 DNA (by the shotgun method). After the transformation of *E. coli* JM101, single stranded DNA is isolated from recombinant M13 phages in accordance with the M13 Cloning and Sequencing manual (Cloning and Sequencing Handbook, published by Amersham, PI/129/83/12) and sequenced by Sanger's dideoxy method (Sanger et al., *Proc. Natl. Acad. Sci.* 74:5463-5467 (1977)). The evaluation of the sequences is carried out using the computer programs originally developed by R. Staden (Staden, *Nucleic Acids Res.* 10:4731-4751 (1982)) and modified by Ch. Pieler (G. Pieler 1987, Dissertation, University of Vienna).

"Ligation" relates to the process of forming phosphodiester bonds between two ends of double stranded DNA fragments. Usually, between 0.02 and 0.2 mcg DNA fragments in 10 mcl are ligated with about 5 units of T4-DNA ligase ("ligase") in a suitable buffer solution (Maniatis et al., *Molecular Cloning,* 1982, page 474).

"Preparation" of DNA from transformants means the isolation of the plasmid DNA from bacteria using the alkaline SDS method modified according to Birnboim and Doly (Maniatis et al., *Molecular Cloning,* 1982, pp. 368-369) omitting the lysozyme. The bacteria from a 1.5 to 50 ml culture are used.

"Oligonucleotides" are short polydeoxynucleotides which are synthesized chemically. The Applied Biosystems Synthesizer Model 381A was used for this. The oligonucleotides are worked up in accordance with the model 381A User Manual (Applied Biosystems) and purified by polyacrylamide gel electrophoresis (PAGE).

"Phosphorylation" means the enzymatic transfer of the gamma-phosphate group from ATP to a free 5'OH group of a nucleic acid, usually an oligonucleotide. In 10 mcl of solution, up to 100 pMol of the oligonucleotide are phosphorylated with 10 units of T4 polynucleotide kinase in the presence of 100 pMol of ATP in suitable buffer solution (70 mM Tris, pH=7.6, 10 mM $MgCl_2$, 5 mM DTT) for 30 minutes at 37° C. The reaction is usually stopped by heating to 100° C. for 10 minutes.

Some of the abbreviations used will now be defined:

bp: base pairs
BSA: bovine serum albumin
DTT: dithiothreitol
EDTA: ethylenedinitrilotetraacetic acid, disodium salt
SDS: sodium dodecylsulphate
Tris: Tris (hydroxymethyl)-aminomethane
Denhardt: 0.02% Ficoll, 0.02% polyvinylpyrrolidone, 0.02% BSA
LB: 10 g/l tryptone, 5 g/l yeast extract, 5 g/l NaCl
Ix SSC: 150 mM NaCl, 15 mM trisodium citrate, pH=7

TE: 10 mM Tris pH=8.0, 1 mM EDTA--

Moreover, it was surprisingly found that the VAC absorption on phospholipids is influenced to an exceptionally positive degree on the presence of $Ca^{2+}$ and $Zn^{2+}$ ions which improves the anticoagulant effect of VAC.

The present invention therefore also relates to a pharmaceutical composition containing a combination of a vascular anticoagulant selected from the group comprising the annexines and the naturally occurring or synthetically produced or genetically engineered derivatives or analogs thereof as well as $Ca^{2+}$ and $Zn^{2+}$ and optionally excipients and/or carriers and/or stabilizers.

The invention also relates to pharmaceutical compositions comprising aggregated annexines and at least one bivalent cation def ined above, wherein at least two annexines are linked by at least one disulfide bridge between the cysteine groups. For example, the cysteine groups at position 316 of two annexines having Formula (I) may be linked via a disulf ide linkage. Alternatively, any one of the cysteines at positions 161, 206, 250 and/293 of two or more annexines having Formula (II) may be linked via a disulfide group. Of course, intra-disulfide linkages are also contemplated.

The bivalent cations selected from the group $Ca^{2+}$ $Cd^{2+}$, $Zn^{2+}$, $Mn^{2+}$ or $Co^{2+}$ are administered as part of the pharmaceutical composition at a concentration ranging from 0.01 to 100 mM, preferably from 0.03 to 10 mMol. It is preferable that the bivalent cation is administered at a concentration corresponding to the normal plasma concentration of the respective bivalent cation. Such normal concentrations are well known to those of ordinary skill in the art.

In order to achieve the synergistic effect of $Zn^{2+}$ ions, is present in the pharmaceutical composition at a concentration between 0.1 and 100 μM, preferably between 18 and 30 μM and, more preferably, it is in the range of the normal plasma zinc concentration.

In cases where there is a calcium and/or zinc deficiency, the calcium and/or zinc concentration is at least adjusted so as to attain at least the normal plasma level of the respective bivalent cation.

The anticoagulants which may be used according to the invention, particularly VAC, may occur not only in free form but also in the form of the salts thereof, particularly the pharmaceutically acceptable salts thereof. Since they contain a plurality of amino acid groups with free amino groups, the compounds according to the invention may be present, for example, in the form of acid addition salts. These acid addition salts may be, in particular, physiologically acceptable salts with conventional, therapeutically usable acids; examples of inorganic acids are the hydrohalic acids such as hydrochloric acid, as well as sulfuric and phosphoric or pyrophosphoric acid; examples of organic acids include, primarily, sulfonic acids such as benzenesulfonic or p-toluenesulfonic acid or lower alkanesulfonic acids such as methanesulfonic acid, as well as carboxylic acids such as acetic acid, lactic, palmitic, stearic, malic, tartaric, ascorbic and citric acid. Since the compounds also contain amino acid groups with free carboxyl groups, they may also occur as metal salts, particularly as alkali or alkaline earth metal salts, e.g. sodium, calcium or magnesium salt or as ammonium salt derived from ammonia or a physiologically acceptable, organic nitrogenous base. However, since they also contain free carboxyl groups and free amino groups, they may also occur as internal salts.

The new pharmaceutical compositions according to the invention may be used, analogously to VAC, for the treatment and prevention of thromboses and enbolism, including the prevention of post-operative thromboses, in acute shock therapy (e.g. in septic or polytraumatic shock), for the treatment of exhaustion coagulopathies particularly where there is a calcium and/or zinc deficiency, in hemodialysis, hemoseparations, stored blood and in extracorporeal circulation.

The pharmaceutical compositions according to the invention may also be used therapeutically and/or prophylactically in all intravasal manipulations in which damage may occur to the walls of blood vessels and as a result clots may be produced in a number of cases. These intravasal manipulations include for example balloon catheterization, arterial/venous prostheses and the removal of arterioscierotic plaques, e.g. by laser beams.

The compositions may, for example, be administered parenterally, e.g. intravenously, intracutaneously, subcutaneously or intramuscularly or by topical route.

The dosage will depend on the purpose of the therapy or preventive treatment. The size of the individual doses and the plan of administration can best be determined by individual assessment of the particular case: the methods needed to determine the relevant factors are well known to anyone skilled in the art. In normal cases, the therapeutically effective quantity of the annexine according to the invention, when injected, will be within the dosage range of about 0.005 to 0.1 mg/kg of body weight. The range from about 0.01 to about 0.05 mg/kg of body weight is preferred.

The anticoagulant pharmaceutical composition may be administered by intravenous, intramuscular or subcutaneous injection. Accordingly, pharmaceutical preparations for parenteral administration in the form of a single dose contain about 0.4 to 7.5 mg of the anticoagulant per dose, depending on the method of administration. As well as the combination of annexine and at least one bivalent cation according to the invention, these pharmaceutical compositions may optionally also contain a buffer, e.g. a phosphate buffer which is intended to keep the pH at between 3. 5 and 8, and also sodium chloride, mannitol or sorbitol to adjust the solution to isotonic. They may be present in freeze-dried or dissolved form, whilst solutions may contain an antibacterially active preservative, e.g. 0.2 to 0.3% of methyl or ethyl 4-hydroxybenzoate. A preparation for topical use may be presented as an aqueous solution, lotion or gel, an oily solution or suspension or a greasy or, more particularly, emulsified ointment. A preparation in the form of an aqueous solution is obtained, for example, by dissolving the combination according to the invention in an aqueous buffer solution at pH 4 to 6.5 and if desired adding another active substance, e.g. an anti-inflammatory agent, and/or a polymeric binder, e.g. polyvinyl-pyrrolidone, and/or a preservative. The concentration of active substance is about 0.1 to about 1.5 mg, preferably 0.25 to 1.0 mg, in 10 ml of a solution or 10 g of a gel.

An oily preparation for topical use is obtained for example by suspending the combination according to the invention in an oil, optionally with the addition of swelling agents such as aluminum stearate and/or surface active agents (surfactants), the HLB value (hydrophilic-lipophilic-balance) of which is less than 10, such as fatty acid monoesters of polyhydric alcohols, e.g. glycerol monostearate, sorbitan monolaurate, sorbitan monostearate or sorbitan monooleate. A greasy ointment is obtained for example by suspending the combination according to the invention in a spreadable grease base, optionally with the addition of a surfactant with an HLB value of less than 10. An emulsified ointment is obtained by triturating an aqueous solution of the combination according to the invention in a soft, spreadable grease base with the addition of a surfactant the HLB value of which is below 10. All these topical preparations may also contain preservatives. The concentration of the active substance is 0.1 to 1.5 mg, preferably 0.25 to 1.0 mg, in about 10 g of the base.

In addition to the pharmaceutical compositions described above and their analogs which are intended for direct medical use on the bodies of humans or mammals, the present invention also relates to pharmaceutical compositions and preparations (referred to as pharmaceutical compositions throughout the present application) for medical use outside the living body of humans or mammals. Such compositions and preparations are used primarily as a coagulation-inhibiting additive in blood which is subjected to circulation or treatment (e.g. extracorporeal circulation or dialysis in kidney machines), storage or modification (e.g. hemoseparation) outside the body. In their composition, preparations of this kind such as solutions for storage or preparations in the form of single doses are similar to the injectable preparations described above; however, the quantity or concentration of the active substance is expediently based on the volume of the blood which is to be treated. Depending on the specific purpose the suitable dose will be about 0.01 to 1.0 mg of active substance per liter of blood, whilst it is quite safe to exceed the upper limit of both active substance and bivalent cations.

It is intended that any animal may be treated with the pharmaceutical compositions of the present invention. Preferably, such animal is a human, however, the invention is not intended to be so limited.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLES Materials and Methods

VAC was prepared as described herein. The experiments which follow were carried out with VACα, but the results can also be transferred to the other annexines, particularly VACβ.

EXAMPLE 10

The material isolated from umbilical cord vessels and/or placenta and then purified was repurified by reverse phase HPLC.

| | |
|---|---|
| Stationary phase: | Bakerbond WP-RP 18, 4.6 × 250 mm, 5 mcm particles, 300 A pores |
| Mobile phase A: | 0.1% trifluoroacetic acid in water, pH 2.2 |
| Mobile phase B: | 0.1% trifluoroacetic acid in acetonitrile |
| Gradient: | 20-68% B in 24 min. |
| Flux: | 1 ml/min |
| Detection: | UV, 214 nm |

After this purification step, both materials, both being substances with a molecular weight of 32,000, were digested with trypsin.

| | Reaction conditions |
|---|---|
| | 30 mcg of VAC from placenta were reacted in 135 mcl of 0.15 M $NH_4HCO_3$, pH 8.0 |
| + | 2% w/w trypsin (Worthington) for 6 hours at 37° C. |
| + | 2% w/w trypsin (Worthington) overnight at 37° C. |
| | 30 mcg of VAC from umbilical cord were reacted in 100 mcl of 1% $NH_4HCO_{31}$ pH 8.0 |
| + | 2% w/w trypsin (Worthington) for 6 hours at 37° C. |
| + | 2% w/w trypsin (Worthington) overnight at 37° C. |

The fragments obtained were separate by HPLC and subjected to sequencing with a gas phase sequenator Type 470A made by Applied Biosystems, Program 02 RPTH.

| HPLC Separation conditions: | |
|---|---|
| Stationary phase: | μBondapak Cl8, 3.8 × 300 mm, 10 mc particles |
| Mobile phase A: | 0.1% trifluoroacetic acid in water, pH 2.2 |
| Mobile phase B: | 0.1% trifluoroacetic acid in acetonitrile |
| Gradient: | 0-55% B in 55 min |
| Flux: | 1 ml/min |
| Detection: | UV, 214 nm (upper trace) 280 nm (lower trace) |

In addition to tryptic digestion, the material purified by reverse phase HPLC was also subjected to BrCN cleavage. These cleavage peptides were also sequenced and compared with the data relating to the peptides from the tryptic digestion.

BrCN cleavage:

111 mcg of VAC purified by RP-HPLC were dissolved in 111 mcl of 70% formic acid. This already contained a 250fold molar excess of BrCN (90 mcg). Incubation was effected in the dark for 17 hours at ambient temperature. 100 mcl were used for the HPLC separation.

| | |
|---|---|
| HPLC column: | μBondapak C18 |
| Mobile phase A: | 0.1% trifluoroacetic acid in water |
| Mobile phase B: | 0.1% trifluoroacetic acid in acetonitrile |
| Gradient: | 0-70% B in 70 min |
| Flux: | 1 ml/min |
| Detection: | UV, 214 and 280 nm |

Comparison of the results thus obtained and analysis by gel permeation HPLC and SDS gel electrophoresis proves that VAC from placenta and VAC from umbilical cord are identical.

| | |
|---|---|
| Gel permeation HPLC: | |
| Stationary phase: | Waters 1-125, 7.8 × 600 mm, 10 mcm particles |
| Mobile phase: | 0.5 M $Na_2SO_4$, 0.02 M $Na_2PO_4$, pH 7.0, 25% propyleneglycol, 0.04% Tween 20 |
| Flux: | 0.5 ml/min |
| Detection: | UV, 214 nm |
| SDS gel electrophoresis | |
| SDS gel: | 15% |
| Gel thickness: | 0.7 mm |
| Electrophoresis conditions: | 20 mA/plate, 2-3 hours' running time |
| Staining: | Coomassie Blue |
| Probes: | 8 mcg of VAC from umbilical cord or 7 mcg |

-continued

| of VAC from placenta |
|---|

EXAMPLE 1

Preparation of a Human Placental cDNA Library a) Total RNA isolation from placenta GT: 5 M guanidinium thiocyanate, 50 mM Tris pH=7.4, 25 mM EDTA. Before use 8% (v/v) of beta-mercaptomethanol are added. 20 ml of GT are cooled on ice for 5 to 10 minutes before use, the GT should not be precipitated during this time.

GH: 6 M guanidiun hydrochloride, 25 mM EDTA, 10 mercaptoethanol, pH=7.0. Cooling with ice 1 g of deep frozen and mechanically powdered placenta are mixed in 20 ml of GT (0° C.) for 20 seconds at maximum speed using a Polytron (Brinkmann). The volume of the homogenized mixture is determined, it is poured into 0.3 vol of ethanol (−20° C.), mixed and immediately centrifuged at 12,000 rpm 5' at −10° C. (Beckman JA 21 centrifuge, JS13.1 rotor). Any protein film and the supernatant are removed. 10 ml of ice cold GH are added to the pellet and homogenized for 10 seconds using the Polytron. The suspension is centrifuged for 5 minutes at −10° C. and at 12,000 rpm. The supernatant is transferred into a sterile Corex tube and the pellet is discarded. 0.025 vol of 1 M acetic acid and 0.75 vol of cold ethanol (−20° C.) are added to the supernatant and mixed thoroughly. After about 2 hours' incubation at −20° C. the mixture is centrifuged for 10 minutes at 6000 rpm at −20° C. (JA20 Rotor). The protein film and supernatant are carefully removed. 2 ml of GH (0° C.) are added to the pellet, the pellet is resuspended and the suspension is transferred into a 15 ml Corex tube. The old Corex tube is rinsed out with another 8 ml of GH, and the solution is combined with the 2 ml. It is important that the entire pellet be suspended and if necessary it should be subjected to subsequent treatment by mild sonication. 0.025 vol of 1 M acetic acid and 0.5 vol of cold ethanol (−70° C.) are added and incubated for about 2 hours at −20° C. Centrifugation (6000 rpm, 10 min, JA20 rotor), dissolving and precipitation are repeated twice, the total quantity of GH being halved to 5 ml. After the last centrifugation no film of protein should be visible above the solution, otherwise this purification step must be repeated. The pellet is vortexed for 2 minutes with 5 ml of diethyl procarbonate-treated water (0° C.). The clear solution is decanted, some more water is added to any pellet residues remaining and vortexing is continued until the solution is clear. By the addition of 0.1 vol of 3 M Na-acetate (pH=5.8), 2.5 vol of ethanol and 1 hours incubation at 0° C. at −70° C. the RNA is centrifuged off for 10 minutes at 6000 rpm and at 4° C. Dissolving and precipitation are repeated once. Finally, the RNA is stored in ethanol at −20° C.

b) poly-A+-RNA isolation 0.5 mg of oligo dT cellulose (Collaborative Research, Type 3, binding capacity: 5 mg poly-A+ RNA/g) are suspended in binding buffer (200 mM NaCl, 0.2% SDS, 10 mM Tris, pH=7.4, 1 mM EDTA). 1 ml of this suspension is packed into a column and washed successively with 10 ml of water, 10 ml of 0.1 N NaOH, 10 ml of water and finally 10 ml of binding buffer. The total RNA is pelleted out of the alkaline solution by centrifuging (10 min., 6000 rpm, JA20 rotor). About 10 mg of RNA are dissolved in 4.5 ml of water. After the addition of 50 mcl of 2% SDS, the solution is heated to 70° C. for 3 minutes and immediately cooled on ice. After the addition of 50 mcl of 1 M Tris (pH=7.4), 10 mcl of 0.5 M EDTA and 200 mcl of 5 M NaCl the solution is immediately added to the column. The solution dripping out of the column is poured back into the column. This procedure is repeated three times in all. The column is then washed with 30 ml of binding buffer. The bound RNA is eluted with 5 ml of 0.2% SDS. The column is washed with 10 ml of water, 10 ml of 0.1 N NaOH and 10 ml of $H_2O$ and equilibrated with 10 ml of binding buffer. The RNA solution is heated to 70° C. for another 3 minutes, rapidly cooled on ice, 50 mcl of 1 M Tri5 pH=7.4, 10 mcl of 0.5 EDTA and 200 mcl of 5 M NaCl are added and the resulting solution is poured onto the column. The solution running through is poured back into the oligo-dT column three times in all. After washing, the RNA is eluted with 30 ml of 0.2% SDS.

By the addition of 0.1 vol of 3M Na-acetate pH=5.6 and 2.5 vol of ethanol and incubation at −20° C. (16 hours) the RNA is precipitated. It is centrifuged off (10,000 rpm, 15 min., JA-20 Rotor) and dissolved in water at a concentration of 1 mcg/mcl.

c) Construction of the lambda-gt10 cDNA library

Synthesis of the cDNA, methylation of the internal EcoRI sites, the application of EcoRI linkers, the recutting with EcoRI, the removal of the short DNA fragments, the ligation with the lambda-gt10 arms and the packaging of the ligated DNA in vitro were effected using the cDNA synthesis system made by Amersham (RPN 1256) and the cDNA cloning system lambda-gt10 (Amersham, RPN 1257). The operating procedures supplied with the systems were adhered to exactly. Starting from about 3 mcg, approximately $0.5\times10^6$ recombinant lambda-gt10 phages were finally obtained from the mRNA.

EXAMPLE 2 cDNA Isolation a) Searching through the lambda-gt10 library with oligonucleotides In order to search through the cDNA library for cDNA coding for VAC protein, two oligonucleotides were synthesized corresponding to the sequences of the tryptic peptide P16/II and one oligonucleotide was synthesized corresponding to the Staph A peptide p20/I/6 (FIG. 7). These oligonucleotides are all mixtures of all the variants which take into account every possibility of coding of the corresponding mRNA. EBI-386 has 512 variations with a chain length of 20 nucleotides and fits the Staph-A peptide P20/I/6. In order to minimize the variation in the oligonucleotide for the tryptic peptide p16/II, two oligonucleotides (20-mers) were synthesized: EBI-387: 128 variations, EBI-388: 64 variations.

Moreover, two oligonucleotides fitting the tryptic VAC peptide p30/I were synthesized using desoxyinosine as the base at "wobble" positions (FIG. 8): EBI-118 and EBI-119. This substitution has been described by Ohtsuka et al., *J. Biol. Chem.* 260/5:2605-2608 (1985), and Takahashi et al., *Proc. Nat. Acad. Sci.* (1985) pp. 1931-1935. Inosine basepairs well with cytosine, but still hardly disturbs the formation of the double helix if other nucleotides are presented as partners.

60 pMol of each oligonucleotide were phosphorylated with 60 pMol of gamma-$^{32}$P-ATP (Amersham, PB 218, 500 Ci/mMol) in 30 mcl of solution using 20 units of $T_4$ polynucleotide kinase. The solution contained 70 mM Tris pH 7.5, 10 mM $MgCl_2$ and 5 mM DTT and the incubation period was 30 minutes. The reaction was stopped by the addition of 30 mM EDTA and heating to 70° C. for 5 minutes. The labelled oligonucleotide was separated from any non-incorporated radioactivity by column chromatography using Biogel P6DG (Riorad). Between 70 and $110\times10^6$ cpm of phosphorus-32 were incorporated for each oligonucleotide.

15 pMol each of EBI-118 and EBI-119 were phosphorylated in 90 mcl with the addition of 45 pMol of gamma-$^{32}$P-ATP (Amersham, PB 218>5000 Ci/mMol) with 10 units of $T_4$ polynucleotide kinase and subsequently purified over Biogel P6DG. A total of $70\times10^6$ cpm of phosphorus-32 were incorporated.

Approximately $1.2\times10^6$ pfu (plaque forming units) recombinant phages of a human placental cDNA library in the phage lambda-gt10 were used to infect *E. coli* C600. About 50,000 phages were plated for each 13.5 cm petri dish (LB, 10 mM $MgSO_4$, 15 g/l Bacto-Agar). When the plaques were virtually confluent, two extracts from each plate were prepared on nitrocellulose filters (Schleicher and Schüll, A 85) (Maniatis et al., *Molecular Cloning,* 1982, pp 320–321). The filters were treated in TE at 10° C. for 3×20 minutes and then washed overnight at 65° C.:

Wash solution:

50 mM Tris pH=8

1 M NaCl 1 mM EDTA 0.1% SDS

The filters were then prehybridized for 4 hours at 49° C.: prehybridizing solution:

6×SSG

5×Denhardt 0.1% SDS 1 mM Na-pyrophosphate 50 mM $NaH_2PO_4$pH=6.S 100 mcM ATP 80 mcg/ml of denatured herring sperm DNA Hybridization was carried out in the same solution using the entire quantity of labelled oligonucleotides. The doubled extracts from plates 1 to 6 were hybridized with EBI-386, those from plates 7 to 12 were hybridized with EBI-387 and EBI-388 for 16 hours at 49° C. The extracts from plates 13 to 24 were hybridized for 16 hours at 37° C. with EBI-118 and EBI-119. After hybridization had been carried out, the filters were rinsed twice with 6×SSC/0.01% SDS, and washed 2×30 minutes at ambient temperature with 6×SSC/0.01% SDS and 3×20 minutes in the same solution at 49° C. and 37° C., respectively. After drying in air, the filters were exposed on Kodak X-Omat S film at −70° C. using intensifier film.

Lambda phages which showed hybridization with the oligonucleotide on both filters were purified for homogeneity using the same hybridization procedure.

The hybridization with EBI-386, 387 and 388 resulted in the phages lambda p11/3, lambda p6/5 and lambda p6/6. Hybridization with EBI-118 and 119 resulted in the phages lambda-Nr15, lambda-Nr119 and lambda-Nr22.

b) Isolation of the cDNA insert

*E. coli* C 600 was infected with $2.5\times10^6$ pfu (plaque forming units) of phages and plated with 6 ml of top agarose (0.7% agarose, 10 mM $MgSO_4$, LB) on 13.5 cm agar dishes (LB, 10 mM $MgSO_4$, 1.5% agarose, 0.2% glucose). After 5½ hours' incubation at 37° C. the plaques were confluent. The plates were cooled for 30 minutes at 4° C. and the agarose was covered with 10 ml of lambda diluent (10 mM Tris, pH=8, 10 mM $MgSO_4$, 0.1 mM EDTA). The phages were eluted overnight at 4° C. with gentle shaking. The supernatant phage suspension (about 8 ml) was transferred to Corex tubes and centrifuged for 10 minutes at 15,000 rpm (4° C., JA 21 centrifuge). The supernatant was decanted into polycarbonate tubes and centrifuged at 50,000 rpm (20° C., L70 Beckman centrifuge, 20° C., 50 Ti Rotor) until omega$^2$t$=3\times10^{10}$ (about 23 minutes). The pelleted phages were resuspended in 0.5 ml of lambda diluent after removal of the supernatant and then transferred into Eppendorf test tubes. The suspension was freed from any unsuspended particles by brief centrifuging and the supernatant was placed in a fresh test tube. After the addition of 10 mcg/ml of RNaseA and 1 mcg/ml of DNase I the mixture was incubated for 30 minutes at 37° C. After the addition of 25 mM EDTA, 25 mM Tris, pH=8, 0.2% SDS, the mixture was incubated for 30 minutes at 70° C. Next, 1 vol of phenol/chloroform (1:1) was added, and proteins were extracted by tilting the test tube. After 2 minutes' centrifugation in the Eppendorf centrifuge the aqueous phase was extracted with 1 vol of chloroform (only by tilting, not by vortexing). After phase separation by centrifugation, 1/20 vol of 3 M Na-acetate and 1 ml of ethanol were added to the supernatant. The DNA phages were thus precipitated in the form of filaments. After 5 minutes' incubation at 0° C. the DNA was removed by centrifuging (10 minutes). The pellet was washed once with 70% ethanol, dried and dissolved overnight in 50 mcl of TE (4° C.). The DNAs were cut with EcoRI and the resulting fragments were separated on a 1% agarose gel. The cDNA inserts of the clones lambda-P11/3, lambda-P6/5 and lambda-P6/6 ranged from about 1300 to 1400 bp in size. Sequence analysis showed all three clones were derived from one and the same mRNA. However, the 5' end of the mRNA was missing from the cDNAs. The inserts of the phages lambda-Nr15, lambda-Nr19 and lambda-Nr22 had lengths of about 1600, 1100 and 1000 bp. Sequence analysis indicated an approximately complete cDNA. The cDNAs of the two phage groups lambda-P11/3, lambda-P6/5 and lambda-P6/6 and lambda-Nr15, lambda-Nr19 and lambda-Nr22 are derived from two different mRNAs, as indicated by the following sequence analysis.

The EcoRI inserts of the three clones lambda-P11/3, lambda-P6/5 and lambda-P6/6 were isolated and ligated into the EcoRI-cut Bluescribe M13+ vector (Vector Cloning Systems, 3770 Tansy Street, San Diego, Calif. 92121, USA). The resulting clones were designated pP6/5, pP6/6 and pP11/3.

The EcoRI inserts of the three clones lambda-Nr15, lambda-Nr19 and lambda-Nr22 were isolated and ligated into the EcoRI-cut Bluescribe M13$^{30}$ vector. The resulting clones were designated pRH201, pRH202 and pRH203.

c) Other VAC cDNA clones

In order to obtain other cDNA clones, the human placental lambda-gt10 library was searched once again, this time using the EcoRI insert of pP11/3 as the probe. This DNA fragment was radioactively labelled by nick translation (T. Maniatis, *Molecular Cloning,* 1982, pages 109–112, no DNase I used). In all, $4\times10^5$ phages on 8 plates were investigated. The treatment of the nitrocellulose filters was carried out as described in T. Maniatis, *Molecular Cloning*, 1982, pages 320–321. The hybridization solution contained 6×SSC, 5×Denhardt's, 0.1% SDS and $20\times10^6$ cpm pP11/3 insert. Hybridization lasted for 16 hours at 65° C. The filters were then washed 3×10 minutes at ambient temperature with 6×SSC/0.01% SDS and 3×45 minutes at 65° C. with 0.2×SSC. In all, 69 positively reacting clones were obtained (lambda-VAC1 to lambda-VAC69).

12 of these clones were prepared on a small scale as described above, the cDNA inserts with EcoRI were freed and separated on a 1% agarose gel. It became apparent that the insert of the clone lambda-VAC10 contains the entire reading frame coding for VAC protein.

EXAMPLE 3

Characterization of the cDNAs coding for VAC-alpha and VAC-beta a) Northern blot experiment 5 mcl of water, 16 mcl of formamide, 6 mcl of formaldehyde and 3 mcl of 0.1 M NaOH were added to 2 mcg of poly-A+ RNA, the solution was incubated for 10 minutes at 68° C. and then cooled on ice. After the addition of 5 mcl of dye solution (0.4% each of bromophenol blue and xylene cyanol in 50% glycerol, 1 mM EDTA) the RNA was separated on a formamide agarose gel (1.5% agarose, 10 mM Na-phosphate pH=7.6, 1 mM EDTA, 5 mM Na-acetate, 6% formaldehyde, electrophoresis 100 V, 3 hours, eluting buffer as gel buffer, without formaldehyde). Total RNA was applied as a reference substance. This trace was taken off after electrophoresis and stained with EtBr in order to determine the position of the 28 and 18 S rRNA. The remainder of the gel was washed twice for 10 minutes in 10×SSC and the RNA was transferred to nitrocellulose filters with 20×SSC. The filter was washed with 2×SSC, dried and baked for 2 hours in vacuo at 80° C. 1 mcg each of pP11/3 and pRH203 were radioactively labelled with the multiprime DNA labelling system (Amersham, RPN 1601). The nitrocellulose filter was prehybridized for 2 hours at 65° C. in 6×SSC/5×Denhart's/0.1% SDS. One trace was hybridized with $180\times10^6$ cpm pP11/3 or pRH203 (16 hours at 65° C.). The filters were washed twice, for 30 minutes at ambient temperature, with 6×SSC/0.01% SDS and twice for 30 minutes at 65° C. with 0.2×SSC/0.01% SDS, dried and exposed on Kodak X-Omat S film with intensifier film.

The results are shown in FIG. 9. The cDNA of the clone pP11/3 hybridizes to an mRNA about 1700 bases long ("VAC-alpha"), whilst the cDNA of the clone pRH 203 hybridizes to an mRNA about2200 bases long ("VAC-beta").

Since, firstly, the quantity of radioactivity used and the amount of mRNA applied per trace were approximately the same and secondly the hybridization of a genome blot in the same solution produced bands of equal intensity with both cDNAs (see below), it can be concluded that the shorter mRNA ("VAC-alpha") is present in placenta in larger quantities than the longer ("VAC-beta") mRNA.

b) Sequence analysis of the VAC-alpha cDNA

The cDNA of clones pP6/5, pP6/6 and pP11/3 were totally sequenced and those of the clones lambda-VAC1 to 12 were partially sequenced. The results are shown in FIGS. 10*a*, 10*b*, 10*c*, 10*d* and 10*e*. In all, 1465 bases were sequenced. The cDNA has a long open reading frame which can code for 320 amino acids. If the DNA sequence is translated into an amino acid sequence, all the sequenced peptides can be accommodated in this sequence (FIGS. 11*a*, 11*b* and 11*c*). Therefore, this cDNA is the one whose corresponding mRNA codes for VAC protein. Since the sequences of the second isolated cDNA (see below) code for a protein which is similar, but different from VAC, the name VAC-alpha is introduced here.

The first ATG codon (bases 35–37) is preceded by a stop codon in the same reading frame. Bases 30 to 38 satisfy the Kozak rule fairly well (M. Kozak, *Nature* 308:241–246 (1984), which gives the consensus sequence near the translation start codon as CC(A/G)-CCAUGG; the corresponding sequence here is TCGCTATGG. The 3' untranslated region is 471 bases long. 15 bases before the start of the poly-A section is the polyadenylation sequence AATAAA (N.J. Proudfoot et al., *Nature* 263:211–214 (1976)). If the poly-A section of the mRNA is reckoned to have chain lengths of 150 to 200 bases, the total length of the mRNA, based on the cDNA sequence, will be 1600–1650. Since a higher value was determined in the Nothern blot experiment, the 5' untranslated region does not appear in complete form in any cDNA.

Unlike all the other cDNA clones, the cDNA of clone pP6/5 has C instead of A at position 100. Consequently, the triplet 98–100 (22nd colon) would change from GAA to GAC and would code for Asp instead of Glu. This deviation may have causes: a) the reverse transcriptase has incorporated a wrong nucleotide, b) they are the transcripts of two allelic genes which differ at this point or c) there are two non-allelic genes which differ at this position.

The long open reading frame codes for a protein with 320 amino acids, of which the Met-1 will probably be cleaved and the following alanine will be blocked at the amino group, possibly by acylation. The calculated molecular weight is 35,896 D and is greater than the weight according to SDS-PAGE. Certainly, the proportion of charged amino acids (Asp, Glu, Lys, Arg, His) at 30.6% (98/320) is well above average compared with the average value of 25.1%. This would explain the different migration behavior of the protein in the SDS-PAGE. Among the strongly charged amino acids, the acidic amino acids (Asp and Glu) are predominant, being 54 in number as against the basic amino acids (Lys and Arg) of which there are 41. This explains the acidic isoelectric point of the VAC-alpha protein (pI=4.4 to 4.8). VAC-alpha contains only one triplet coding for cysteine (amino acid position 316); no typical N-glycosylation site (Asn-XXX-Ser/Thr) is present. Structural analysis of the amino acid sequence (modified according to Pustell, J., et al., *Nucleic Acids Res.* 10:4765–4782 (1982)) shows a fourfold repetition of a sequence 67 amino acids long (FIG. 12), hereinafter referred to as "repeats". Within this sequence, 7 amino acids (10.4%) are preserved in all four repeats, 15 amino acids (22.4%) occur in three of the four repeats and at 28 positions (41.8%) two repeats contain the same amino acid.

A comparison with published data (M.J. Geisow, *FEBS Letters* 203:99–103 (1986); M.J. Geisow et al., *TIBS* 11:420–423 (1986)) surprisingly showed that VAC-alpha therefore belongs to a fairly large group of Ca++ dependent phospholipid binding proteins. A consensus sequence is described (Lys-Gly-fob-Gly-Thr-Asp-Glu-var-var-Leu-Ile-fil-Ile-Leu-Ala-fob-Arg;

fob=hydrophobic, fil=hydrophilic, var=variable), which could have been involved in the $Ca^{++}$ binding (M.J. Geisow et al., *Nature* 320:636–638 (1986)). This sequence occurs in each of the four repeated 67 amino acid long subsequences of the proteins according to the invention (FIG. 12). The 6 amino acid long section at the end of each reneat which consists almost exclusively of hydrophobic amino acids is also noticeable ("oooooo" in FIG. 12).

c) Sequence analysis of the VAC-beta cDNA

The VAC-beta cDNA sequence of clones Nr15, NR19 and Nr22 yielded 1940 bp and merges into a poly-A section (FIGS. 13*a*, 13*b*, 13*c*, 13*d* and 13*e*). 16 bases before the poly-A section is the polyadenylation signal AATAAA. Certainly, this consensus sequence occurs at nucleotide position 1704–1709. It is not known why this sequence is not used as a polyadenylation signal. The sequence additionally required at the 3' end of the AATAAA sequence, namely YGTGTTYY (Gill, A., et al., *Nature* 312:473–474 (1984)) only occurs a relatively long way on (TGTGTTAT, position 1735–1742); it is possible that this is the explanation for nonacceptance of the first polyadenylation sequence.

The cDNA contains a long open reading frame which extends from the start of the cDNA to position 1087. It would contain a coding potential for 362 amino acid. For reasons of analogy with VAC-alpha and owing to the fact that a 34,000 D protein also occurs in the purification of VAC (see EPA 181465) the first methionine codon (ATG, positions 107–109) was taken as the start of translation. The Kozak rule is not so well satisfied here as in the case of VAC-alpha (AAGAGATGG at position 102–110).

The resulting protein (VAC-beta) would be 327 amino acids long. It has 4 cysteine groups (amino acid position 161, 206, 250 and 293) and a potential N-glycosylation site (Asn-Lys-Ser, amino acid position 225–227). The calculated molecular weight is 36,837 (FIG. 15). In VAC-beta, too, there is a larger than average number of charged groups: 97/327 (29.6%) whilst the acidic amino acids (Asp+Glu: 49) predominate over the basic amino acids (Lys+Arg: 42) this would explain the lower molecular weight detected by SDS-PAGE.

VAC-beta also shows an internal repetition of a 67 amino acid long sequence (FIG. 14). Within the sequence, 7 amino acids (10.4%) are preserved in all four repeats, 17 amino acids (25.4%) occur in three of the four repeats, and at 25 positions (37.7%) two repeats contained the same amino acid. VAC-beta also shows high similarity with the 17 amino acid long consensus sequence. The remarks made regarding VAC-alpha also apply to VAC-beta.

d) Genomic Southern blot analysis

Figure 16A:
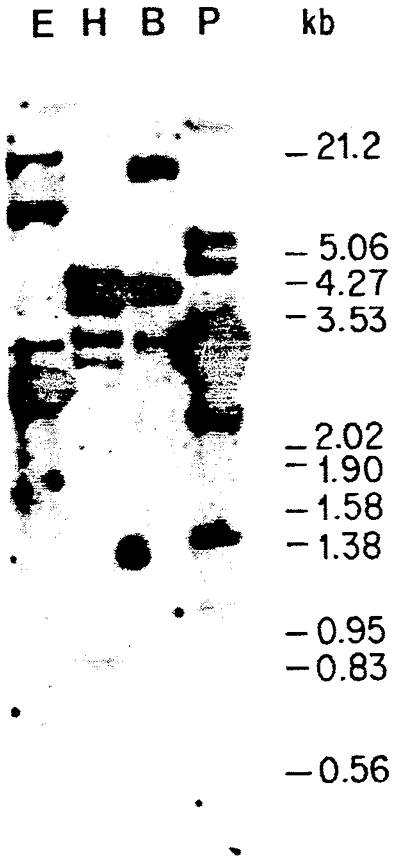
FIGS. 16a and 16b depict a genomic Southern blot analysis with VAC-alpha and VAC-beta cDNA, respectively.
Figure 16B:
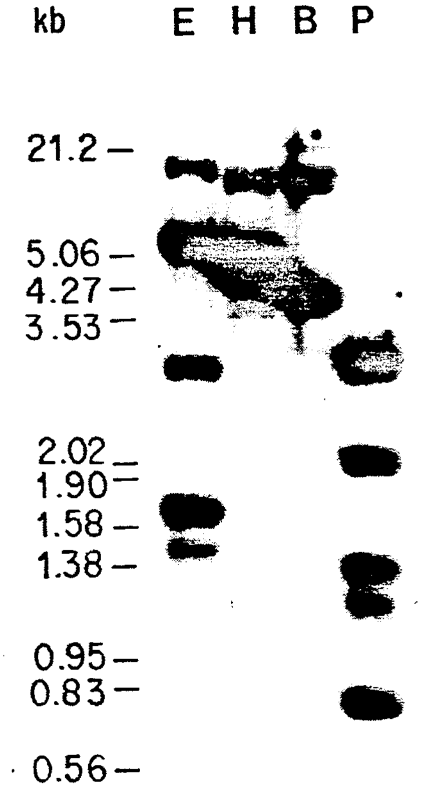

The analysis of chromosomal DNA from human placenta according to Southern shows a complex picture. The DNA has been cut with EcoRI, HindIII, BamHI and PstI. The DNA transferred to nitrocellulose was hybridized both with a VAC-alpha DNA (pP11/3) and also with a VAC-beta DNA (pRH203). The filters were washed under stringent conditions (see point a)), i.e. with 2.0×SSC and 65° C. Nevertheless, a relatively large number of bands appeared on each digestion (FIGS. 16*a*, and 16*b*). Comparison of the two blots showed that the cross reaction of VAC-alpha and beta DNA can probably be ruled out under these conditions. The multiplicity of bands can be explained either by the existence of genes which are similar to the VAC-alpha or VAC-beta gene or it may be a gene which is interrupted by a large number of and/or long introns.

EXAMPLE 4

Protein analysis

FIG. 17 shows a comparison of the amino acid sequences of VAC-alpha and VAC-beta. The repeated sturctures can be arranged identically in both proteins. The connecting peptides are also of the same length with the exception of those between the second and third repeats. In VAC-alpha, a gap must be inserted into this connecting peptide in order to permit optimum matching of the two sequences. The N-terminal peptide of the two proteins is of different lengths, 19 amino acids in the case of VAC-alpha and 25 amino acids in VAC-beta. This peptide also has the lowest homology. The two proteins are identical at 176 of 320 amino acid positions, corresponding to a degree of homology of 55.0%.

At this point, a comparison of the nucleotide sequences of VAC-alpha and beta cDNAs should also be inserted. If two genes and their products are compared with each other, greater homology is seen on the DNA (=RNA) plane than on the amino acid plane, which is explained by the fact that, in the nucleic acid, a change in a base triplet is sufficient to encode a new amino acid.

FIGS. 18*a*18*b* and 18*c* shows a comparison of the coding regions of VAC-alpha and VAC-beta cDNA. Surprisingly, the DNAs show a degree of homology of only 54.2%, i.e. rather less than the two proteins.

Figure 19B:
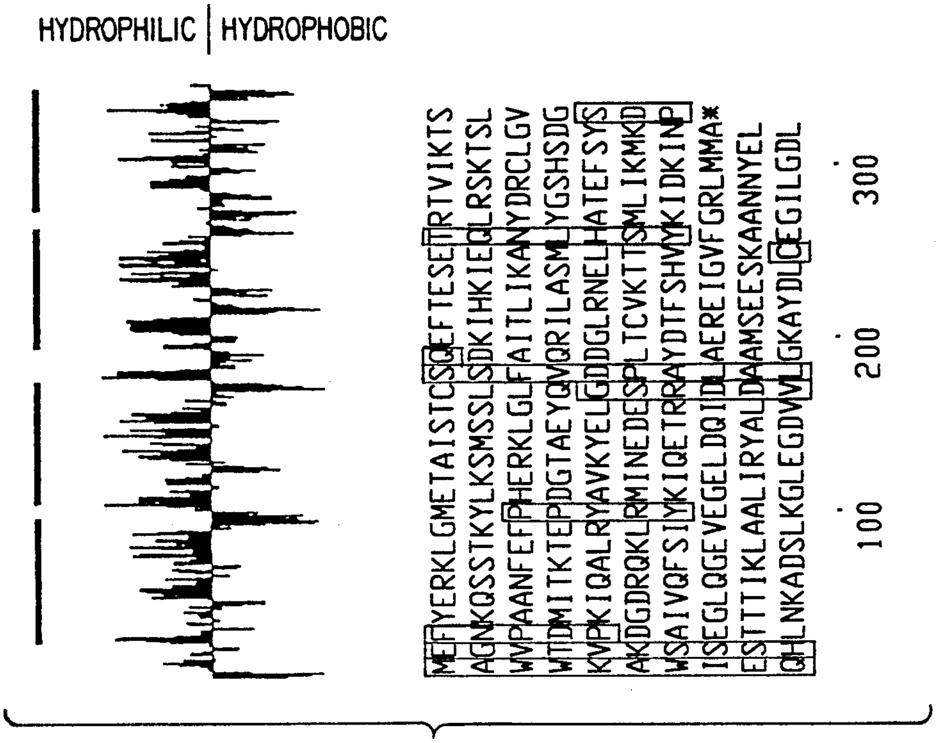
FIGS. 19a and 19b depict hydrophilicity plots of VAC-alpha and VAC-beta respectively.
Figure 19A:
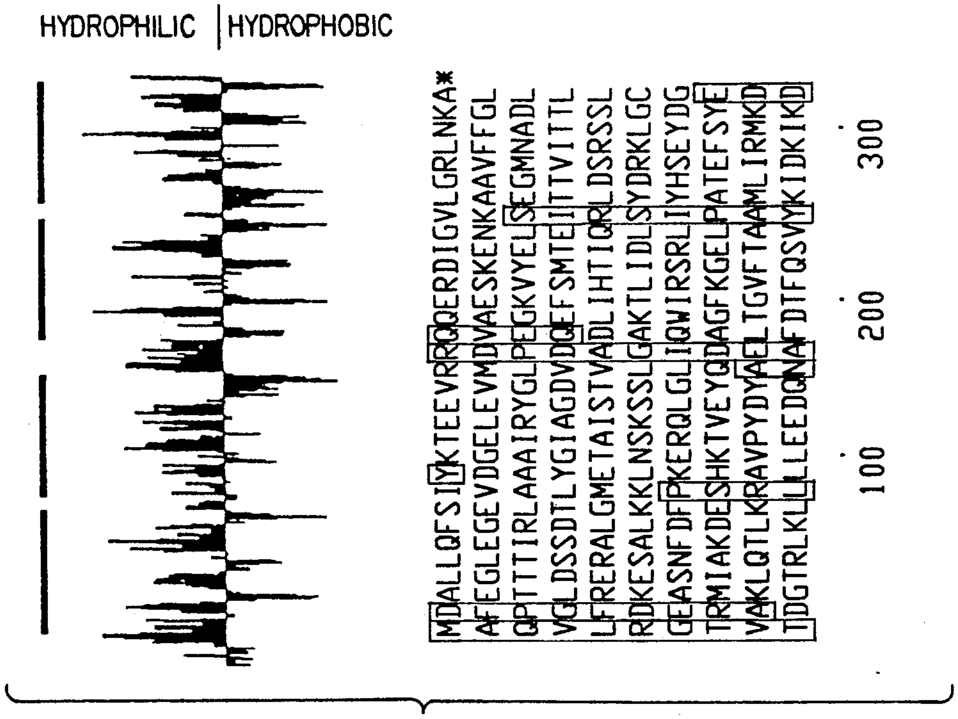

FIGS. 19*a* and 19*b* show the hydrophilicity profiles of the two proteins. The algorithm of Hopp and Wood was used (T.P. Hopp et al., *Proc. Natl. Acad. Sci.* USA 78:3824–3828 (1981)). The four repeat areas are indicated by the bars and the connecting peptides in the sequence below are shown in a frame. It is noticeable that the connecting peptide between the second and third repeats is particularly hydrophilic. In this peptide, both in VAC-alpha and VAC-beta, there is an arginine in the same position. It would therefore be possible for this arginine to be a preferred point of attack for a protease with trypsin-like specificity. The molecule would have to break into two halves of substantially equal size. It would be possible for a "half molecule" of this kind to develop a biological activity, for example an anticoagulant activity. On the other hand, replacement of this arginine by for example histidine might give the VAC-proteins greater stability.

FIGS. 19*a* and 19*b* clearly show that neither VAC-alpha nor VAC-beta has a fairly long hydrophobic region which would enable either secretion through a membrane or storage of the proteins in a membrane. It can therefore be assumed that VAC-alpha and VAC-beta are intracellular proteins.

EXAMPLE 5

Expression of VAC-alpha in *E. coli* a) pRH284T: Expression vector with the alkaline phosphatase promoter and terminator The gene for alkaline phosphatase (PhoA) from *E. coli* is subject to stringent regulation. In the presence of phosphate, the gene is switched off completely and in the absence of phosphate in the medium genetic expression takes place. H. Shuttleworth et al., *Nucleic Acids Res.* 14:8689 (1986); and C.N. Chang et al., *Gene* 44:121–125 (1986), describe the nucleotide sequence of this gene.

The promoter region of the PhoA gene was assembled from several oligonucleotides and inserted in pAT153 cut with EcoRI-ClaI. In front of the ribosomal binding site, an XhoI site was inserted. The original EcoRI site is destroyed when the synthetic DNA fragment is ligated in. After the ribosomal binding site, a translation start ATG was provided, the G of which is the first nucleotide of a SacI (=SstI) site. The expression vector can be linearised by cutting with SacI at this point and the 3′ overhang can be converted into a straight end by treatment with DNA polymerase I-Klenow fragment in the presence of dGTP. In this way, any desired gene may be inserted at this point, and for correct expression it must begin with the first base of the coding region.

The HindIII-SalI fragment of the pAT section was removed and replaced by the alkaline phosphatase transcription terminator. The original SalI site was destroyed. In order to do this, it was reintroduced in front of the terminator together with the BamHI site which had also been deleted from pAT153. The sequence of the synthetically produced DNA is shown in FIG. 21.

b) Expression clone pRH291

The cDNA clone pP6/5 was cut with BglII and PstI and the 980 bp long fragment which contains the majority of the coding region and about 200 bp 3′ untranslated region was isolated. The missing 5′ end of the coding region was replaced by means of oligonucleotides. By two mutations (GGG→GGT, Gly-7 and ACT→ACC, Thr-8), at the same time a KpnI cutting site was introduced into the VAC-cDNA.

The oligonucleotides had the following appearance:

```
| EBI-678                                              | | EBI-677

GCACAGGTTCTCAGAGGTACCGTGACTGACTTCCCTGGATTTGATGAGCGGGCT  3'

CGTGTCCAAGAGTCTCCATGGCACTGACTGAAGGGACCTAAACTACTCGCCCGA

|                                        EBI-680 | |

GATGCAGAAACTCTTCGGAAGGCTATGAAAGGCTTGGGCACAGATGAGGAGAGC

CTACGTCTTTGAGAAGCCTTCCGATACTTTCCGAACCCGTGTCTACTCCTCTCG

                                                    EBI-

            | | EBI-682                                |

ATCCTGACTCTGTTGACATCCCGAAGTAATGCTCAGCGCCAGGAAATCTCTGCA  3'

TAGGACTGAGACAACTGTAGGGCTTCATTACGAGTCGCGGTCCTTTAGAG      5'

 679 | |                                   EBI-681 |
```

The oligonucleotides EBI-680, 677, 678 and 682 were phosphorylated at the 5′ end. EBI-678 and 680, EBI-677 and 679 and EBI-682 and 681 were heated to 100° C. in pairs and slowly cooled (100 pMol in 20 mcl). The double-stranded oligonucleotides were combined and ligated. pRH284T was linearised with SacI, the 3′ overhanging end was reduced to a straight end by treating with DNA polymerase I/Klenow fragment in the presence of dGTP, and then recut with BamHI. About 30 ng of vector, 200 ng of cDNA and 250 nMol of oligonucleotides were ligated in 15 mcl of solution. Competent *E. coli* HB101 were transformed with the ligase solution. The resulting clone was designated pRH291 (FIG. 22).

EXAMPLE 6

VAC-beta expression in *E. coli* a) Expression clone pRH212

The plasmid pERI03 was used as expression vector (E. Rastl-Dworkin et al., *Gene* 21:237–248 (1983)). The vector was linearised with HindIII. The 5′ overhanging end was partly filled in with dATP and DNA polymerase I/Klenow fragment and the remaining single strand residue was digested with 51 nuclease. The vector was recut with BamHI and the large fragment was isolated (FIG. 23). The 440 bp long MaeIII-BamHI fragment which contains codons 13 to 157 was isolated from the clone pRH203. The missing 5′ end was supplemented by the oligonucleotides:

```
EBI-307
5' CCATGGCTTGGTGGAAAGCTTGGATCGAACAGGAAGGT        3'
3' GGTACCGAACCACCTTTCGAACCTAGCTTGTCCTTCCACAGTG  5'
EBI-306
```

Optimum codons for *E. coli* were used (e.g., R. Grantham et al., *Nucleic Acids Res.* 8:1893–1912 (1980)). This codon exchange results in a new HindIII site at codon 5 to 7. The oligonucleotide EBI-306 was phosphorylated, hybridized with EBI-307 and ligated with the VAC-beta fragment. After recutting with BamHI the 5′ terminal VAC fragment was ligated into the prepared pER103 vector. The resulting clone was designated pRH211. To complete the region coding for VAC-beta, the BamHI-SphI fragment 1230 bp long was isolated from the clone pRH201. The pBR322 section, approximately 200 bp long, from BamHI to SphI from the plasmid pRH211 was removed and replaced by the corresponding VAC-cDNA part. This resulted in the clone pRH212. The EcoRI-BamHI fragment which contains the Trp promoter (*S. marcescens*), the ribosomal binding site and the synthetically produced start of the VAC-beta gene was checked by sequencing.

b) Expression of VAC-beta (pRH212)

The plasmid-coded VAC-beta was detected in the Maxicell system (A. Sancar et al., *J. Bacteriol,* 137:692–693 (1979)). *E. coli* CSR603 (F, thr-1, leuB6, proA2, phr-1, recA1, argE3, thi-1, uvrA6, ara-14, lacY1, galK2, xyl-5, mtl-1, gyrA98 (nalA98), rpsL31, tsx-33, lambda, supE44) was transformed with pRH212 and grown to an $OD_{600}$ at 37° C. 20 ml of culture were irradiated in an open Petri dish with a UV germicidal lamp (15W) from a distance of 50 cm for 5 seconds and then incubated for another hour. 100 mcg of D-cycloserine were added to the culture. After 16 hours the bacteria were removed by centrifuging, washed twice with Hershey saline solution (5.4 g/l NaCl, 3.0 g/l KCl, 1.1 g/l $NH_4Cl$, 15 mg/l $CaCl_2x2H_2O$, 87 mg/l $KH_2PO_4$, 12.1 g/l Tris pH=7.4), resuspended in 5 ml of Hershey medium (per 100 ml of Hershey salts: 2.0 ml of 20% glucose, 0.5 ml of 2% threonine, 1.0 ml of 1% leucine, 1.0 ml of 2% proline, 1.0 ml of 2% arginine, 0.1 ml of 0.1% thiamine-HCl) and incubated for 2 hours with 20 mcg/ml of indoleacrylic acid. After the addition of 5 mcCi/ml of $^{35}$S-methionine and further incubation at 37° C. (1 hour) the plasmid-encoded proteins were radioactively labelled. The bacteria were centrifuged off and taken up in 200 mcl of SDS probe buffer (Lämmli Gel System, e.g., L.G. Davies et al., *Methods in Molecular Biology*, pp. 306-310 (1986)). The labelled products were separated on a 15% acrylamide gel.

The gel was dried and exposed on Kodak X-Omat S film. As a reference, purified VAC-alpha protein was run with it and made visible by staining. VAC-alpha runs rather faster than the pRH212 encoded VAC-beta, as might be expected from the molecular weight. The expression of VAC-beta can also be stimulated by the addition of the inducer indoleacrylic acid (FIG. 24).

c) Expression clone pRH292

The expression vector pRH284T was linearized with SacI and the 3' overhanging ends were converted into straight ends with DNA polymerase I/Klenow fragment and dGTP. The vector was recut with SalI and the large fragment was isolated. The HindIII-SalI insert of the clone pRH212 was isolated. 0.2 pMol of the oligonucleotide pair

```
5'  GCTTGGTGGAA  3'  EBI-684
3'  CGAACCACCTTTCGA  5'  EBI-685
```

was ligated with 0.2 pMol of VAC-beta insert and 0.015 pMol of prepared pRH284T. *E. coli* HB101 was transformed with the ligase solution. The resulting clone was designated pRH292 (FIG. 24).

EXAMPLE 7

Detecting the expression of VAC-alpha and VAC-beta in *E. coli* a) Cultivation of the clones HB101/pRH291 and HB101/pRH292

Media:

1) Preliminary culture 10 g/l tryptone
5 g/l yeast extract
4 g/l glucose
9 g/l $Na_2HPO_4.2H_2O$
1 g/l $NH_4Cl$
1 ml/l lM $MgSO_4.7H_2O$
100 mg/l ampicillin
Initiation pH=7.2

2) Main culture 0.68 g/l $(NH_4)_2HPO_4$
0.62 g/l $K_2HPO_4.3H_2O$
2.33 g/l KCl
0.5 g/l NaCl
0.53 g/l $NH_4Cl$
1.23 g/l $MgSO_4.7H_2O$
0.011 g/l $CaCl_2$
10 mg/l thiamine.HCl
3.92 mg/l $(NH_4)_2Fe(SO_4)_2.6H_2O$
0.72 mg/l $AlCl_3.6H_2O$
0.72 mg/l $CoCl_2.6H_2O$
1.5 mg/l $KCr(SO_4)_2.12H_2O$
0.75 mg/l $CuSO_4.5H_2O$
0.19 mg/l $H_3BO_3$
0.51 mg/l $MnSO_4.H_2O$
0.79 mg/l $NiSO_4.6H_2O$
0.73 mg/l $Na_2MoO_4.2H_2O$
0.86 mg/l $ZnSO_4.7H_2O$
21 g/l casein hydrolysate (Merck Art. No. 2238)
25 g/l casein hydrolysate (Sigma C9386)
100 mg/l cysteine
2 g/l yeast extract
1 g/l citric acid
11 g/l glucose.$H_2O$ (start or feed)

700 ml of preliminary culture medium were inoculated with the expression clone and inclubated for 12 to 15 hours at 37° C. with stirring (1000 rpm (revolutions per minute), magnetic rod) and with the introduction of oxygen (5 vvm (=vol/vol/min), ventilation grid). 600 ml of this preliminary culture were transferred into a fermenter containing 12 litres of main culture medium. The main culture was fermented under the following conditions:

| | |
|---|---|
| Stirrer system: | blade stirrer at 1000 rpm |
| Ventilation: | 1.0 vvm |
| Temperature: | 28° C. |
| pH: | 6.5 (25% $NH_3$ for correction) |

During fermentation the glucose concentration was measured. When it fell to 5 g/l, 10 g/l of glucose were added. All other additions, of 10 g/l in each case, were carried out when the glucose concentration in the fermenter fell to 10 g/l. If the partial oxygen pressure fell to about 0.05 atm, the pressure in the fermenter was increased to 0.3 bar. After 20 hours the mixture was cooled to 15° C., the biomass was separated from the nutrient medium by means of a CEPA centrifuge and frozen at −70° C.

b) Detection of the recombinant VAC-alpha or VAC-beta protein

Solutions:

Probe buffer:
125 mN Tris pH = 6.8
4% SDS
10% mercaptoethanol
10% glycerol
0.02% bromophenol blue Acrylamide gel:

| Stacking gel: | Separating gel |
|---|---|
| 3% acrylamide | 13.5% acrylamide |
| 0.1% bisacrylamide | 0.45% bisacrylamide |
| 125 mM Tris pH = 6.8 | 375 mM Tris pH = 8.8 |
| 0.1% SDS | 0.1% SDS |

Eluant buffer:
14.4 g/l of glycine
3.025 g/l Tris
5 ml 20% SDS

| Protein gel staining solution: | Destaining solution: |
|---|---|
| 0.1% Coomassie Blue | 5% methanol |
| 50% methanal | 10% acetic acid |
| 10% acetic acid | |

Glycerol solution:

-continued

| | |
|---|---|
| 7% acetic acid | |
| 2% glycerol | |
| Transfer buffer: | |
| 10 × transfer buffer: | 1 × transfer buffer: |
| 24.4 g/l Tris | 100 ml/l 10 × transfer buffer |
| 112.6 g/l glycerol | 200 ml/l methanol |
| | 1 ml/l Empigen |
| Blocking solution | PBS: |
| 1% Tween 20 | 8 g/l NaCl |
| 1% BSA (bovine serum albumin) | 0.2 g/l KCl |
| 10% fetal calves' serum | 1.15 g/l $Na_2PO_4$ |
| (GIBCO) in PBS | 0.2 g/l $KH_2PO_4$ |
| | 0.1 g/l $MgCl_2$ |
| | 0.7 g/l $CaCl_2$ |
| Alkaline phosphatase buffer: | |
| 100 mM Tris pH = 9.5 | |
| 100 mM NaCl | |
| 5 mM $MgCl_2$ | |

At the end of fermentation, the optical density of the liquor was determined and one aliquot was taken. The bacteria were pelleted in an Eppendorf centrifuge, resuspended in probe buffer with a concentration of 20 $OD_{600nm}$ (optical density at 600 nm) and denatured for 5 min at 100° C. Any insoluble parts were pelleted by centrifuging in the Eppendorf centrifuge. 5 mcl aliquots were charged onto the acrylamide gel. The reference used consisted of expression clone which had been constantly grown at a higher phosphate concentration (0.08 mM phosphate). Under these conditions, the alkaline phosphatase promoter was not activated.

The proteins were separated at 6.5 V/cm (stacking gel) or at 13 V/cm (separating gel) according to the molecular weight until the bromophenol blue dye had reached the end of the gel. Half the gel was stained with Coomassie Blue. For this purpose, the gel was agitated in the staining solution for 30 minutes and then treated for one hour in the destaining solution. In order to remove excess stain more satisfactorily, a dialysis tube filled with activated charcoal was dipped into the destaining solution. The gel was then treated for 30 min in the glycerol solution and dried by means of a gel drier.

The proteins of the second gel half were transferred to the nitrocellulose filter. To do this, Sandwich Whatman 3MM paper gel nitrocellulose (Schleicher-Schuell, BA85) Whatman 3MM paper in a Biorad transfer apparatus was exposed to a voltage of 150 V (current intensity 1000 mM) in 1× transfer buffer for 2 hours with cooling. The nitrocellulose filter was treated overnight at ambient temperature in 50 ml of blocking solution. The filter was incubated for 3 in 5 ml of blocking solution/1:1000 dilute rabbit anti-VAC antiserum and then washed for 30 min in running water, and 3× for 15 min in PBS/1% Tween 20 (Merck-Schuchardt No. 822184). The filter was incubated for 3 hours at ambient temperature in 20 ml of blocking solution with a 1:2000 dilution of the anti-rabbit IgG (Fc) alkaline phosphatase conjugate (Promega-ProtoBlot Immunoscreening System). It was washed in running water and PBS/1% Tween 20 as described above. The bound antibody-alkaline phosphatase conjugate was detected by a color reaction (Promega-ProtoBlot Immunoscreening System). 66 mcl of NBT (50 mg/ml nitro-blue tetrazolium in 70% dimethylformamide) and 33 mcl of BCIP (50 mg/ml of 5-bromo-4-chloro-3-indolylphosphate in dimethylformamide) were dissolved in 10 ml of alkaline phosphatase buffer. The nitrocellulose filter was incubated in this solution until the color developed and then washed for 30 min with running water. The filter was dried and heat-sealed in plastic film.

FIGS. 19a and 19b clearly show the results. "+Phosphate" is the control with no expression "-phosphate" shows the expression of VAC-alpha (clone HB101/pRH291) or VAC-beta (clone HB101/pRH292) protein under the control of the alkaline phosphatase promoter. Both VAC-alpha and also VAC-beta protein can be readily detected on the stained gel. The quantity of VAC proteins formed is, surprisingly, at least 20 mg/l/$OD_{600nm}$ bacterial culture.

Western blot clearly shows the stained VAC-alpha band. In addition, some proteins of lower molecular weight can be detected in the range up to 30 kD, possibly formed by proteolytic cleavage at the N and/or C-terminus of the VAC-alpha protein. A protein recognized by the anti-serum in the range below 20 kD, which might be a half-molecule of VAC-alpha protein formed by proteolysis, is also noticeable. Surprisingly, VAC-beta was also recognized by the anti-VAC antiserum. Since this band is substantially less strongly stained than the VAC-alpha band but the VAC-beta band in the Coomassie blue-stained gel corresponds to the VAC-alpha in its intensity, it can be concluded that the recognition of the VAC-beta protein by the anti-VAC antiserum is substantially worse than that of the VAC-alpha protein.

EXAMPLE 8

Purification of recombinant VAC-alpha

Starting material:

*E. coli* HB101/pRH291.

The cells were centrifuged and frozen at −70° C.

a) Cell homogenization and extraction 103.5 g. of frozen cell cake was suspended in 500 ml of ice cold lysis buffer (100 mM Tris/HCl, 50 mM EDTA and 200 mM NaCl, pH 7.5) and treated with an Ultra-Turrax (5 brief pulses) in order to destroy any clumps. The suspension was then passed 3 times through a Manton-Gaulin press at 6,000 psi. Finally, the press was rinsed with 300 ml of lysis buffer. A 5% solution of PEI (polyethyleneimine, molecular weight 30,000–40,000) which had been adjusted to pH 8 using 5 N HCl, was slowly added to the homogenized suspension until a final concentration of 0.5% PEI was established. After stirring for 30 minutes in an ice bath, the solution was clarified at 9,000 g, 60 min and at 4° C. using a Beckmann J2-21 centrifuge (crude extract).

b) Ammonium sulphate fractionation:

Solid ammonium sulphate was slowly added to the stirred crude extract up to a saturation of 30% (176 g/l). The precipitate was removed after one night in the refrigerator. The clear supernatant was slowly mixed with solid ammonium sulphate until a saturation of 65% was achieved (235 g/l supernatant) and then stirred for 2 hours. The precipitate was then collected by centrifuging at 10,000 g 30 min at 4° C. It was dissolved in 500 ml of 20 mM Tris/HCl 50 mM NaCl, pH 7.4, and dialyzed with the same buffer until all the ammonium sulphate had been removed (determined by the absence of $BaSO_4$ formation after the addition of $BaCl_2$ to the dialysate).

c) Chromatography on DEAE-SEPHAROSE FAST FLOW

The dialysate was clarified by centrifuging and applied to a 160 ml DEAE-FF-Sepharose column (Pharmacia) which had been equilibrated with 20 mM Tris/HCl+50 mM NaCl, pH 7.4. As soon as the $OD_{280nm}$ of the eluate reached the buffer level, a gradient of 50-500 mM NaCl in 20 mM Tris/HCl, pH 7.4, was applied (in all, 10 column-volumes of the linear gradient). The eluate was monitored at $OD_{280nm}$ and analyzed by SDS-PAGE and Western blot using a rabbit antiserum against placenta VAC, prepared in the manner described for the bovine VAC in EPA 0181465, and a swine anti-rabbit IgG coupled to alkaline phosphatase. Any fractions containing VAC were collected, and some fractions were discarded at the end of the main peak. The VAC pool was concentrated using an AMICON ultra-filtration cell and PM 10-type Ultrafilter.

d) Chromatography on Sephacryl 5-200 "High Resolution"

A Pharmacia K 26/100 column (500 ml) was charged with Sephacryl S-200 HR (Pharmacia) and equilibrated with 20 mM bis-Tris/HCl+100 mM NaCl, pH 6.3, at a throughflow rate of 15-20 ml/hour. 6-15 ml aliquots of the concentrated DEAE-FF-Sepharose pool (total 87.4 ml) and subsequently the bis-Tris buffer (see above) were applied to the column. The eluate was monitored at $OD_{280nm}$. The peak representing VAC was the last noticeable peak of the UV profile, as could be shown by SDS-PAGE and Western blots of aliquots. It was collected, the pools from all the tests were combined (7 in all) and dialyzed against 20 mM bis-Tris/HCl pH6.3.

e) Chromatography on a Q-SEPHAROSE-FAST-FLOW

A 40 ml column (K 16/20) of a Q-Sepharose-fast-flow (Pharmacia) was connected up to the FPLC sytem (Pharmacia) and equilibrated with 20 mM bis-Tris/HCl, pH 6.3. The dialyzed VAC pool was applied to the column and washed with 20 mM bis-Tris until the $OD_{280nm}$ of the eluate had returned to the buffer level. An NaCl gradient in 20 mM bis-Tris/Hcl, pH 6.3, was used for elution:

| | |
|---|---|
| 0-105 | mM NaCl in 1 column volume (40 ml) |
| 105-245 | mM NaCl in 20 column volumes (800 ml) |
| 245-350 | mM NaCl in 2 column volumes (80 ml) |

VAC could be identified in the last prominent peak of the UV profile, eluting at approximately 0.14 M NaCl. The purity was determined by SDS-PAGE, Western blot, reverse HPLC and isoelectric focussing. The VAC pool was kept at −20° C.

EXAMPLE 9

Comparison of Recombinant and Natural VACα

Methods used:

a) Gel permeation HPLC
b) Reverse Phase HPLC
c) N-terminal sequencing
d) Tryptic peptide map
e) SDS gel electrophoresis
f) Western blot
g) isoelectric focussing For the comparison, natrual VAC was used on one hand and recombinant VAC-alpha on the other hand.

The test conditions for the individual methods of analysis are described hereinafter.

a) Gel permeation HPLC

| | |
|---|---|
| Column: | Waters Protein Pak I 125, 2 × (7.8 × 300 |

-continued

| | |
|---|---|
| | mm), 10 micron particle diameter |
| Eluant: | 0.5 M $Na_2SO_4$, 0.02 M $NaH_2PO_4$, pH 7.0, 0.04% Tween 20, 25% propylene glycol |
| Flux: | 0.5 ml/min |
| Detection: | UV absorption, 214 nm |

The chromatograms of natural and recombinant VAC-alpha show the main peak of the VAC monomer at a molecular weight of 34,000 and 33,000, respectively. In addition, there is a small amount of earlier eluting dimers of the VAC. The molecular weight scale was calibrated by means of 4 standard proteins. The column separates, strictly speaking, according to molecular size and not molecular weight.

b) Reverse Phase HPLC

| | |
|---|---|
| Column: | Bakerbond WP $C_{18}$ 4.6 × 250, 5 micron particle diameter, 30 nm pore diameter |
| Eluant A: | 0.1% trifluoroacetic acid in water |
| Eluant B: | 0.1% trifluoroacetic acid in acetonitrile |
| Gradient: | 20% B for 2 min, 20-68% B in 24 min, 68% B for 10 min, 68-20% B in 1 min |
| Flux: | 1.0 ml/min |
| Detection: | UV absorption, 214 nm and 280 nm |

The chromatograms of natural and recombinant VAC show a retention time of about 29 min for VAC. The very small peaks also present are only partly impurities in the VAC probe. All the peaks designated BW originate from the blind value of the column.

c) N-terminal sequencing

A peak of recombinant VAC-alpha which had been desalinated by reverse phase HPLC was sequenced. Sequencing was effected with a gas phase sequenator made by the firm Applied Biosystems (Model 470A) using the program 40 APTH. The probe was dissolved in 50 mcl of 70% HCOOH. 2×25 mcl were applied to the sequenator. Wtih an initial quantity of 2.3 nMol, it was possible to sequence up to amino acid 39. 100% agreement was found with the expected sequence (from natural protein and cDNA). No additional N-terminal Met could be detected (≦1%). In recombinant VAC-alpha the N-terminus is free and not blocked, as in natural VAC.

d) Tryptic peptide map

Natural VAC and recombinant VAC-alpha were compared. From both samples, VAC was desalinated by reverse phase HPLC, dried and dissolved in 0.1% $HN_4HC0_3$. For the cleavage, 4% by weight of trypsin (Worthington, TPCK treated, dissolved in a quantity of 1 mg/ml in water) were added and, after 6 hours incubation at 37° C., a further 4% by weight of trypsin were added. After further incubation overnight the peptides formed were separated by reverse phase HPLC. The enclosed chromatograms (214 nm and 280 nm) show a virtually identical peptide pattern.

| | |
|---|---|
| Column: | Waters μBakerbond WP $C_{18}$, 3.8 × 300 mm, 10 micron particle diameter, 10 nm pore diameter |
| Eluant A: | 0.1% trifluoroacetic acid in water |
| Eluant B: | 0.1% trifluoroacetic acid in acetonitrile |
| Gradient: | 0-55% B in 55 min, 55% B for 15 min, 55-0% B in 1 min |
| Flux: | 1.0 ml/min |
| Detection: | UV absorption, 214 nm and 280 nm |

e) SDS gel electrophoresis

SDS gel electrophoresis was carried out largely according to the method originally described by U.K. Laemmli (*Nature* 227:680–685 (1979)). Silver staining was carried out using the method of Oakley (*Anal. Biochem.* 105:361–363 (1980)). The first gel shows a comparison between natural and recombinant VAC-alpha. The content of dimeric VAC was quantified by scanning with a laser densitometer and was 2% in natural VAC and 4% in recombinant VAC. The second gel shows only recombinant VAC-alpha applied both with the without DTT (dithiothreitol, reducing agent). This shows that the SDS-stable dimer is obviously bound via disulphide bridges which can be reduced with DTT.

Original solutions of the reagents

15% Ammonium persulfate solution APS 150 mg of ammonium persulfate are dissolved in 1 ml of distilled water.

30% acrylamide+0.8% bis acrylamide

| Acrylamide | bis acrylamide | Water ad. |
|---|---|---|
| 15 g | 0.4 g | 50 ml |
| 30 g | 0.8 g | 100 ml |
| 45 g | 1.2 g | 150 ml |

The acrylamide is dissolved in the corresponding volume of water and filtered before use.

Separating gel buffer 1.5 M Tris HCl, 0.4% SDS (sodium dodecylsulfate), pH 8.8

18.16 g Tris+0.4 g SDS is adjusted to pH 8.8 with conc. HCl and topped up to 100 ml with distilled water.

Stacking gel buffer 0.5 M Tris-HCl, 0.4% SDS, pH 6.8

6.04 g Tris+0.4 g SDS is adjusted to pH 6.8 with conc. HCl and made up to 100 ml with distilled Eluting buffer 25 mM Tris, 192 mM glycine, 0.1% SDS, 0.005% Na-azide, pH 8.5

12 g Tris+57.6 glycine+4 g SDS+0.2 g sodium azide are dissolved in about 3.5 l of distilled water, adjusted to pH 8.5 and made up to 4.0 litres. It is advisable to compare the conductivity of the new eluting buffer with the preceding batches.

0.05% Coomassie Blue staining solution 0.55 g of Coomassie Brillant Blue R 850 are dissolved in 500 ml of methanol, stirred for 30 min and filtered. 100 ml of glacial acetic acid and 500 ml of distilled water are added thereto.

Destaining solution a) Manual destaining

The destaining solution corresponds to the staining solution without the dye: 500 ml of methanol+500 ml of distilled water+100 ml of glacial acetic acid b) Electrophoretic destaining in 7.5% acetic acid.

4×SDS application buffer (can be kept for about 1 month)

| | | |
|---|---|---|
| Dye concentrate: | Bromophenol blue | 50 mg |
| | Glycerol | 0.5 ml |
| | Distilled water ad. | 10 ml |
| The solution can be kept for about 3 months. | | |
| Application buffer: | dye concentrate | 0.4 ml |
| | SDS | 0.8 g |
| | Glycerol | 4 g |
| | Distilled water ad. | 10 ml |

-continued

| | | | |
|---|---|---|---|
| 1 × SDS application buffer | | | |
| Dilution 1:4 of the 4 × SDS application buffer with distilled water. | | | |
| Silver staining according to Oakley | | | |
| Reagents | | | |
| Destainer: | Ethanol | | 200 ml |
| | Conc. acetic acid | | 62.5 ml |
| | Distilled water ad. | | 1000 ml |
| 10% Glutardialdehyde solution: | | | |
| 25% glutardialdehyde solution | | 20 ml or | 40 ml |
| Distilled water ad. | | 50 ml or | 100 ml |
| The solution must be kept in a refrigerator. | | | |
| 0.1 N ammoniacal silver solution: | | | |
| Should only be prepared immediately before use! | | | |
| 0.1 N silver nitrate (16.9 g/l) | | 23 ml | 46 ml |
| 25% ammonia solution | | 0.9 ml | 1.9 ml |
| 0.36% sodium hydroxide (1.8 g/0.5 l) | | 10.5 ml | 21 ml |
| distilled water ad. | | 50 ml | 100 ml |
| Developer solution: | | | |
| Prepare immediately before use! | | | |
| 0.5% citric acid (1.25 g/250 ml) | | | 5 ml |
| distilled water | | | 1 l |
| 37% formaldehyde | | | 1 ml |

Destainer solution (Photofixer):

Kodak fixer (Photolaboratory) diluted 1:4 with distilled water. The dilution can be used several times but the time taken for destaining increases after frequent use.

2% glycerol solution:

23 g glycerol 87% in 1 l of distilled water.

Method of silver staining according to Oakley

After electrophoresis the gel was labelled at one corner and then underwent the following staining steps in the shaker:

30 min in the destainer bath 30 min in 20% glutardialdehyde solution (50 ml)

30 min in running water or overnight in about 2 l of water 10 min in ammoniacal silver solution (50 ml)

3 min in running water about 5 min in developer solution.

The developing process was not ended after an exact period of time but when the bands were sufficiently stained or, at the latest, when the background began to stain. Development was stopped by watering the gels for 30 min (in a tank or under running water).

Development still continued when the gel was in water! (diffusion time). Destaining of the gel was only necessary if the background as too strongly stained!

about 5–10 min in a Kodak fixer until optimum contrast between the bands and the background had been achieved. Note! Destaining also continued even after being stopped directly in running water (diffusion time)

30 min in 2% glycerol solution.

After this the gel could be dried on filter paper at 80° C. for one hour.

f) Western blot

Immunological proof was obtained for VAC with rabbit anti-VAC serum (diluted 1:1000) and with swine antirabbit IgG (1:500 dilution), which is conjugated with alkaline phosphatase. In order to detect the enzyme activity of alkaline phosphatase, the substrates BCIP (5-bromo-4-chloro-3-indolyl-phosphate) and NBT (nitro blue tetrazolium) were used. Comparative protein staining on the nitrocellulose was carried out with amido black.

Western blotting by the semi-dry method

1. Materials:

Semi-dry electroblotter (Messrs. Sartorius) SM 175 56; filter paper the same size as the gel which is to be blotted; nitrocellulose membrane (pore size 0.45 mcm) the same size as the gel;

| 2. Reagents | | |
|---|---|---|
| Anode buffer 1: pH 10.4 | | |
| 0.3 M Tris | 3.63 g/80 ml | |
| 20% methanol | 20 ml | |
| Anode buffer 2: pH 10.4 | | |
| 25 mM Tris | 0.3 g/80 ml | |
| 20% methanol | 20 ml | |
| Cathode buffer: pH 9.4 | | |
| 25 mM Tris | 0.3 g/80 ml | |
| 40 mM ε-aminocaproic acid | 0.52 g/80 ml (MW 131.3) | |
| 20% methanol | | |
| Amido black protein staining medium | | |
| 0.5% (w/v) amido black | 0.5 g in 40 ml | |
| 50% methanol | 50 ml | |
| 10% acetic acid | 10 ml | |
| Destainer | | |
| Methanol | water | acetic acid |
| 5 | 5 | 5 |
| PBS (Phosphate buffered saline) 10 × concentrate pH 7.2 | | |
| 136 mM sodium chloride | 80 g | |
| 26 mM calcium chloride | 2 g | |
| 80 mM disodium hydrogen phosphate | 11.3 g | |
| (80 mM disodium hydrogen phosphate .12$H_2O$ | 28.7 g) | |
| 14 mM potassium dihydrogen phosphate | 2 g | |
| made up with distilled water to | 1 l | |
| dilute 1/10 before use!!! | | |
| Blocking buffer: | | |
| 1% BSA | | |
| 0.1% Tween 20 | | |
| in 1 × PBS | | |
| Washing buffer: | | |
| 1 × PBS | | |
| 1 × PBS + 0.1% Tween 20 | | |
| 1 × PBS | | |
| Staining buffer for alkaline phosphatase staining: pH 9.9 | | |
| 100 mM Tris | 1.22 g | |
| 100 mM sodium chloride | 0.58 g | |
| 5 mM magnesium chloride. 6$H_2O$ | 0.10 g | |
| made up to 100 ml with distilled water | | |
| NBT (Nitro blue tetrazolium) solution | | |
| 50 mg NBT (Messrs. Sigma N-6876)/ml 70% dimethylformamide | | |
| BCIP (5-bromo-4-chloro-3-indolyl-phosphate) solution | | |
| 50 mg BCIP (Messrs. Sigma B-8503)/ml in 100% dimethyl-formamide | | |
| Staining medium for alkaline phosphatase | | |
| Staining buffer | 10 ml | |
| BCIP | 0.033 ml | |
| NBT | 0.065 ml | |

Antibody reagents:

Rabbit anti-VAC serum conjugated with alkaline phosphatase.

3. Effecting the blot

Blotting was carried out at 0.8 m/a$cm^2$ of gel area over a period of 60 min.

4. Detecting the protein on the nitrocellulose membrane 4.1 Protein staining with amido black The part of the nitrocellulose membrane intended for the protein staining was cut away and placed in amido black staining solution for 5 min. Then the staining solution, which could be used several times, was poured away and any excess staining solution was rinshed off the nitrocellulose membrane with water.

4.2 Immunological detection 4.2.1 Blocking of the nitrocellulose membrane

Before the immunological detection, the nitrocellulose membrane was blocked for at least 60 min (or overnight) with 1% BSA in 1×PBS with 0.1% Tween 20.

4.2.2 Detection with enzyme-labelled antibodies

After blocking, the nitrocellulose membrane was incubated for 60 min with rabbit anti-VAC serum (suitably diluted in blocking medium).

It was then washed 3 times: 1×PBS, PBS with 0.1% Tween 20, 1×PBS. The membrane was then incubated with swine anti-rabbit IgG, which was conjugated with alkaline phosphatase (also in a suitable dilution in blocking medium for 60 min). It was then washed again with 3×PBS as described above.

4.2.3 Enzymatic staining of the blot

The nitrocellulose membrane was placed in staining medium (10 ml were sufficient for a minigel) and slowly moved about in a shaker until the bands appeared to be sufficiently stained. Staining was ended by washing out the staining medium with water, then the nitrocellulose membrane was dried in air.

5. Evaluation of the Western blot

The immunologically/enzymatically detected bands of the blot were compared with the bands of protein staining of the blot and also with the corresponding band pattern of SDS electrophoresis and were assigned to one another.

7. Isoelectric focussing

The isoelectric point (pI) for recombinant VAC alpha, at 4.9, is 0.1 pH unit higher than for natural VAC (4.8).

Polyacrylamide gel—Isoelectric focussing (PAGIF or IEF)

Equipment and Reagents

Polyacrylamide gel plats for isoelectric focussing polymerized onto film. (LKB - "PAGplate", SERVA-"Servalyt Precotes").

| | |
|---|---|
| pH 3.5-9.5 (LKB PAGplate) | |
| Anode solution: | 1 M phosphoric acid |
| Cathode solution: | 1 M sodium hydroxide solution |
| pH 5.5-8.5 (LKB-PAGplate) | |
| Anode solution: | 0.4 M HEPES (with Na-azide) |
| Cathode solution: | 0.1 M NaOH |
| pH 4.0-6.5 (LKB-PAGplate) | |
| Anode solution: | 0.5 M phosphoric acid + 0.1 M glutamic acid |
| Cathode solution: | 0.1 M Beta-alanine (with Na-azide) |
| pH 3.5-9.5 (SERVALYT-Precotes) | |
| Anode solution: | 25 mM aspartic acid + 25 mM glutamic acid |
| Cathode solution: | 2 M ethylenediamine + 25 mM arginine base + 37.5 mM lysine base |
| Coolant: | Kerosene (made by SERVA) |
| Fixing solution: | 10% Trichloroacetic acid (TCA) with 5% sulfosalicylic acid |
| 0.05% Coomassie blue staining solution | |
| Destainer: | 500 ml methanol + 500 ml water + 100 ml glacial acetic acid |

Probes:

The probes should be low in salt, or better still, free from salt. Higher salt concentrations must be dialyzed against about 5-10 mM buffer or water before the IEF. NaCl, however, may be present in quantities of up to 100 mM without disrupting the elution fronts.

Fixing the IEF gel before protein staining

The gel was placed in the fixing solution for about 20 min but without shaking! (it is easily detached from the film). It was then watered for 5 min.

Protein staining of the EIF gels with Coomassie Blue

The fixed gels were placed in a staining solution for about 2 hours and moved around only very gently.

Destaining of the IEF gels

After the staining, the excess staining solution was rinsed away with water and the gel was destained by frequently changing the destainer. After it had been adequately destained the gel was watered again until the destainer had all been washed out.

Drying the IEF gels

The gels were placed on a wet, water-permeable transparent film or dialysis membrane with the water-impermeable side upwards and dried for one hour at 80° C.

EXAMPLE 10

Construction of tetracycline-resistant VAC-α and VAC-β expression Vectors (pGN25, pGN26)

1 mcg of pAT153 was cut with EcoRI in 50 mcl of solution. The enzyme activity was destroyed by heating to 70° C. and the overhanging ends were straightened by the addition of DNA polymerase I/Klenow fragment (PollK) (5 units) and the four deoxyribonucleoside triphosphates (20 mcM each final concentration) in a fill-in reaction. After heating to 70° C. to destroy the PollK activity the DNA was precipitated with ethanol. The linearized DNA was recut with PvuI in 50 mcl.

pRH291 and pRH292 were first linearized with SphI and the 3' overhanging end was degraded by the 3' exonucleolytic activity of PollK in the presence of dGTP. After precipitation of the DNAs these were recut with PvuI. The fragments from all three digestions were separated on agarose gel and the corresponding fragments were eluted (pAT153: 3032 bp, pRH291: 1987 bp, pRH292: 2607 bp). 50 ng of pAT153 fragment were mixed with 50 ng of pRH291 or pRH292 fragment and ligated in 10 mcl. 100 mcl of competent *E. coli* HB101 were combined with 5 mcl of ligase solution and transformed. Selection was carried out on LB agar containing 100 mcg/ml of ampicillin. Of the clones formed, some were spread out on LB agar with 12.5 mcg/ml of tetracycline. The clones growing thereon were used to prepare plasmid DNA. The plasmid DNA prepared in a mini preparation was cut with various restriction enzymes and in this way the correctness of the construction was checked. One clone was selected in each case and designated pGN25 (VAC-α) or pGN26 (VAC-β).

*E. coli* HB101/pGN25 or HB101/pGN26 were subjected to fermentation as described in Example 7, but this time instead of the ampicillin 5 mg/l of tetracycline were used in the pre-culture. During the main fermentation, aliquots were taken and investigated on a 15% acrylamide/0.1% SDS gel according to Lämmli. No difference was found from the fermentations of *E. coli* HB101/pRH291 or HB101/pRH292. VAC-α and VAC-β were purified from the biomass of the fermentation. Protein analysis also showed no difference from the corresponding recombinant proteins from the fermentations of clones HB101/pRH291 and HB101/pRH292.

EXAMPLE 11

Purification of recombinant VAC-beta

Starting material:

*E. coli* clone HB101/pRH292

3) Cells were harvested by centrifugation and frozen at −70° C.

Cell homogenization and extraction 100 gms of frozen cells were suspended in 500 ml ice-cold lysis buffer (100 mM Tris/HCl, 50 mM EDTA and 200 mM NaCl, pH 7.5) and treated with 5 short pulses in an Ultra-Turrax to break lumps. The suspension was then passed 3-times through a MantonGaulin press at 6000 psi and the press finally rinsed with 300 ml lysis buffer. To the homogenized suspension was slowly added a 5% solution of PEI (polyethylene imine, mol. weight 30,000–40,000), which was adjusted to pH=8 with 5N hydrochloric acid, to give a final concentration of 0.5% PEI. After stirring in an ice-bath for 30 min., the soltuion was clarified at 900 g for 60 min. at 4° C., using a Beckman J2-21 centrifuge, to obtain the crude VAC-beta extract.

Chromatography on Silica

Silica Catalyst Carrier, Grade 953 W, (Grace GmbH., Worms, BRD) was freed from fines by settling in distilled water and filled into a chromatographic column of 5 cm diameter and 20 cm bed height. After equilibration with lysis buffer, the crude extract was passed over the column and washed with 3 liters of lysis buffer. VAC-beta was eluted with a linear gradient of tetramethylammonium chloride in lysis buffer (0–1 M in 2000 ml buffer). Fractions of the eluate were monitored by SDS-PAGE for VAC-beta, using a reference material. VAC-beta containing fractions were pooled.

Chromatography on DEAF-Sepharose Fast Flow

Pooled Silica-fractions were dialyzed against 20 mM Tris/HCl pH 8.4 and applied to a column (26×330 mm×175 ml) of DEAE-FF-Sepharose (Pharmacia) equilibrated with 20 mM Tris/HCl pH 8.4. The column was washed with 500 ml of buffer and VAC-beta eluted with a gradient of 0–500 mM NaCl in 875 ml buffer (5 column volumes). The eluate was monitored for protein content at 280 nm and protein containing fractions analyzed by SDS-PAGE, using a reference material. VAC-beta containing fractions were pooled and concentrated using an AMICON stirred ultrafiltration cell and a PM 10 ultrafilter.

Chromatography on Sephacryl 5-200 "High Resolution"

A Pharmacia column K 26/100 (500 ml) was packed with Sephacryl S-200 HR (Pharmacia) and equilibrated with 20 mM Tris/HCl+100 mM NaCl pH 8.4 at a flow rate of 120 ml/h. The concentrated VAC-beta pool (4 ml) was applied to the column and the flow rate reduced to 60–80 ml/h. The eluate was monitored at 280 nm for protein. VAC-beta could be identified in the UV-profile as the only peak. It was pooled, thereby removing a shoulder of high molecular weight impurities, which were also detectable in the UV-profile. The purified VAC-beta was analyzed by SDS-PAGE and kept at −20° C.

TABLE

Purification of recombinant VAC-beta starting material: 100 g frozen cell paste.

| | Volume (ml) | mg protein/ml[x)] | mg total |
|---|---|---|---|
| Crude Extract | 810 | 16.1 | 13,040 |

TABLE -continued

| Purification of recombinant VAC-beta starting material: 100 g frozen cell paste. | | | |
|---|---|---|---|
| | Volume (ml) | mg protein/ml[x)] | mg total |
| Silica Flow-Through | 2270 | 0.35 | 795 |
| VAC-beta Silica Pool | 380 | 5.0 | 1,900 |
| VAC-beta DEAE-FF-Pool | 120 | 2.6 | 312 |
| DEAE-FF-Pool | 4 | 58 | 232 |
| VAC-beta Sephacryl-Pool | 33.5 | 2.2 | 74 |

[x)]Protein by BIO-RAD protein assay (standard: bovine serum albumin)

EXAMPLE 12

Analysis and characterization of VAC-$\beta$

SDS gel electrophoresis were used as an in-process check between the individual purification steps. This analysis was carried out exactly as in the final checks and is described therein. A series of the SDS gels obtained during one purification is contained in Example 11 (purification of VAC-$\beta$).

The following methods were used as final checks and to characterize the purified protein:

a) gel permeation HPLC
b) reverse phase HPLC
c) amino acid analysis
d) N terminal sequencing
e) SDS gel electrophoresis
f) isoelectric focussing a) gel permeation HPLC

| | |
|---|---|
| Column: | Waters Protein Pak I 125, 2 × (7.8 × 300 mm) particle diameter 10 mcm, ambient temperature |
| Eluant: | 0.5 M $Na_2SO_4$, 0.02 M $NaH_2PO_4$, pH 7.0, 0.04% Tween 20, 25% propylene glycol |
| Flow rate: | 0.5 ml/min |
| Detection: | UV absorption, 214 nm, 0.5 OUT |

Figure 46:
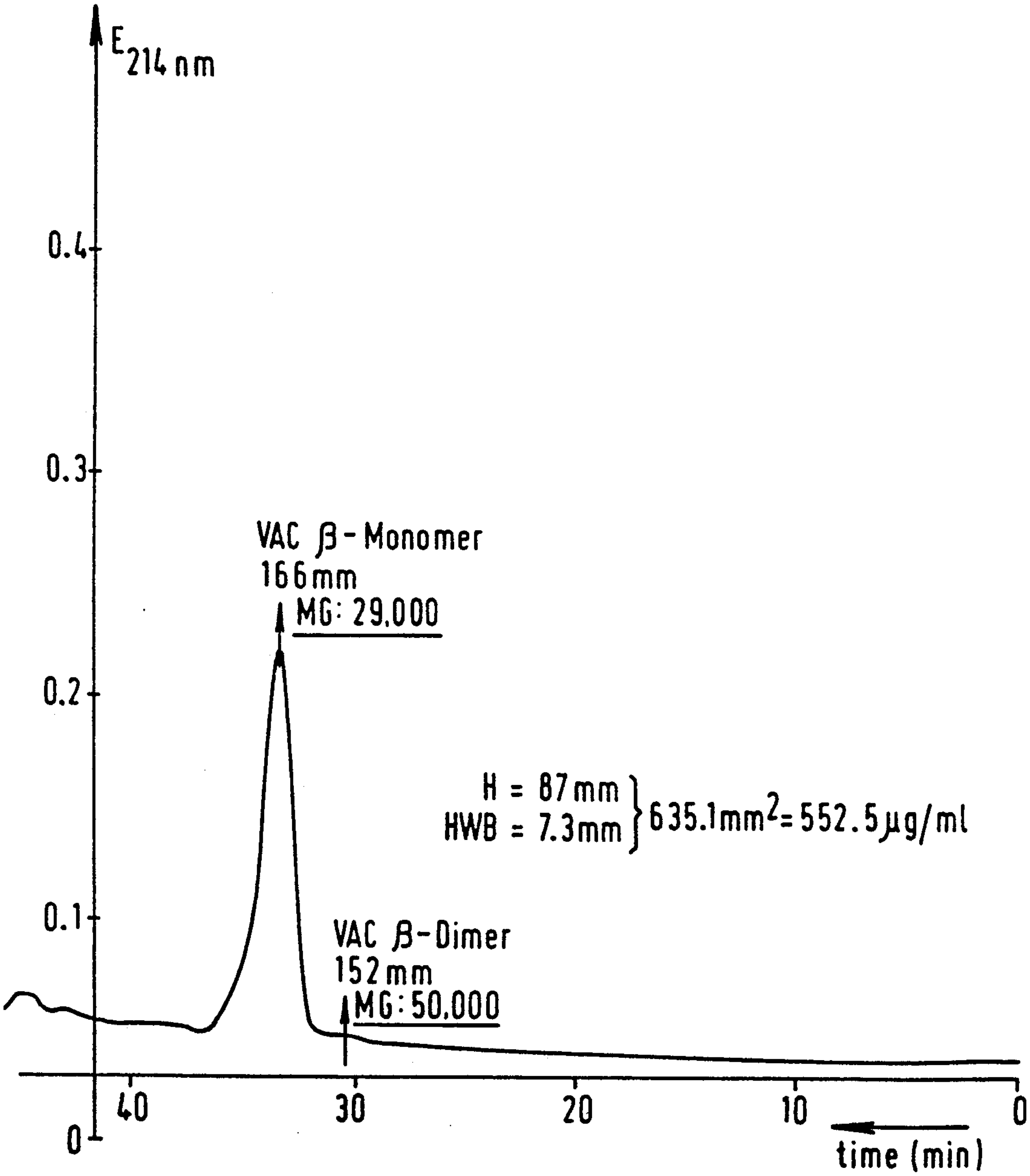
FIG. 46 depicts a gel permeation HPLC of recombinant VAC-β.

The chromatogram (FIG. 46) of purified VAC-$\beta$ shows the main peak of the VAC-$\beta$ monomer at a molecular weight of 29,000, and in addition a small amount of dimeric VAC-$\beta$ can also be detected (M approx. 50,000). These values for the molecular weight are a relatively long way below the expected value (M 37,000), presumably because the gel permeation column used here separates on the basis or molecular size or configuration and not molecular weight.

b) Reverse phase HPLC

| | |
|---|---|
| Column: | Bakerbond WP $C_{18}$, 4.6 × 250 mm, particle diameter 5 mcm, pore diameter 30 nm, ambient temperature |
| Eluant A: | 0.1% trifluoroacetic acid in water |
| Eluant B: | 0.1% trifluoroacetic acid in acetonitrile |
| Gradient: | 20% B for 2 minutes, 20–68% B in 24 min., 68% B for 10 min., 68–20% B in 1 min. |
| Flow rate: | 1 ml/min. |
| Detection: | UV absorption, 214 nm, 0.5 OUT |

Figure 47:
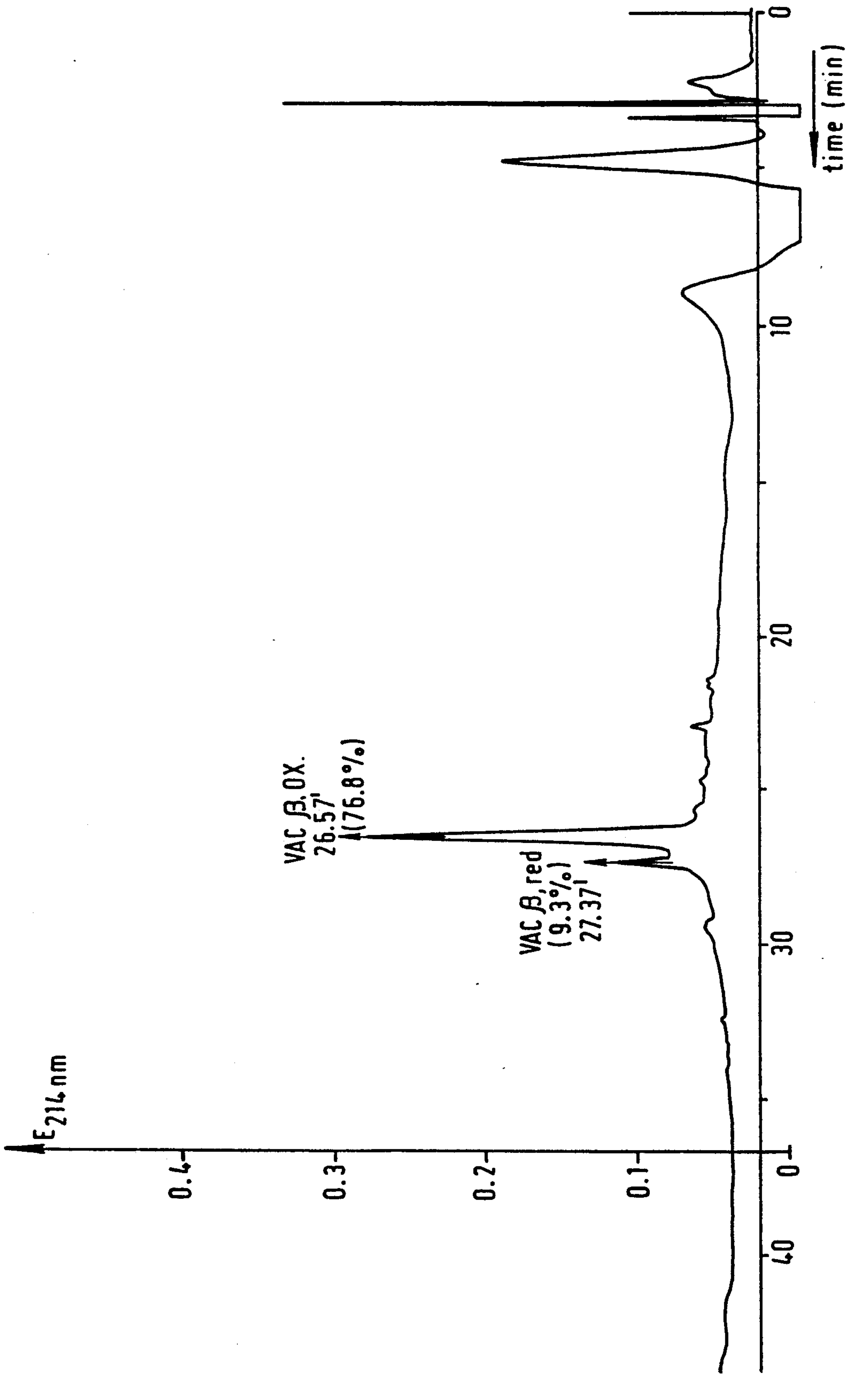
FIG. 47 depicts a reverse phase HPLC of recombinant VAC-β.

The chromatogram (FIG. 47) comes directly from the eluate of the last purification stage and shows the main peak of the oxidized VAC-$\beta$ (two disulphide bridges, $t_R$=26.6 min.). In addition about 9% of reduced VAC-$\beta$ ($t_R$=27.4 min.) and some smaller peaks of residual impurities can be detected.

Figure 48:
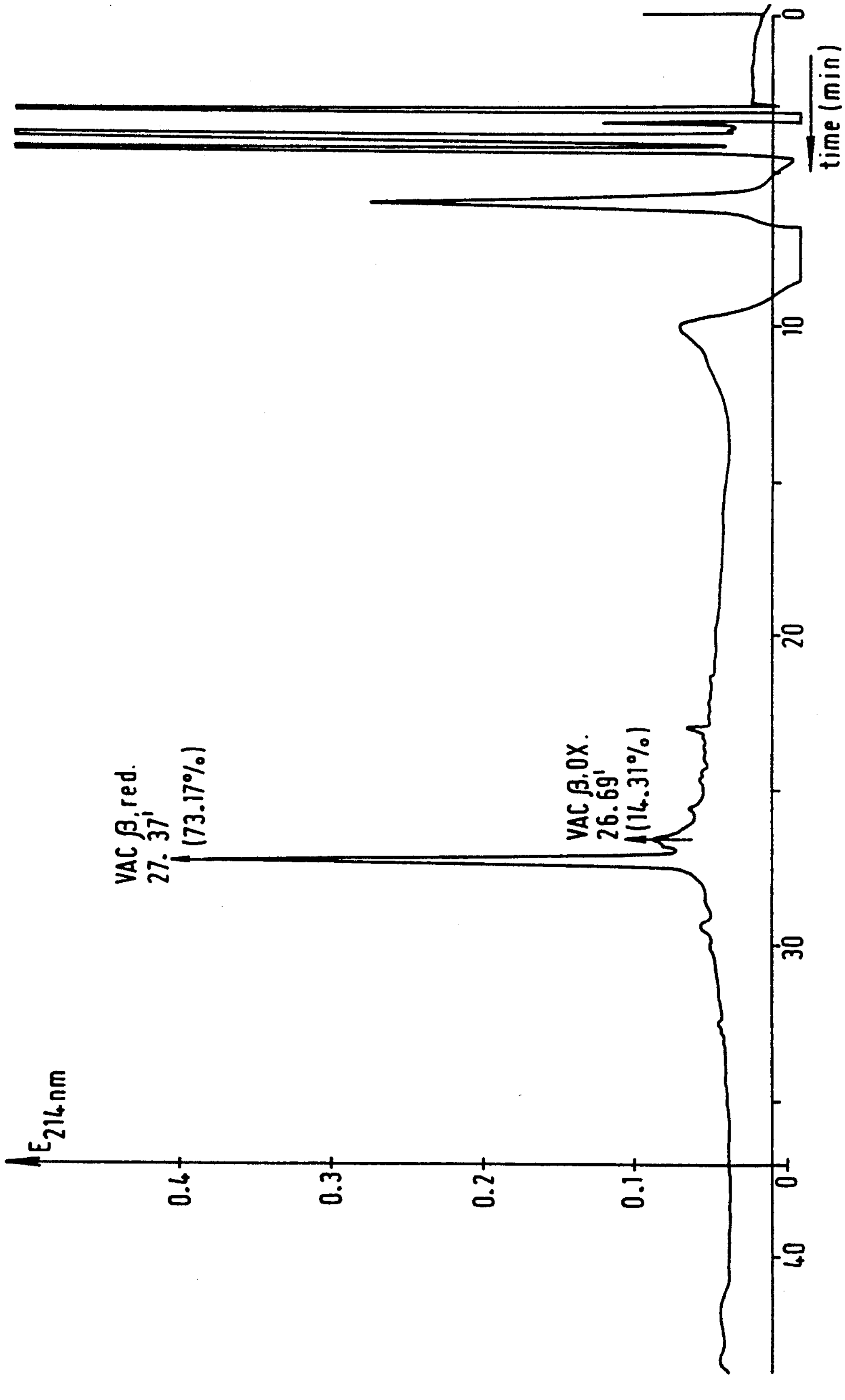
FIG. 48 depicts a reverse phase HPLC of recombinant VAC-β after incubation.

The chromatogram (FIG. 48) shows the same VAC-$\beta$ sample after 2 hours' incubation in 3 M urea, 0.05 M dithiothreitol. The protein occurs mainly in the reduced form ($t_R$=27.4 min.).

c) Amino acid analysis

Purified VAC-$\beta$ was desalinated by reverse phase HPLC (for method see paragraph b). The main peak of VAC-$\beta$ was collected in a hydrolysis tube and dried.

Hydrolysis was carried out with 6 N hydrochloric acid (with 1% phenol) in the gaseous phase (110° C., 22 hours).

The amino acids were measured with an amino acid analyzer (type 6300, made by Beckman) by a post-column derivatization with ninhydrin.

Figure 49B:
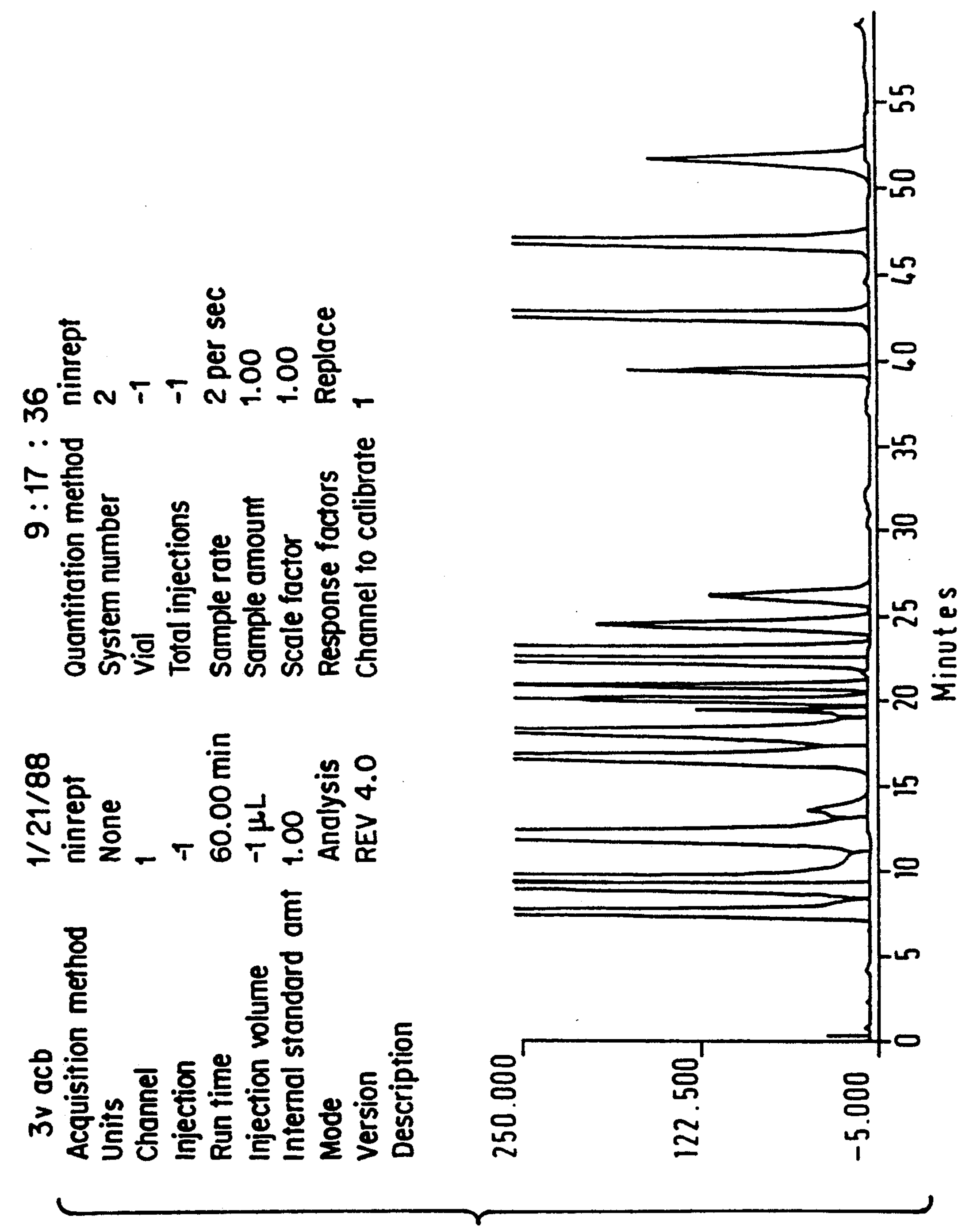
Figure 51:
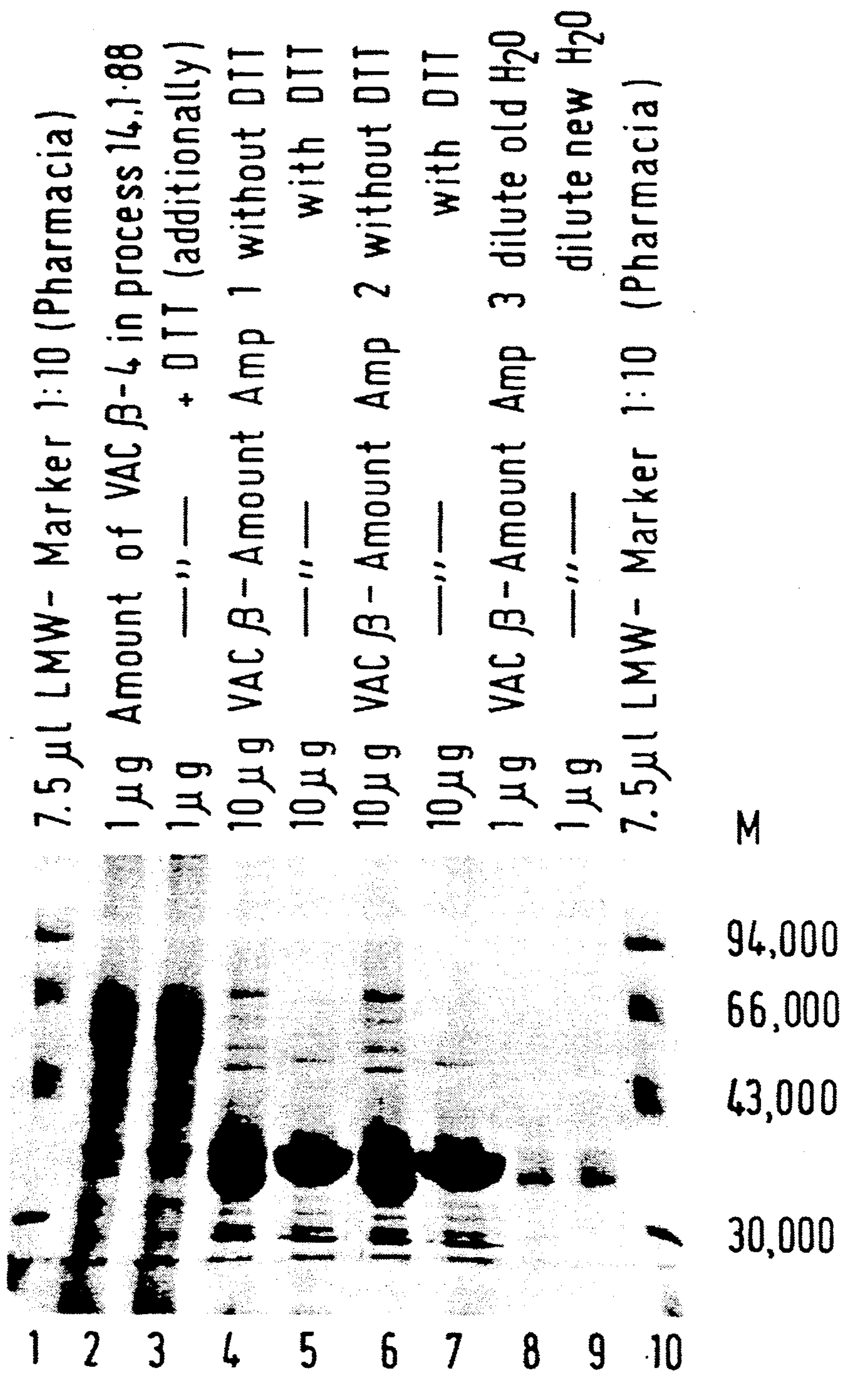
FIG. 51 depicts a 12.5% SDS-PAGE gel of recombinant VAC-β in the presence or absence of DTT, visualized by Coomassie staining.
Figure 52A:
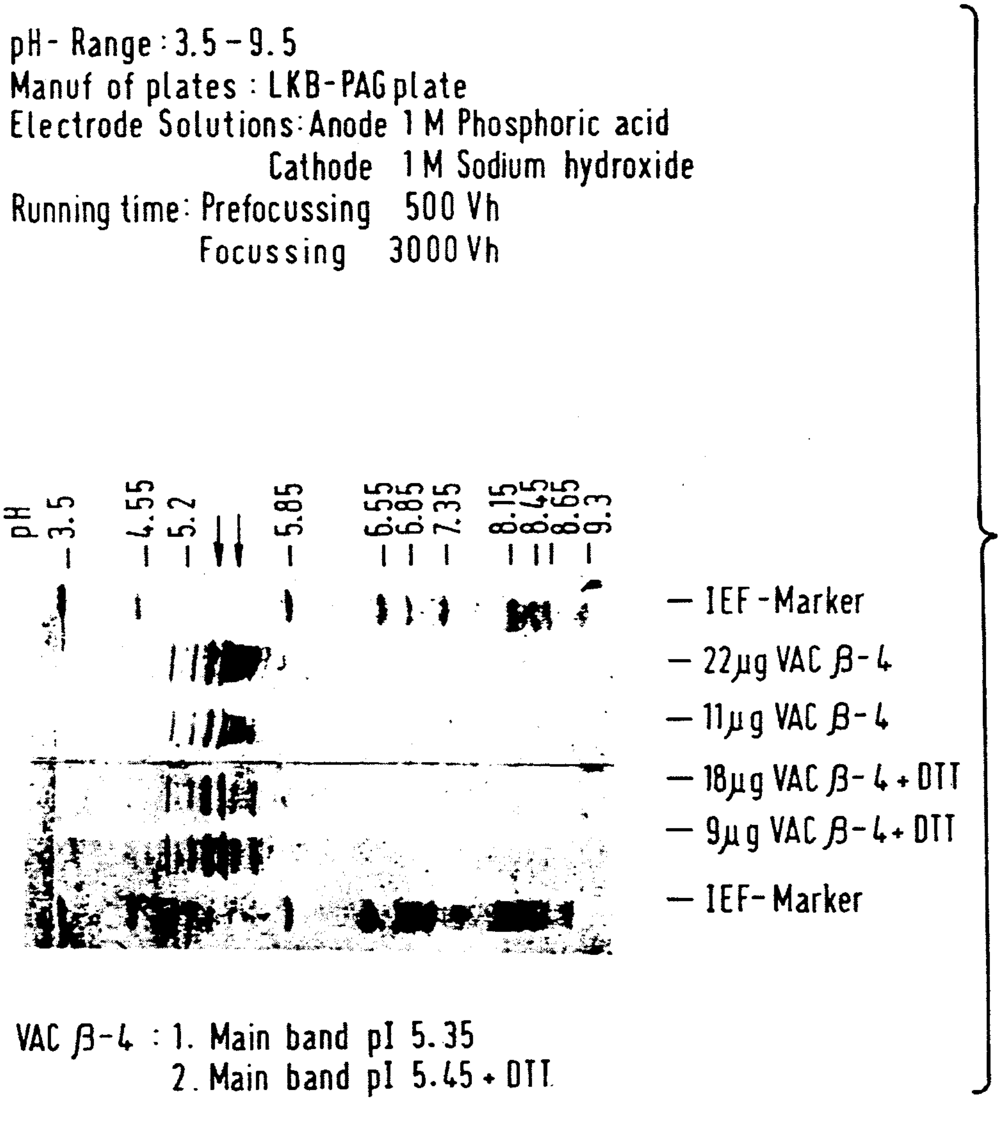
FIG. 52a depicts the isoelectric focussing gel of recombinant VAC-β.
Figure 52B:
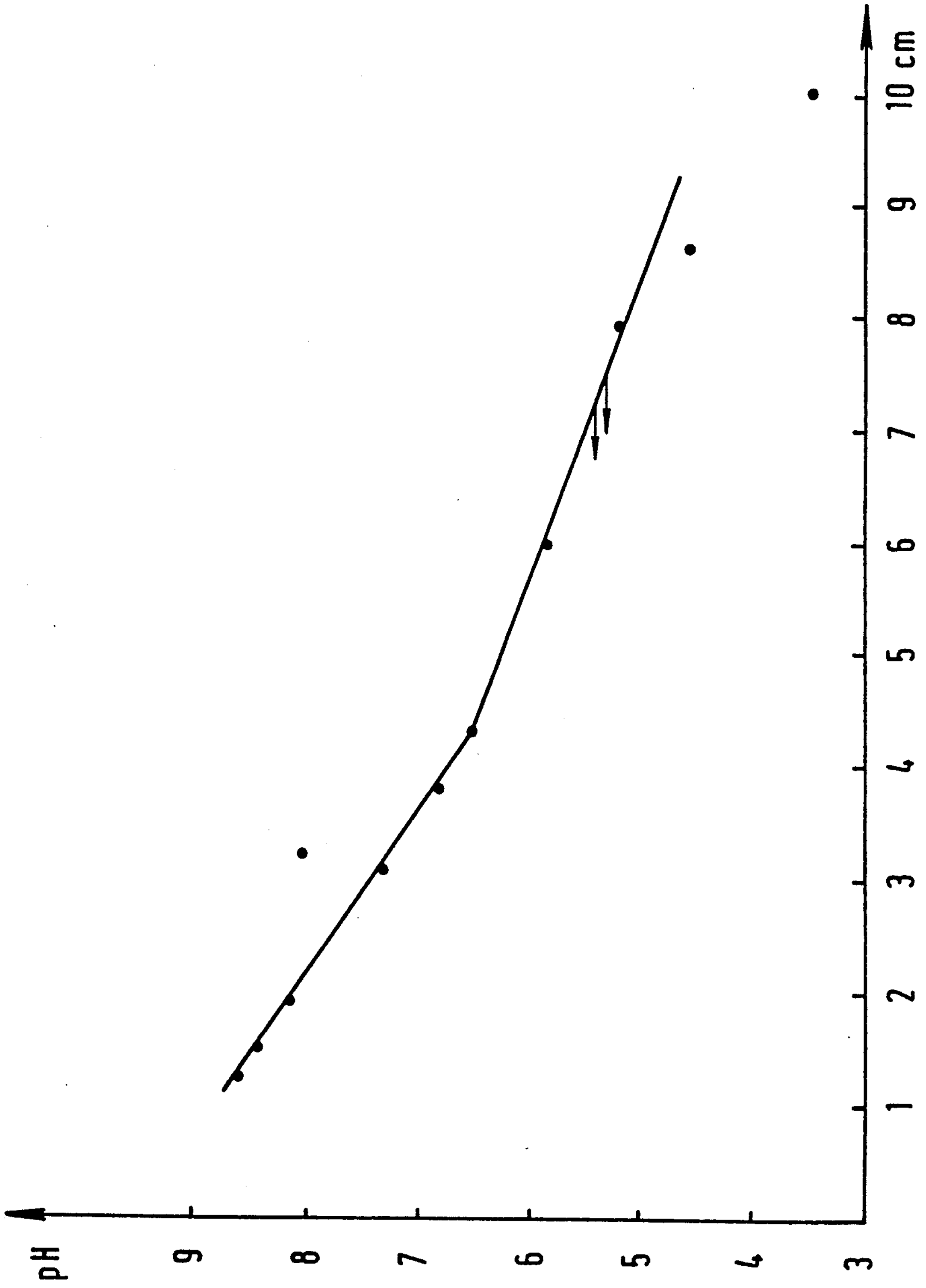
FIG. 52*b* depicts a graphical representation of isoelectric focussing, pH 3.5–9.5, with VAC-β (±DDT reduction).

The amino acid analysis (FIGS. 49*a* and 49*b*) of a VAC-$\beta$ sample shows a total deviation from the theoretical composition of 6.56%.

d) N terminal sequencing

Purified VAC-$\beta$ was desalinated by reverse phase HPLC (for method see paragraph b). The main peak of VAC-$\beta$ was collected and dried.

The residue was dissolved in 75 mcl of 0.1% trifluoroacetic acid and used directly for sequencing.

Sequencing was carried out with a gas phase sequenator made by Applied Biosystems (Model 470 A 9) with the program 39 apth.

It was possible to sequence up to the 39th amino acid with an initial quantity of about 1 nM. 100% agreement with the expected sequence was found. Obviously, N-terminal methionine was split off 100% (FIG. 50).

e) SDS gel electrophoresis

The SDS gel electrophoresis was carried out largely in accordance with the original method prescribed by U.K. Lämmli. For in-process checks, VAC-$\beta$ samples were combined with dithiothreitol before application and decocted. The final checks were carried out both under reducing conditions and also under nonreducing conditions.

The gels were stained with Coomassie Blue.

Figure 45:
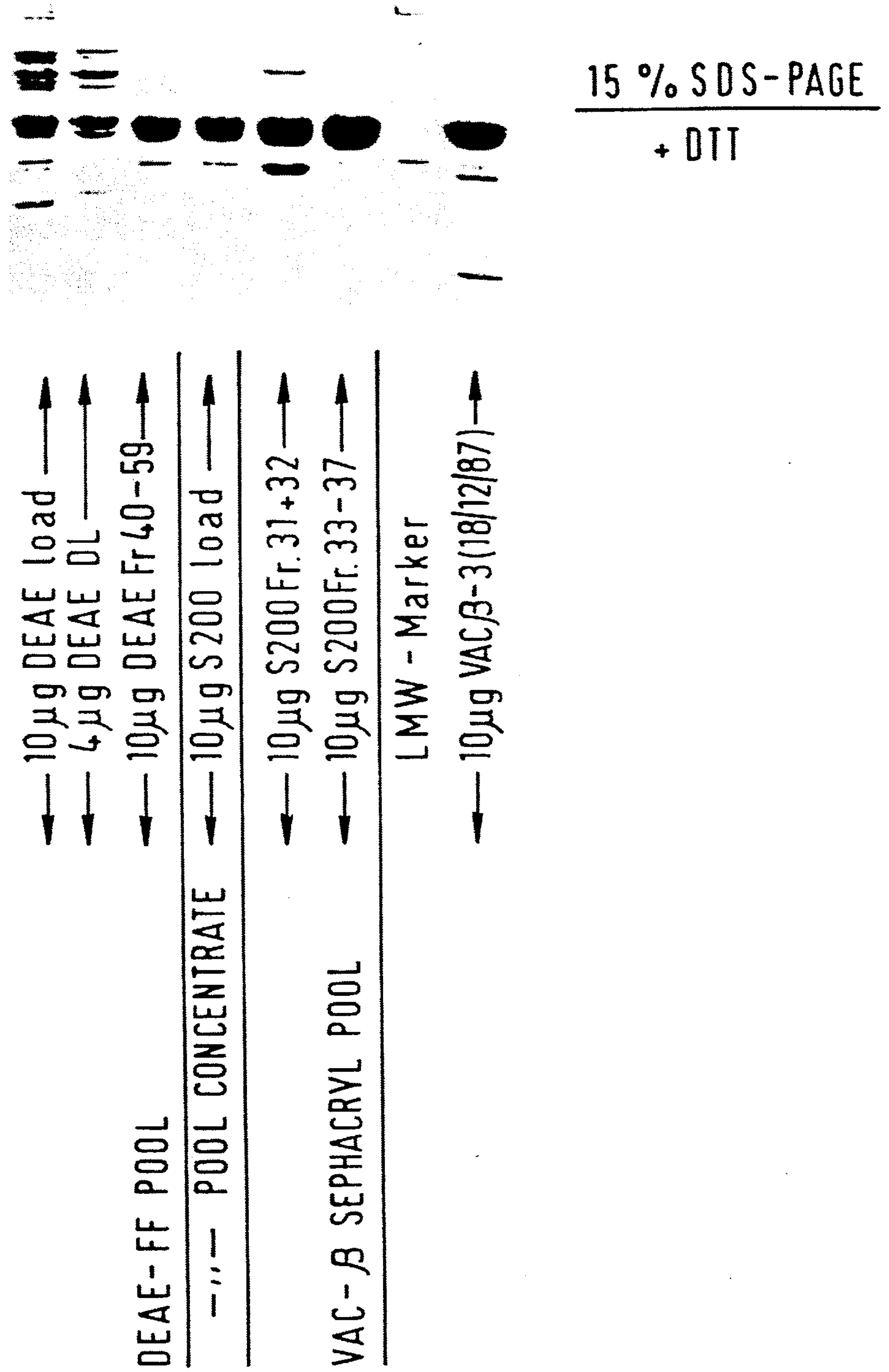
FIG. 45 depicts the purification of recombinant VAC-β, in process samples separated on a 15% SDS-PAGE+DTT.

FIG. 45 shows an SDS gel of VAC-$\beta$ samples.

Trace 1 and 10: molecular weight marker
Trace 2 and 3: in-process sample of VAC-$\beta$ with and without DTT (dithiothreitol)
Trace 4 and 6: 10 mcg of VAC-$\beta$, not reduced
Trace 5 and 7: 10 mcg of VAC-$\beta$ reduced with DTT.
Trace 8 and 9: 1 mcg of VAC-$\beta$, not reduced.

VAC-$\beta$ without reducing agents is detectable as a double band. The more intensive lower band at M approximately 36,000 is the oxidized form, whilst the upper band at M approximately 38,000 is the reduced form of VAC-$\beta$. The quantity distribution of the two forms is easier to see from traces 8 and 9.

After the addition of DTT as reducing agent, therefore, only the upper band is still visible (see traces 3, 5 and 7). Since traces 4 to 7 are greatly overloaded, some bands of residual impurities are also visible in addition to the VAC-$\beta$ bands.

Isoelectric focussing

Staining is carried out with Coomassie Blue. The isoelectric focussing, FIG. 46 (3.3.1988/51) of largely purified VAC-$\beta$ shows that VAC-$\beta$ yields two main bands at pH 5.35 and 5.45, directly from the last purification state (traces 2 and 3). The isoelectric point (pI) of VAC-$\beta$ is hence significantly more basic than that of VAC-$\alpha$ (pI=4.9), which corresponds to expectations, since VAC-$\beta$ contains less acidic amino acids.

After reduction with dithiothreitol (traces 4 and 5) the main band at pH 5.45 is greatly concentrated. This is obviously the reduced form of VAC-$\beta$.

EXAMPLE 13

Construction of expression vectors pRH261/n and pRH281nT (n=5,6,7,8,9)

The expression vector pRH100 described in the E.P.A. No. 186098 has several drawbacks:

a) the distance between the ribosomal binding site (RBS) and the translational start ATG is constant and not optimal.

b) The region between RBS and ATG contains some C's and G's.

c) the −35 region of the trp promoter of *Serratia marcescens* is not optimal compared with the *E. coli* sequence (TTGACT versus TTGACA).

d) There is an unnecessary EcoRI site in front of the promoter.

A set of oligonucleotides was synthesized with the following sequences:

```
: Trp-1 ->      : : Trp-3 ->

AATTGACGCTGATGGCTAAAACATTGTGCAAAAAGAGGGTTGACATTGCC

        CTGCGACTACCGATTTTGTAACACGTTTTTCTCCCAACTGTAACGG

                <- Trp-2 : :

                                    : -> transcriptional start

                                    : : Trp-5 ->

TTCGCGAACCAGTTAACTAGTACACAAGTTCACGGCTCGAGACGGTAAGG

AAGCGCTTGGTCAATTGATCATGTGTTCAAGTGCCGAGCTCTGCCATTCC

                                    <- Trp-4 : :            ----
                                                             RBS

            SstI          ClaI

            ------ EcoRI  ------

                   ------  :

AGGTTTAATATGAGCTCGAATTCAT

TCCAAATTATACTCGAGCTTAAGTAGC

----       ----     <- Trp-6 :

RBS        translational start-ATG

  :  n = 5  :
```

100 pMol of the oligonucleotides Trp-2, Trp-3, Trp-4 and Trp-5 were phosphorylated in 10 ul. After completion of the reaction equimolar amounts (100pMol) of Trp-1 and Trp-2, Trp-3 and Trp-4 as well as Trp-5 and Trp-6 were combined, heated to 100° C. and slowly cooled to allow for annealing. The oligonucleotide pairs were combined and ligated in a total volume of 55 ul. pAT153 was doubly digested and EcoRI and ClaI and large vector fragment isolated. 50 ng pAT153 fragment and 20 pMol synthetic promoter DNA were ligated in 20 ul solution. Competent *E. coli* HB101 were transformed with the resulting plasmid. The plasmid DNA from some of the resulting clones was isolated and the region of the inserted DNA checked by sequencing. One plasmid was selected and named pRH281/5, 5 representing the number of nucleotides between the rbs and the translation start ATG.

Starting from this expression vector the XhoI-SstI insert was replaced by the following oligonucleotide pairs:

```
a)  TCGAGACGGTAAGGAGGTTTAAATATGAGCT         Trp-9
           CTGCCATTCCTCCAAATTTATAC          Trp-10

b)  TCGAGACGGTAAGGAGGTTTAAATAATGAGCT        Trp-11
           CTGCCATTCCTCCAAATTTATTAC         Trp-12

c)  TCGAGACGGTAAGGAGGTTTAAAATAATGAGCT       Trp-13
           CTGCCATTCCTCCAAATTTTATTAC        Trp-14

d)  TCGAGACGGTAAGGAGGTTTAAAAATAATGAGCT      Trp-15
           CTGCCATTCCTCCAAATTTTTATTAC       Trp-16
```

The resulting expression vectors were named pRH281/6 pRH281/7, pRH281/8 and pRH281/9.

These new expression vectors show the following features:

a) the original EcoRI site of pAT153 is destroyed.

b) the −35 region of the *Serratia marcescens* promoter is identical to that of the *E. coli* trp-promoter.

c) there is a singular XhoI site in front of the RBS allowing the substitution of this RBS for another one.

d) the G of the translation start ATG is the first base of an SstI (=SacI) site. Cutting with SstI followed by removal of the 3' overhang creates a blunt end which can be ligated to any cDNA or gene. If this DNA starts with the first base of a translated region, corrected transciption and translation occurs in *E. coli.* e) the SstI site is followed by a singular EcoRI, ClaI and HindIII site which can be used for a directed cloning of any DNA which should be expressed. In addition, it is also possible to use the singular restriction enzyme sites contained in the tetracycline resistance gene.

f) the variation/5 to /9 makes it possible to find the optimal spacing between the rbs and the ATG for any gene to be expressed.

Sometimes it is necessary, for optimum expression and the stability of the plasmid, to have a transcription termination signal behind the expressed gene (R. Gentz et al., *Proc. Natl. Acad. Sci. USA* 78:4936–4940 (1981)). The HindIII-SalI fragment of pRH261/5 was removed and replaced by an oligonucleotide pair containing the phoA transcription terminator (H. Shuttleworth et al., *Nucl. Acids Res.* 14:8689 (1986); C.N. Chang et al., *Gene* 44:121–125 (1986)):

: EBI-456⟶

AGCTTGGATCCGTCGACCGCGCCCGGCAGTGAATTTTCGCTGCCGGGTGG

ACCTAGGCAGCTGGCGCGGGCCGTCACTTAAAAGCGACGGCCCACC

: ———

——— BamHI ———

HindIII SalI

:

TTTTTTTGCTGC

AAAAAAACGACGAGCT

⟵EBI-459 :

10 pMol of the annealed oligonucleotides and 100 ng of the HindIII-SalI cut vector fragment of pRH281/5 were ligated in a volume of 20 ul. After transformation of *E. coli* HB101, isolation of plasmid DNA from some of the colonies and check by sequencing one plasmid was selected and designated as pRH281/5T.

Starting with this plasmid the whole set of expression vectors pRH281/6T, pRH281/7T, pRH281/8T and pRH281/9T was produced using the procedure described above.

EXAMPLE 14

The Effect of Divalent Cations on the Binding of VAC to Phospholipids

Lipids

Dioleoyl-phosphatidylcholine (DOPC, No. P-1013)
Dioleoyl-phosphatidylethanolamine (DOPE, No. P-0510),
Cardiolipine (CL, No. C-5646),
Dioleoyl-phosphatidylglycerol (DOPG, No. P-9664),
Phosphatidylinositol (PI, No. P-0639),
Dioleoyl-phosphatidic acid (DOPA, No. P-2767), Stearylamine (SA, S-6755) and egg yolk sphingomyelin (S-0756) were obtained from Messrs. Sigma Chemical co.

The purity of DOPC and DOPE was checked by thin layer chromatography. Dioleoyl-phosphatidylserine (DOPS) was prepared by conversion of DOPC according to Confurius, P & Zwaal, R. F. A., *Biochim. Biophys. Acta* 488:42 (1988) $^{14}C$-labelled DOPC (specific activity 100,000 dpm/$\mu$g) was obtained from Amersham.

Preparation of double phospholivid coatings on silicon sheets

Double phospholipid coatings were applied using a Langmuir film balance (Lauda Type FW-1) as described by Corsel et al., *J. Colloid Interface Sci.* 111: 544–554 (1986). Hydrophilic silicon sheets were treated for 24 hours in 30% chromosulphuric acid and water and stored in 50% ethanol/water. Before use they were cleaned thoroughly with detergent and water. The film balance was filled with demineralized water and 50 $\mu$M $CaCl_2$. 20 $\mu$l of a solution containing about 2 g/l phospholipid in chloroform were applied to this lower phase. The DOPS fractions in the double layers were checked with $^{14}C$-labelled DOPS mixed with DOPC. The double layers built up were removed from the silicon sheets with the scintillation detergent (Du Pont Formula 989) and the total radioactivity was measured in a scintillation counter.

Measurement of binding by ellipsometry

The adsorption of VAC to the double phospholipid coatings was measured with an automatic ellipsometer as described by Corsel, et al., *J. Colloid Interface Sci.* 111: 544–554 (1986); and Cuypers, P. A. et al., *J. Biol. Chem.* 258: 2426–2431 (1983).

The binding tests were carried out in a hydrophilic dish containing 5 ml of a stirred buffer (0. 05 M tris/HC1; 0. 1 M NaCl; pH=7.5; T=20° C.). The divalent cations were added stepwise in the form of chlorides.

At VAC concentrations <0.1 $\mu$g/ml, the buffer containing the specific VAC concentration was added continuously in order to create a sufficient buffer capacity for VAC.

From the combined polarization and analysis data, the refractive index and the thickness d of the adsorbed film were determined (McCrackin, F. L. et al., *J. Res. Nat. Bur. Stand. Sect.A* 67: 3–377 (1963). The quantity $\Gamma$ of the adsorbed protein layer was determined from the refractive index and thickness by means of a modified Lorentz-Lorenz equation [1] (McCrackin, F. L. et al., *J. Res. Nat. Bur. Stand. Sect.A* 67: 3-377 (1963) ; Kop, J. M. M. et al., *J. Biol. Chem.* 259: 13993-13998 (1984)):

$$1\ \Gamma=3d(n^2-nb^2)/[(n^2+2)(r(nb^2+2)-v(nb^2-1))];$$

nb is the refractive index of the buffer. The values r=0.254 and v=0.71 were used for the specific molar refractivity and the partial specific volume (McCrackin, F. L. et al., *J. Res. Nat. Bur. Stand. Sect.A* 67: 3-377 (1963)).

Results

The effect of divalent cations on the binding of VAC to phospholipids

Figure 53:
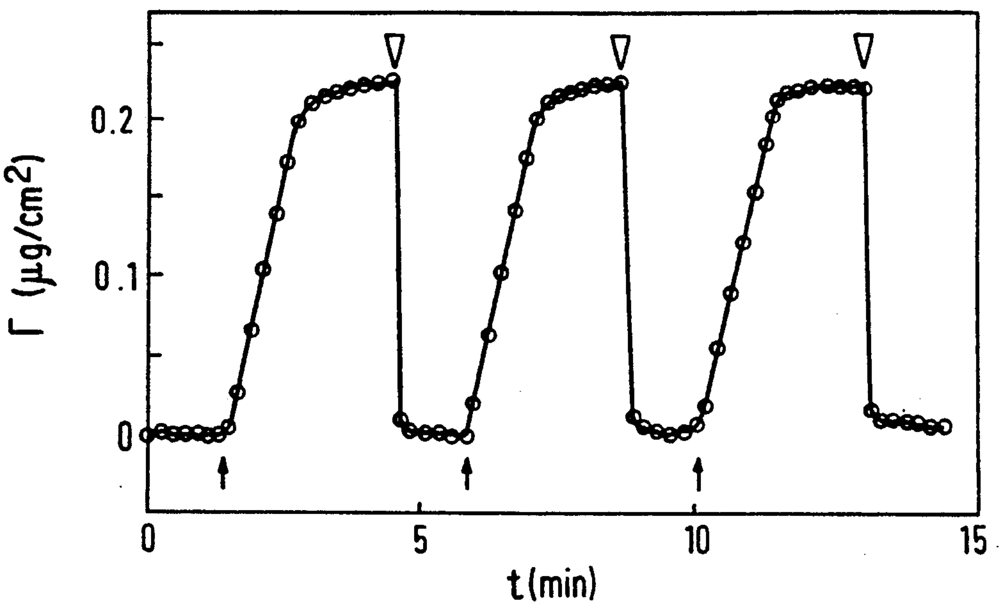
FIG. 53 depicts the alternating adsorption and desorption of VAC on a phospholipid surface induced by increasing or lowering the $CA^{2+}$ concentration. The adsorption of VAC (1 μg/ml) on a 20% DOPS/80% DOPC phospholipid double layer. The addition of $Ca^{2+}$ (3,4,6 mM) is indicated by ↑ or ∇.

VAC binds to phospholipid membranes which consist of 20% DOPS/80% DOPC depending on the concentration of calcium. The subsequent addition of EDTA resulted in total and immediate desorption (FIG. 53). By changing the free $Ca^{2+}$ concentration it was possible to trigger adsorption several times more without any noticeable change in the quantity adsorbed or the rate of adsorption. Irreversible changes in the VAC molecule or the double phospholipid coatings as a result of adsorption or desorption are therefore unlikely. The binding was also totally reversible when the dish was rinsed out with $Ca^{2+}$-free buffer.

Figure 54:
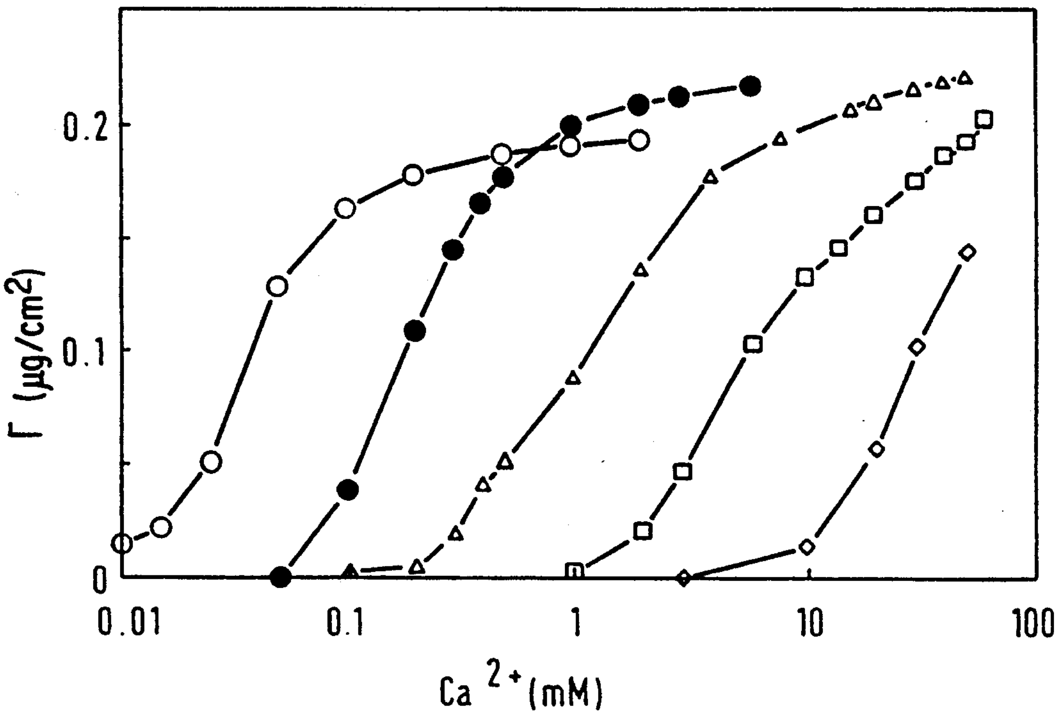
FIG. 54 depicts the influence of phospholipid composition and $Ca^{2+}$ concentration on the adsorption of VAC on a phospholipid surface.

The $Ca^{2+}$ dependency of VAC binding to phospholipids is shown in FIG. 54. The $Ca^{2+}$ dose-activity curve clearly shows a $Ca^{2+}$ concentration at which half the maximum VAC adsorption is achieved: $[Ca^{2+}]_{½}$. The $[Ca^{2+}$ $_{½}$ value depends on the composition of the phospholipid surface. In phospholipid surfaces containing 100%, 20%, 5% and 1% DOPS, $[Ca^{2+}]_{½}$ values of 36 μM, 220 μM, 1.5 mM and 8.6 mM, respectively, were measured (Table 1). These results correspond well to the $[Ca^{2+}]_{½}$ value of 53 μM which was measured for the endonexin II (=VAC) binding to equimolar mixtures of PS/PC vesicles (Schlaepfer, D. D. et. al., *Proc. Natl. Acad. Sci. USA* 84: 6078-6082 (1987). The maximum quantity of adsorbed protein (Γmax) was independent of the DOPS fraction of the membrane and amounted to about 0.217 $\mu g/cm^2$.

In tests using cations other than $Ca^{2+}$ it was found that the binding of VAC to the phospholipids is strongly $Ca^{2+}$-specific (FIG. 55). $Cd^{2+}$, $Zn^{2+}$, $Mn^{2+}$ and $Co^{2+}$ showed a slight promotion of binding; $Ba^{2+}$ and $Mg^{2+}$ had no influence. This property of the cations can to some extent be correlated with the ion radii thereof.

Zinc synergism

High concentrations of zinc ions (1 mM) promote VAC adsorption only to a limited extent (FIG. 55); 50 μM have no influence at all on adsorption. Surprisingly, this concentration influences the binding in the presence of $Ca^{2+}$; synergism can be observed. The $[Ca^{2+}]_{½}$ value fell from 8.6 to 2.7 mM for double layers with only 1% DOPS ($[Zn^{2+}]$=μM) (FIG. 56) . 50 μM $[Zn^{2+}]$ is within the normal range of plasma zinc concentrations.

TABLE 1

Half the maximum VAC-binding to various phospholipid surfaces.

| Lipid (mol %/mol %) $[Ca^{2+}]_{½}$ ± S.D. | Γmax ± S.D. (μg/cm²) | mM |
|---|---|---|
| DOPS (100) | 0.195 ± 0.025 | 0.036 ± 0.013 |
| DOPS/DOPC (20/80) | 0.222 ± 0.014 | 0.22 ± 0.06 |
| DOPS/DOPC (5/95) | 0.229 ± 0.004 | 1.5 ± 0.5 |
| DOPS/DOPC (1/99) | 0.234 ± 0.007 | 8.6 ± 2.5 |
| Cardiolipin/DOPC (20/80) | 0.209 ± 0.011 | 0.039 ± 0.022 |
| DOPG/DOPC (20/80) | 0.212 ± 0.003 | 0.155 ± 0.027 |
| PI/DOPC (20/80) | 0.221 ± 0.005 | 0.47 ± 0.05 |
| DOPA/DOPC (20/80) | 0.207 ± 0.006 | 0.75 ± 0.26 |
| DOPE/DOPC (20/80) | 0.213 ± 0.003 | 0.86 ± 0.21 |
| Sphingomyelin/DOPC (20/80) | 0.225 ± 0.014 | 7 ± 3 |
| DOPC (100) | n.d. | <30 mM |

The maximum VAC-adsorption (Γmax) on the phospholipid surfaces specified together with the calcium concentration which leads to half the maximum VAC binding $[Ca^{2+}]_{½}$ are given as the averages of at least three different experiments with the corresponding standard deviations. n.d.=not determined.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A pharmaceutical composition consisting essentially of a vascular anticoagulant annexine, $Ca^{2+}$, $Zn^{2+}$ and a pharmaceutically acceptable carrier.

2. The pharmaceutical composition according to claim 1, wherein the vascular anticoagulant has the formula

| | | | | | | | | | | | | | | |
|---|---|---|---|---|---|---|---|---|---|---|---|---|---|---|
| 1 | | | | 5 | | | | | 10 | | | | | 15 |
| X | Ala | Gln | Val | Leu | Arg | Gly | Thr | Val | Thr | Asp | Phe | Pro | Gly | Phe |
| | | | | 20 | | | | | 25 | | | | | 30 |
| Asp | Glu | Arg | Ala | Asp | Ala | XX | Thr | Leu | Arg | Lys | Ala | Met | Lys | Gly |
| | | | | 35 | | | | | 40 | | | | | 45 |
| Leu | Gly | Thr | Asp | Glu | Glu | Ser | Ile | Leu | Thr | Leu | Leu | Thr | Ser | Arg |
| | | | | 50 | | | | | 55 | | | | | 60 |
| Ser | Asn | Ala | Gln | Arg | Gln | Glu | Ile | Ser | Ala | Ala | Phe | Lys | Thr | Leu |
| | | | | 65 | | | | | 70 | | | | | 75 |
| Phe | Gly | Arg | Asp | Leu | Leu | Asp | Asp | Leu | Lys | Ser | Glu | Leu | Thr | Gly |
| | | | | 80 | | | | | 85 | | | | | 90 |
| Lys | Phe | Glu | Lys | Leu | Ile | Val | Ala | Leu | Met | Lys | Pro | Ser | Arg | Leu |
| | | | | 95 | | | | | 100 | | | | | 105 |
| Tyr | Asp | Ala | Tyr | Glu | Leu | Lys | His | Ala | Leu | Lys | Gly | Ala | Gly | Thr |
| | | | | 110 | | | | | 115 | | | | | 120 |
| Asn | Glu | Lys | Val | Leu | Thr | Glu | Ile | Ile | Ala | Ser | Arg | Thr | Pro | Glu |
| | | | | 125 | | | | | 130 | | | | | 135 |
| Glu | Leu | Arg | Ala | Ile | Lys | Gln | Val | Tyr | Glu | Glu | Glu | Tyr | Gly | Ser |
| | | | | 140 | | | | | 145 | | | | | 150 |
| Ser | Leu | Glu | Asp | Asp | Val | Val | Gly | Asp | Thr | Ser | Gly | Tyr | Tyr | Gln |
| | | | | 155 | | | | | 160 | | | | | 165 |
| Arg | Met | Leu | Val | Val | Leu | Leu | Gln | Ala | Asn | Arg | Asp | Pro | Asp | Ala |

-continued

| | | | | | | | | | | | | | | |
|---|---|---|---|---|---|---|---|---|---|---|---|---|---|---|
| | | | | 170 | | | | | 175 | | | | | 180 |
| Gly | Ile | Asp | Glu | Ala | Gln | Val | Glu | Gln | Asp | Ala | Gln | Ala | Leu | Phe |
| | | | | 185 | | | | | 190 | | | | | 195 |
| Gln | Ala | Gly | Glu | Leu | Lys | Trp | Gly | Thr | Asp | Glu | Glu | Lys | Phe | Ile |
| | | | | 200 | | | | | 205 | | | | | 210 |
| Thr | Ile | Phe | Gly | Thr | Arg | Ser | Val | Ser | His | Leu | Arg | Lys | Val | Phe |
| | | | | 215 | | | | | 220 | | | | | 225 |
| Asp | Lys | Tyr | Met | Thr | Ile | Ser | Gly | Phe | Gln | Ile | Glu | Glu | Thr | Ile |
| | | | | 230 | | | | | 235 | | | | | 240 |
| Asp | Arg | Glu | Thr | Ser | Gly | Asn | Leu | Glu | Gln | Leu | Leu | Leu | Ala | Val |
| | | | | 245 | | | | | 250 | | | | | 255 |
| Val | Lys | Ser | Ile | Arg | Ser | Ile | Pro | Ala | Tyr | Leu | Ala | Glu | Thr | Leu |
| | | | | 260 | | | | | 265 | | | | | 270 |
| Tyr | Tyr | Ala | Met | Lys | Gly | Ala | Gly | Thr | Asp | Asp | His | Thr | Leu | Ile |
| | | | | 275 | | | | | 280 | | | | | 285 |
| Arg | Val | Met | Val | Ser | Arg | Ser | Glu | Ile | Asp | Leu | Phe | Asn | Ile | Arg |
| | | | | 290 | | | | | 295 | | | | | 300 |
| Lys | Glu | Phe | Arg | Lys | Asn | Phe | Ala | Thr | Ser | Leu | Tyr | Ser | Met | Ile |
| | | | | 305 | | | | | 310 | | | | | 315 |
| Lys | Gly | Asp | Thr | Ser | Gly | Asp | Tyr | Lys | Lys | Ala | Leu | Leu | Leu | Leu |
| | | | | 320 | | | | | | | | | | |
| Cys | Gly | Glu | Asp | Asp | * | | | | | | | | | |

wherein x represents hydrogen, a methionine group or a blocking group on the alanine group at position 2 and XX represents Glu or Asp.

3. The pharmaceutical composition of claim 2, wherein said annexine is part of an aggregate of two or more annexines which are linked by disulfide bonds between one or more cysteine groups on the respective annexine.

4. The pharmaceutical composition of claim 3, wherein said cysteine groups are at position 316 on the annexine.

5. The pharmaceutical composition according to claim 1, wherein the vascular anticoagulant annexine has the formula:

| | | | | | | | | | | | | | | |
|---|---|---|---|---|---|---|---|---|---|---|---|---|---|---|
| 1 | | | | 5 | | | | | 10 | | | | | 15 |
| X | Ala | Trp | Trp | Lys | Ala | Trp | Ile | Glu | Gln | Glu | Gly | Val | Thr | Val |
| | | | | 20 | | | | | 25 | | | | | 30 |
| Lys | Ser | Ser | Ser | His | Phe | Asn | Pro | Asp | Pro | Asp | Ala | Glu | Thr | Leu |
| | | | | 35 | | | | | 40 | | | | | 45 |
| Tyr | Lys | Ala | Met | Lys | Gly | Ile | Gly | Thr | Asn | Glu | Gln | Ala | Ile | Ile |
| | | | | 50 | | | | | 55 | | | | | 60 |
| Asp | Val | Leu | Thr | Lys | Arg | Ser | Asn | Thr | Gln | Arg | Gln | Gln | Ile | Ala |
| | | | | 65 | | | | | 70 | | | | | 75 |
| Lys | Ser | Phe | Lys | Ala | Gln | Phe | Gly | Lys | Asp | Leu | Thr | Glu | Thr | Leu |
| | | | | 80 | | | | | 85 | | | | | 90 |
| Lys | Ser | Glu | Leu | Ser | Gly | Lys | Phe | Glu | Arg | Leu | Ile | Val | Ala | Leu |
| | | | | 95 | | | | | 100 | | | | | 105 |
| Met | Tyr | Pro | Pro | Tyr | Arg | Tyr | Glu | Ala | Lys | Glu | Leu | His | Asp | Ala |
| | | | | 110 | | | | | 115 | | | | | 120 |
| Met | Lys | Gly | Leu | Gly | Thr | Lys | Glu | Gly | Val | Ile | Ile | Glu | Ile | Leu |
| | | | | 125 | | | | | 130 | | | | | 135 |
| Ala | Ser | Arg | Thr | Lys | Asn | Gln | Leu | Arg | Glu | Ile | Met | Lys | Ala | Tyr |
| | | | | 140 | | | | | 145 | | | | | 150 |
| Glu | Glu | Asp | Tyr | Gly | Ser | Ser | Leu | Glu | Glu | Asp | Ile | Gln | Ala | Asp |
| | | | | 155 | | | | | 160 | | | | | 165 |
| Thr | Ser | Gly | Tyr | Leu | Glu | Arg | Ile | Leu | Val | Cys | Leu | Leu | Gln | Gly |
| | | | | 170 | | | | | 175 | | | | | 180 |
| Ser | Arg | Asp | Asp | Val | Ser | Ser | Phe | Val | Asp | Pro | Ala | Leu | Ala | Leu |
| | | | | 185 | | | | | 190 | | | | | 195 |
| Gln | Asp | Ala | Gln | Asp | Leu | Tyr | Ala | Ala | Gly | Glu | Lys | Ile | Arg | Gly |
| | | | | 200 | | | | | 205 | | | | | 210 |
| Thr | Asp | Glu | Met | Lys | Phe | Ile | Thr | Ile | Leu | Cys | Thr | Arg | Ser | Ala |
| | | | | 215 | | | | | 220 | | | | | 225 |
| Thr | His | Leu | Leu | Arg | Val | Phe | Glu | Glu | Tyr | Glu | Lys | Ile | Ala | Asn |
| | | | | 230 | | | | | 235 | | | | | 240 |
| Lys | Ser | Ile | Glu | Asp | Ser | Ile | Lys | Ser | Glu | Thr | His | Gly | Ser | Leu |
| | | | | 245 | | | | | 250 | | | | | 255 |
| Glu | Glu | Ala | Met | Leu | Thr | Val | Val | Lys | Cys | Thr | Gln | Asn | Leu | His |
| | | | | 260 | | | | | 265 | | | | | 270 |
| Ser | Tyr | Phe | Ala | Glu | Arg | Leu | Tyr | Tyr | Ala | Met | Lys | Gly | Ala | Gly |
| | | | | 275 | | | | | 280 | | | | | 285 |
| Thr | Arg | Asp | Gly | Thr | Leu | Ile | Arg | Asn | Ile | Val | Ser | Arg | Ser | Glu |
| | | | | 290 | | | | | 295 | | | | | 300 |
| Ile | Asp | Leu | Asn | Leu | Ile | Lys | Cys | His | Phe | Lys | Lys | Met | Tyr | Gly |
| | | | | 305 | | | | | 310 | | | | | 315 |
| Lys | Thr | Leu | Ser | Ser | Met | Ile | Met | Glu | Asp | Thr | Ser | Gly | Asp | Tyr |
| | | | | 320 | | | | | 325 | | | | | |
| Lys | Asn | Ala | Leu | Leu | Ser | Leu | Val | Gly | Ser | Asp | Pro | * | | |

wherein X represents a hydrogen, a methionine or a blocking group on the alanine at position 2.

6. The pharmaceutical composition of claim 5, wherein said annexine is part of an aggregate of two or more annexines which are linked by disulfide bonds between one or more cysteine groups on the respective annexine.

7. The pharmaceutical composition of claim 6, wherein said cysteine groups are at position 161, 206, 250 or 293 of the annexine.

8. The pharmaceutical composition according to claim 1, comprising between 0.01 and 100 mM of $Ca^{2+}$ and between 0.1 and 100 $\mu M$ $Zn^{2+}$.

9. The pharmaceutical composition according to claim 1, comprising between 0.03 and 10 mM $Ca^{2+}$.

10. The pharmaceutical composition according to claim 1, comprising between 0.1 and 100 $\mu M$ $Zn^{2+}$.

11. The pharmaceutical composition according to claim 1, comprising between 18 and 30 $\mu M$ $Zn^{2+}$.

12. The pharmaceutical composition according to claim 1, wherein said $Zn^{2+}$ is present at a concentration which is within the range of the normal plasma zinc concentration.

13. The pharmaceutical composition according to claim 1, comprising between 0.01 and 100 mM $Ca^{2+}$ and between 0.1 and 100 $\mu M$ $Zn^{2+}$.

14. The pharmaceutical composition according to claim 1, comprising between 0.03 and 10 mM $Ca^{2+}$ and between 1.8 and 30 $\mu M$ of $Zn^{2+}$.

15. The pharmaceutical composition according to claim 1, comprising $Ca^{2+}$ and $Zn^{2+}$ at concentrations corresponding to the respective normal plasma concentrations.

16. A process for preparing the pharmaceutical composition according to claim 1, wherein an annexine is mixed with $Ca^{2+}$ and $Zn^{2+}$ and with a pharmaceutically acceptable carrier.

17. The process of claim 16, wherein the pharmaceutical composition is subsequently freeze-dried.

18. A method of preventing the coagulation of blood comprising mixing blood with a vascular anticoagulant annexine, $Ca^{2+}$ and $Zn^{2+}$.

* * * * *